United States Patent
Mellgård et al.

(10) Patent No.: US 12,128,090 B2
(45) Date of Patent: *Oct. 29, 2024

(54) METHODS OF PROPHYLACTIC TREATMENT USING RECOMBINANT VWF (rVWF)

(71) Applicant: Takeda Pharmaceutical Company Limited, Osaka (JP)

(72) Inventors: Björn Mellgård, Cambridge, MA (US); Bruce Ewenstein, Brookline, MA (US)

(73) Assignee: Takeda Pharmaceutical Company Limited, Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/778,771

(22) Filed: Jan. 31, 2020

(65) Prior Publication Data
US 2020/0261546 A1   Aug. 20, 2020

Related U.S. Application Data

(60) Provisional application No. 62/800,370, filed on Feb. 1, 2019.

(51) Int. Cl.
*A61K 38/37* (2006.01)
*G01N 33/86* (2006.01)
*A61K 9/00* (2006.01)

(52) U.S. Cl.
CPC ............ *A61K 38/37* (2013.01); *G01N 33/86* (2013.01); *A61K 9/0019* (2013.01); *G01N 2333/755* (2013.01)

(58) Field of Classification Search
None
See application file for complete search history.

(56) References Cited

U.S. PATENT DOCUMENTS

| | | | |
|---|---|---|---|
| 3,941,763 A | 3/1976 | Sarantakis et al. | |
| 4,179,337 A | 12/1979 | Davis et al. | |
| 4,301,144 A | 11/1981 | Iwashita et al. | |
| 4,496,689 A | 1/1985 | Mitra | |
| 4,640,835 A | 2/1987 | Shimizu et al. | |
| 4,670,417 A | 6/1987 | Iwasaki et al. | |
| 4,791,192 A | 12/1988 | Nakagawa et al. | |
| 5,854,403 A | 12/1998 | Bernhard et al. | |
| 6,531,577 B1 | 3/2003 | Kaergaard et al. | |
| 7,005,502 B1 | 2/2006 | Schwarz et al. | |
| 7,335,634 B2 | 2/2008 | Walter et al. | |
| 8,173,597 B2 | 5/2012 | Schwarz et al. | |
| 8,597,910 B1 | 12/2013 | Ginsburg et al. | |
| 8,852,888 B2 | 10/2014 | Grillberger et al. | |
| 9,409,971 B2 | 8/2016 | Grillberger et al. | |
| 10,632,176 B2 * | 4/2020 | Chapman | A61K 38/36 |
| 10,905,746 B2 * | 2/2021 | Chapman | A61K 38/37 |
| 11,529,395 B2 * | 12/2022 | Chapman | A61K 38/37 |
| 12,016,904 B2 * | 6/2024 | Chapman | A61K 38/36 |
| 2005/0239171 A1 | 10/2005 | Mitterer et al. | |
| 2006/0094104 A1 | 5/2006 | Grillberger et al. | |
| 2006/0160948 A1 | 7/2006 | Scheiflinger et al. | |
| 2007/0212770 A1 | 9/2007 | Grillberger et al. | |
| 2008/0009040 A1 | 1/2008 | Grillberger et al. | |
| 2010/0099603 A1 | 4/2010 | Schnecker et al. | |
| 2010/0286047 A1 | 11/2010 | Kronthaler | |
| 2012/0035110 A1 | 2/2012 | Grillberger et al. | |
| 2012/0316116 A1 | 12/2012 | Scheiflinger et al. | |
| 2016/0129090 A1 | 5/2016 | Schnecker et al. | |
| 2018/0051067 A1 * | 2/2018 | Moses | C07K 14/755 |
| 2019/0091299 A1 * | 3/2019 | Chapman | A61K 38/36 |
| 2022/0395560 A1 * | 12/2022 | Mellgård | A61P 7/04 |

FOREIGN PATENT DOCUMENTS

| | | |
|---|---|---|
| CA | 2189947 | 8/1997 |
| EP | 1593390 A1 | 11/2005 |
| JP | H9-221432 | 5/1997 |
| JP | 2005/320330 A | 11/2005 |
| WO | WO 86/06096 | 10/1986 |
| WO | WO 1996/10584 A1 | 4/1996 |
| WO | WO 1997/034930 A1 | 9/1997 |
| WO | WO 1998/38219 A1 | 9/1998 |
| WO | WO 2004/039337 | 5/2004 |
| WO | WO 2005/012354 A1 | 2/2005 |
| WO | WO 2006/071801 A2 | 7/2006 |
| WO | WO 2008/151817 A1 | 12/2008 |
| WO | WO 2009/062100 A1 | 5/2009 |
| WO | WO 2009/086400 A3 | 7/2009 |
| WO | WO 2009/156137 A1 | 12/2009 |

(Continued)

OTHER PUBLICATIONS

Suiter et al. "Recombinant Human Von Willebrand Factor (rhVWF): First-In-Human Study Evaluating Pharmacokinetics, Demonstrating Safety and Tolerability In Type 3 Von Willebrand Disease". Blood, vol. 116, Issue 21, 2010, p. 237, ISSN 0006-4971, https://doi.org/10.1182/blood.V116.21.237.237. (cited Nov. 9, 2022 IDS).*
Abuchowski, A. et al., "Soluble Polymer-Enzyme Adducts," Chapter 13 in Enzymes as Drugs, Holcenberg, J.S. et al., ed., John Wiley and Sons, New York, 1981:367-383.
Andersson, L.-O. et al., "Isolation and characterization of human factor VIII: Molecular forms in commercial factor VIII concentrate, cryoprecipitate, and plasma," Proc. Natl. Acad. Sci. USA, May 1986, vol. 83, pp. 2979-2983.
Berntorp, E. et al., "Treatment and prevention of acute bleedings in von Willebrand disease—efficacy and safety of Wilate®, a new generation von Willebrand factor/factor VIII concentrate," Haemophilia, 2009;15(1):122-130.
Carpenter, J.F. et al., "Interactions of Stabilizing Additives With Proteins During Freeze-Thawing and Freeze-Drying," Develop. Biol. Standard, 1991;225-239.

(Continued)

*Primary Examiner* — Maury A Audet
(74) *Attorney, Agent, or Firm* — Morgan, Lewis & Bockius LLP

(57) ABSTRACT

The present invention relates to a method for prophylactic treatment of spontaneous bleeding in a subject with severe von Willebrand Disease comprising administering a therapeutic amount of recombinant von Willebrand Factor (rVWF) to the subject.

23 Claims, 24 Drawing Sheets
Specification includes a Sequence Listing.

(56) References Cited

FOREIGN PATENT DOCUMENTS

| WO | WO 2010/048275 A2 | 4/2010 |
|---|---|---|
| WO | WO 2011/017414 A2 | 2/2011 |
| WO | WO 2012/006591 A1 | 1/2012 |
| WO | WO 2012/171031 A1 | 12/2012 |
| WO | WO 2019/010497 A1 | 1/2019 |

OTHER PUBLICATIONS

Castaman, G. et al., "von Willebrand's disease in the year 2003: towards the complete identification of gene defects for correct diagnosis and treatment," Haematological/Journal of Hematology, Jan. 2003, vol. 88, No. 1, pp. 94-108.
Chang, B.S. et al., "Development of a stable freeze-dried formulation of recombinant human interleukin-1 receptor antagonist," Pharm Res., 1996; 13(2):243-249.
Chang, B.S. et al., "Surface-Induced Denaturation of Proteins during Freezing and its Inhibition by Surfactants," Pharm Sci., 1996;85(12):1325-1330.
Chen, B. et al., "Influence of calcium ions on the structure and stability of recombinant human deoxyribonuclease I in the aqueous and lyophilized states," Pharm. Sci., 1999;88(4):477-482.
Chen, B. et al., "Influence of histidine on the stability and physical properties of a fully human antibody in aqueous and solid forms," Pharm Res., 2003;20(12):1952-60.
Chen, T., "Formulation concerns of protein drugs," Drug Development and Industrial Pharmacy, 1992;18:1311-1354.
Denis, C.V. et al., "Clearance of von Willebrand factor," Thromb. Haemost., 2008, vol. 99, pp. 271-278.
Derrick, T.S. et al., "Effect of metal cations on the conformation and inactivation of recombinant human factor VIII," Pharm. Sci., 2004;93(10):2549-57.
Fatouros, A. et al., "Recombinant factor VIII SQ—influence of oxygen, metal ions, pH and ionic strength on its stability in aqueous solution," Int. J. Pharm., 1997;155:121-131.
Fernandes, A.I. et al., "Polysialyated asparaginase: preparation, activity and pharmacokinetics," Biochim. Biophys. Acta., 1997;1341:26-34.
Fijnvandraat, K. et al., "Inter-individual variation in half-life of infused recombinant factor VIII is related to pre-infusion von Willebrand factor antigen levels," British Journal of Haematology, 1995, vol. 91, pp. 474-476.
Fischer, B.E. et al., "Effect of Multimerization of Human Recombinant von Willebrand Factor on Platelet Aggregation, Binding to Collagen and Binding of Coagulation Factor VIII," Thrombosis Research, 1996, vol. 84, No. 1, pp. 55-66.
Fischer, B.E. et al., "Structural Analysis of Recombinant von Willebrand Factor Produced at Industrial Scale Fermentation of Transformed CHO Cells Co-Expressing Recombinant Furin," FEBS Letters, Nov. 20, 1995, vol. 375, pp. 259-262.
Fischer, B.E., "Recombinant von Willebrand factor: potential therapeutic use," Journal of Thrombosis and Thrombolysis, Jan. 1, 1999, vol. 8, pp. 197-205.
Franchini, M. et al., "Gastrointestinal angiodysplasia and bleeding in von Willebrand disease," Thromb Haemost., 2014;112(3):427-431.
Franchini, M. et al., "Von Willebrand disease-associated angiodysplasia: a few answers, still many questions," Br J Haemost., 2013;161(2):177-182.
Franchini, M. et al., "Von Willebrand factor (Vonvendi®): the first recombinant product licensed for the treatment of von Willebrand disease," Expert Rev Hematol., 2016;9(9):825-830.
GenBank Accession No. NM_000543, "*Homo sapiens* sphingomyelin phosphodiesterase 1 (SMPD1), transcript variant 1, mRNA," 2018, 5 pages.
GenBank Accession No. NM_000552, "*Homo sapiens* von Willebrand factor (VWF), mRNA," 2018, 10 pages.
Gill Joan Cox et al: "Recombinant Von Willebrand Factor Administration: Dosing Considerations and Rapid Stabilization of Endogenous Plasma FVIII Levels in Patients with Severe Von Willebrand Disease", XP002784853, Database accession No. REV201800668643 abstract, Blood, vol. 130, Suppl. 1, Dec. 7, 2017 (Dec. 7, 2017), p. 3682, 59th Annual Meeting of the American-Society-Of-Hematology (ASH).
Hollander-Rodriguez, J.C. et al., "Hyperkalemia," Am. Fam. Physician., 2006;73(2):283-90.
International Search Report mailed Sep. 7, 2012, for International Patent Application No. PCT/US2012/041957, 6 pages.
Kappelgaard, A.M. et al., "Liquid Growth Hormone: Preservatives and Buffers," Horm Res., 2004;3(suppl 1):98-103.
Keeling, D. et al., "Guideline on the selection and use of therapeutic products to treat hemophilia and other hereditary bleeding disorders," Haemophilia, 2008, vol. 14, pp. 671-684.
Lam, X.M. et al., "Antioxidants for Prevention of Methionine Oxidation in Recombinant Monoclonal Antibody HER2," J. Pharm. Sci., 1997;86(11):1250-5.
Laursen, T. et al., "Pain Perception after Subcutaneous Injections of Media Containing Different Buffers," Basic Clin Pharmacol Toxicol., 2006;98(2):21821.
Mackenzie, A.P., "Non-equilibrium freezing behavior of aqueous systems," Phil Trans R Soc London, Ser B, Biol, 1977;278:167-189.
Meulien, P. et al., "Processing and characterization of recombinant von Willebrand factor expressed in different cell types using a vaccinia virus vector," Thromb. Haemost., Jan. 23, 1992;67(1):154-160.
Minogue, S.C. et al., "Bacteriostatic Saline Containing Benzyl Alcohol Decreases the Pain Associated with the Injection of Propofol," Anesth Analg., 2005;100(3):683-6.
Randi, A.M. et al., "Von Willebrand factor and angiogenesis: basic and applied issues," J Thromb Haemost., 2017;15(1):13-20.
Randi, A.M., "Endothelial dysfunction in von Willebrand disease: angiogenesis and angiodysplasia," Thromb Res., 2016;141(suppl 2):S55-58.
Remmele, R.L. Jr et al., "Minimization of Recombinant Human Flt3 Ligand Aggregation at the Tm Plateau: A Matter of Thermal Reversibility," Biochemistry, 1999;38(16):5241-7.
Remmele, R.L. Jr. et al., "Interleukin-1 receptor (IL-1R) liquid formulation development using differential scanning calorimetry," Pharm Res., 1998;15(2):200-8.
Rodeghiero, F. et al., "Treatment of von Willebrand disease," Semin Heamtol., Jan. 2005;42(1 ):29-35.
Roy, S. et al., "Effects of Benzyl Alcohol on Aggregation of Recombinant Human Interleukin-1-Receptor Antagonist in Reconstituted Lyophilized Formulations," J Pharm Sci., 2005;94(2):382-96.
Saenko, E.L. et al., "Strategies towards a longer acting factor VIII," Haemophilia, 2006;12:42-51.
Schlokat, E. et al., "Production of Highly Homogenous and Structurally Intact Recombinant von Willebrand Factor Multimers by Furin-Mediated Propeptide Removal in Vitro," Dec. 1, 1996, vol. 24, Part 3, pp. 257-267.
Selvam, S. et al., "Angiodysplasia in von Willibrand Disease: Understanding the Clinical and Basic Science," Semin Thromb Hemost., 2017.
Singal et al., "Recombinant von Willebrand Factor: a first-of-its kind product for von Willebrand disease", Drugs of Today, Dec. 1, 2016 (Dec. 1, 2016), pp. 653-664.
Tang, X. et al., "Design of freeze-drying processes for pharmaceuticals: practical advice," Pharm. Res., 2004;21:191-200.
Tomita, M. et al., "Sensitized photooxidation if histidine and its derivatives. Products and mechanism of the reaction," Biochemistry, 1969;8(12):5149-60.
Turecek, P.L. et al., "Biochemical and Functional Characterization of a Serum-Free rVWF Drug Candidate," Blood, Nov. 1, 2006, vol. 108, No. 11, p. 303A., Abstract.
Turecek, P.L. et al., "Biochemical and Functional Characterization of Chemically Modified Recombinant von Willebrand Factor (rVWF) as a Carrier Prolonging Survival of RFVIII in Hemophilia a Knock-Out Mice," J. Thromb. Haemost., Aug. 2007; vol. 5 Supplement 2: O-M-018, 3 pages.
Turecek, P.L. et al., "Comparative Study on Collagen-Binding Enzyme-Linked Immunosorbent Assay and Ristocetin Cofactor

(56) References Cited

OTHER PUBLICATIONS

Activity Assays for Detection of Functional Activity of von Willebrand Factor," Semin. Thromb. Hemost., 2002;28:149-160.

Turecek, P.L. et al., "In Vivo Characterization of Recombinant von Willebrand Factor in Dogs With von Willebrand Disease," Blood, Nov. 1, 1997, vol. 90, No. 9, pp. 3555-3567.

Turecek, P.L. et al., "PEG Modified rVWF Prolongs the Survival of Native rFVIII in Hemophilia A Knock-Out Mice," Blood, 2006, vol. 108: Abstract 1002, 1 page.

Van Wezel, A.L., "Growth of Cell-strains and Primary Cells on Micro-carriers in Homogeneous Culture," Nature, Oct. 7, 1967, vol. 216, pp. 64-65.

Varadi, K. et al., "In Vivo Cleavage of Recombinant VWF Upon Intravenous Administration in Preclinical and Clinical Setting," Blood, Nov. 1, 2011, vol. 118, No. 21, p. 549.

Vicky Mcdonald: "Inherited bleeding disorders", Medicine, Apr. 1, 2017 (Apr. 1, 2017), XP055507424.

Web Archive of "Study NCT02283268 Last updated: Jun. 26, 2015", Oct. 6, 2015, https://web.archive.org/web/20151006100604/https://clinicaltrials.gov/ct2/show/NCT02283268.

Suiter, T. et al., "Recombinant Human Von Willebrand Factor (rhVWF): First-In-Human Study Evaluating Pharmacokinetics, Demonstrating Safety and Tolerability In Type 3 Von Willebrand Disease", Blood, vol. 116, Issue 21, 2010, p. 237, ISSN 0006-4971, https://doi.org/10.1182/blood.V116.21.237.237.

Castaman, Giancarlo. "Treatment of von Willebrand disease with FVIII/VWF concentrates." Blood transfusion = Trasfusione del sangue vol. 9 Suppl 2,Suppl 2 (2011): s9-13. doi:10.2450/2011.003S.

Kahlon, A et al. "Quantification of perioperative changes in von Willebrand factor and factor VIII during elective orthopaedic surgery in normal individuals." Haemophilia : the official journal of the World Federation of Hemophilia vol. 19,5 (2013): 758-64. doi:10.1111/hae.12185.

"ACOG committee opinion No. 557: Management of acute abnormal uterine bleeding in nonpregnant reproductive-aged women." Obstetrics and gynecology vol. 121,4 (2013): 891-896. doi:10.1097/01.AOG.0000428646.67925.9a.

Adeyemi-Fowode, Oluyemisi A et al. "Levonorgestrel-Releasing Intrauterine Device Use in Female Adolescents with Heavy Menstrual Bleeding and Bleeding Disorders: Single Institution Review." Journal of pediatric and adolescent gynecology vol. 30,4 (2017): 479-483. doi:10.1016/j.jpag.2016.04.001.

Akers et al., Peptides and proteins as parenteral solutions, chapter 8, IN: Frokjaer et al. (eds), Pharmaceutical Formulation Development of Peptides and Proteins, CRC Press (2000).

Amesse, Lawrence S et al. "Oral contraceptives and DDAVP nasal spray: patterns of use in managing vWD-associated menorrhagia: a single-institution study." Journal of pediatric hematology/oncology vol. 27,7 (2005): 357-63. doi:10.1097/01.mph.0000173175.95152.95.

Chi, Claudia et al. "Levonorgestrel-releasing intrauterine system for the management of heavy menstrual bleeding in women with inherited bleeding disorders: long-term follow-up." Contraception vol. 83,3 (2011): 242-7. doi:10.1016/j.contraception.2010.07.010.

Connell, Nathan T et al. "ASH ISTH NHF WFH 2021 guidelines on the management of von Willebrand disease." Blood advances vol. 5,1 (2021): 301-325. doi:10.1182/bloodadvances.2020003264.

De Wee, E M et al. "Gynaecological and obstetric bleeding in moderate and severe von Willebrand disease." Thrombosis and haemostasis vol. 106,5 (2011): 885-92. doi:10.1160/TH11-03-0180.

Higgins, Russell A, and Andrew J Goodwin. "Automated assays for von Willebrand factor activity." American journal of hematology vol. 94,4 (2019): 496-503. doi:10.1002/ajh.25393.

International Preliminary Report on Patentability mailed Jul. 27, 2021, for International Patent Application No. PCT/US2020/016194, 8 pages.

International Search Report mailed Jun. 3, 2020, for International Patent Application No. PCT/US2020/016194, 5 pages.

James, Paula D et al. "ASH ISTH NHF WFH 2021 guidelines on the diagnosis of von Willebrand disease." Blood advances vol. 5,1 (2021): 280-300. doi:10.1182/bloodadvances.2020003265.

Jennings and Lugowski, J. Immunochemistry of groups A, B, and C meningococcal polysaccharidetetanustoxoid conjugates. 1981; 127:1011-8.

Kadir, R A et al. "The impact of menstrual disorders on quality of life in women with inherited bleeding disorders." Haemophilia : the official journal of the World Federation of Hemophilia vol. 16,5 (2010): 832-9. doi:10.1111/j.1365-2516.2010.02269.x.

Kingman, C E C et al. "The use of levonorgestrel-releasing intrauterine system for treatment of menorrhagia in women with inherited bleeding disorders." BJOG : an international journal of obstetrics and gynaecology vol. 111,12 (2004): 1425-8. doi:10.1111/j.1471-0528.2004.00305.x.

Kouides, Peter A et al. "Multisite management study of menorrhagia with abnormal laboratory haemostasis: a prospective crossover study of intranasal desmopressin and oral tranexamic acid." British journal of haematology vol. 145,2 (2009): 212-20. doi:10.1111/j.1365-2141.2009.07610.x.

Lukes, Andrea S et al. "Use of the levonorgestrel-releasing intrauterine system in women with hemostatic disorders." Fertility and sterility vol. 90,3 (2008): 673-7. doi:10.1016/j.fertnstert.2007.07.1315.

Magnay, Julia L et al. "Pictorial methods to assess heavy menstrual bleeding in research and clinical practice: a systematic literature review." BMC women's health vol. 20,1 24. Feb. 10, 2020, doi:10.1186/s12905-020-0887-y.

Merrifield, J. Am. Chem. Soc., 85:2149 (1963).

Michiels, Jan Jacques et al. "Diagnostic Differentiation of von Willebrand Disease Types 1 and 2 by von Willebrand Factor Multimer Analysis and DDAVP Challenge Test." Clinical and applied thrombosis/hemostasis : official journal of the International Academy of Clinical and Applied Thrombosis/Hemostasis vol. 23,6 (2017): 518-531. doi:10.1177/1076029616647157.

Mohammed, Soma, and Emmanuel J Favaloro. "Laboratory Testing for von Willebrand Factor: Factor VIII Binding (for 2N VWD)." Methods in molecular biology (Clifton, N.J.) vol. 1646 (2017): 461-472. doi:10.1007/978-1-4939-7196-1_34.

Ni, Y et al. "Establishment and characterization of a new and stable collagen-binding assay for the assessment of von Willebrand factor activity." International journal of laboratory hematology vol. 35,2 (2013): 170-6. doi:10.1111/ijlh.12019.

Patzke, Jürgen, and Emmanuel J Favaloro. "Laboratory Testing for von Willebrand Factor Activity by Glycoprotein Ib Binding Assays (VWF:GPIb)." Methods in molecular biology (Clifton, N.J.) vol. 1646 (2017): 453-460. doi:10.1007/978-1-4939-7196-1_33.

Quinn, Stephen D, and Jenny Higham. "Outcome measures for heavy menstrual bleeding." Women's health (London, England) vol. 12,1 (2016): 21-6. doi:10.2217/whe.15.85.

Ragni, M V et al. "Von Willebrand factor for menorrhagia: a survey and literature review." Haemophilia : the official journal of the World Federation of Hemophilia vol. 22,3 (2016): 397-402. doi:10.1111/hae.12898.

Rimmer, E et al. "Malposition and expulsion of the levonorgestrel intrauterine system among women with inherited bleeding disorders." Haemophilia : the official journal of the World Federation of Hemophilia vol. 19,6 (2013): 933-8. doi:10.1111/hae.12184.

Rodeghiero, F et al. "ISTH/SSC bleeding assessment tool: a standardized questionnaire and a proposal for a new bleeding score for inherited bleeding disorders." Journal of thrombosis and haemostasis : JTH vol. 8,9 (2010): 2063-5. doi:10.1111/j.1538-7836.2010.03975.x.

Stufano, Francesca et al. "Evaluation of a fully automated von Willebrand factor assay panel for the diagnosis of von Willebrand disease." Haemophilia : the official journal of the World Federation of Hemophilia vol. 26,2 (2020): 298-305. doi:10.1111/hae.13929.

Yin et al., Effects of antioxidants on the hydrogen peroxide-mediated oxidation of methionine residues in granulocyte colony-stimulating factor and human parathyroid hormone fragment 13-34, Pharm. Res., 21:2377-83 (2004).

"RVWF In Prophylaxis—Full Text View—ClinicalTrials.gov", Mar. 6, 2018, URL:https://clinicaltrials.gov/ct2/show/NCT02973087.

(56) References Cited

OTHER PUBLICATIONS

Abshire, T. C. "The Role of Prophylaxis in the Management of von Willebrand Disease: Today and Tomorrow." Thrombosis Research, vol. 124 Suppl 1, Nov. 2009, pp. S15-19.

Abshire, T. C., et al. "Prophylaxis in Severe Forms of von Willebrand's Disease: Results from the von Willebrand Disease Prophylaxis Network (VWD PN)." Haemophilia: The Official Journal of the World Federation of Hemophilia, vol. 19, No. 1, Jan. 2013, pp. 76-81.

Abshire, T., et al. "Prophylaxis Escalation in Severe von Willebrand Disease: A Prospective Study from the von Willebrand Disease Prophylaxis Network." Journal of Thrombosis and Haemostasis: JTH, vol. 13, No. 9, Sep. 2015, pp. 1585-1589.

Berntorp, E. "Prophylaxis in von Willebrand Disease." Haemophilia, vol. 14, No. s5, 2008, pp. 47-53.

Berntorp, E., "Prophylaxis and Treatment of Bleeding Complications in von Willebrand Disease Type 3." Seminars in Thrombosis and Hemostasis, vol. 32, No. 6, Sep. 2006, pp. 621-625.

Berntorp, E., et al. "Long-Term Prophylaxis in von Willebrand Disease." Blood Coagulation & Fibrinolysis, vol. 16, Apr. 2005, p. S23.

Brown, J. E., et al. "An Elisa Test for the Binding of von Willebrand Antigen to Collagen." Thrombosis Research, vol. 43, No. 3, Elsevier, Aug. 1986, pp. 303-311.

Cumming, A. M., et al. "Analysis of von Willebrand Factor Multimers Using a Commercially Available Enhanced Chemiluminescence Kit." Journal of Clinical Pathology, vol. 46, No. 5, May 1993, pp. 470-473.

Eikenboom, J. C., et al. "The inheritance and molecular genetics of von Willebrand's disease." Haemophilia : the official journal of the World Federation of Hemophilia vol. 1,2 (1995): 77-90.

Favaloro, E.J. et al., "Laboratory assays for von Willebrand factor: relative contribution to the diagnosis of von Willebrand's disease," Pathology, 1997;29(4):385-91.

Favaloro, E. J. "Collagen Binding Assay for von Willebrand Factor (VWF:CBA): Detection of von Willebrands Disease (VWD), and Discrimination of VWD Subtypes, Depends on Collagen Source." Thrombosis and Haemostasis, vol. 83, No. 1, Jan. 2000, pp. 127-135.

Favaloro, E. J. "Towards Personalised Therapy for von Willebrand Disease: A Future Role for Recombinant Products." Blood Transfusion = Trasfusione Del Sangue, vol. 14, No. 2, 2016, pp. 262-276.

Gill, J. C., et al. "Hemostatic Efficacy, Safety, and Pharmacokinetics of a Recombinant von Willebrand Factor in Severe von Willebrand Disease." Blood, vol. 126, No. 17, American Society of Hematology, Oct. 2015, pp. 2038-2046.

Lankhof, H., et al. "Von Willebrand Factor without the A2 Domain Is Resistant to Proteolysis." Thrombosis and Haemostasis, vol. 77, No. 5, May 1997, pp. 1008-1013.

Leebeek, F. W. G., et al. "Von Willebrand's Disease." The New England journal of medicine vol. 375,21 (2016): 2067-2080.

MacFarlane, D. E., et al. "Letter: A method for assaying von Willebrand factor (ristocetin cofactor)." Thrombosis et diathesis haemorrhagica, vol. 34, No. 1, 1975, pp. 306-308.

Mannucci, P. M., et al. "Pharmacokinetics and Safety of a Novel Recombinant Human von Willebrand Factor Manufactured with a Plasma-Free Method: A Prospective Clinical Trial." Blood, vol. 122, No. 5, Aug. 2013, pp. 648-657.

Mannucci, P. M., et al. "Proteolysis of von Willebrand Factor in Therapeutic Plasma Concentrates." Blood, vol. 83, No. 10, May 1994, pp. 3018-3027.

Mannucci, P. M., et al. "Laboratory Monitoring of Replacement Therapy for Major Surgery in von Willebrand Disease." Haemophilia, vol. 23, No. 2, 2017, pp. 182-187.

Migneault, I., et al. "Glutaraldehyde: Behavior in Aqueous Solution, Reaction with Proteins, and Application to Enzyme Crosslinking." BioTechniques, vol. 37, No. 5, Nov. 2004, pp. 790-796, 798-802.

National Institutes of Health. National Heart, Lung, and Blood Institute. The Diagnosis, Evaluation, and Management of von Willebrand Disease NIH Publication No. 08-5832; Dec. 2007.

Nichols, W. L., et al. "Von Willebrand Disease (VWD): Evidence-Based Diagnosis and Management Guidelines, the National Heart, Lung, and Blood Institute (NHLBI) Expert Panel Report (USA)1." Haemophilia, vol. 14, No. 2, 2008, pp. 171-232.

Piétu, G., et al. "Production in *Escherichia coli* of a Biologically Active Subfragment of von Willebrand Factor Corresponding to the Platelet Glycoprotein Ib, Collagen and Heparin Binding Domains." Biochemical and Biophysical Research Communications, vol. 164, No. 3, Nov. 1989, pp. 1339-1347.

Reininger, A. J. "The Function of Ultra-Large von Willebrand Factor Multimers in High Shear Flow Controlled by ADAMTS13." Hamostaseologie, vol. 35, No. 3, 2015, pp. 225-233.

Sadler, J. E. "Biochemistry and Genetics of von Willebrand Factor." Annual Review of Biochemistry, vol. 67, 1998, pp. 395-424.

Sobieraj, D. M., et al. "Additional Evidence Tables." Venous Thromboembolism Prophylaxis in Orthopedic Surgery [Internet], Agency for Healthcare Research and Quality (US), 2012. www.ncbi.nlm.nih.gov, https://www.ncbi.nlm.nih.gov/books/NBK92309/.

Turecek, P. L., et al. "Development of a Plasma- and Albumin-Free Recombinant von Willebrand Factor." Hamostaseologie, vol. 29 Suppl 1, Oct. 2009, pp. S32-38.

Turecek, P. L., et al. "Structure and Function of a Recombinant von Willebrand Factor Drug Candidate." Seminars in Thrombosis and Hemostasis, vol. 36, No. 5, Jul. 2010, pp. 510-521.

Turecek, P. L., et al. "The Role of Ultralarge Multimers in Recombinant Human von Willebrand Factor—a Review of Physico-and Biochemical Studies and Findings in in Vivo Models and in Humans with von Willebrand Disease." Hamostaseologie, vol. 37, No. S 01, 2017, pp. S15-25.

Veyradier, A., et al. "A Laboratory Phenotype/Genotype Correlation of 1167 French Patients From 670 Families With von Willebrand Disease." Medicine, vol. 95, No. 11, Mar. 2016.

Veyvondi Summary of Product Characteristics. European Medicines Agency. https://www.ema.europa.eu/en/documents/product-information/veyvondi-epar-product-information_en.pdf.

Weiss, H. J., et al. "Quantitative Assay of a Plasma Factor Deficient in von Willebrand's Disease That Is Necessary for Platelet Aggregation. Relationship To Factor VIII Procoagulant Activity and Antigen Content." Journal of Clinical Investigation, vol. 52, No. 11, Nov. 1973, pp. 2708-2716.

Wells, G., et al. "Clinical Review." Safety, Effectiveness, and Cost-Effectiveness of New Oral Anticoagulants Compared with Warfarin in Preventing Stroke and Other Cardiovascular Events in Patients with Atrial Fibrillation [Internet], Canadian Agency for Drugs and Technologies in Health, 2012. www.ncbi.nlm.nih.gov, https://www.ncbi.nlm.nih.gov/books/NBK169813/.

Wen, L. T., et al. "Chemiluminographic Detection of von Willebrand Factor Multimeric Composition." Journal of Clinical Laboratory Analysis, vol. 7, No. 6, 1993, pp. 317-323.

\* cited by examiner

PK, pharmacokinetic.

FIG. 2

Key study inclusion and exclusion criteria

| Inclusion criteria | Exclusion criteria |
| --- | --- |
| Documented diagnosis of severe VWD:<br>    Type 1 VWD (VWF:RCo <20 IU/dL) or<br>    Type 2A (as verified by multimer pattern), type 2B (as diagnosed by genotype), type 2M, or<br>    Type 3 (VWF:Ag ≤3 IU/dL)<br>VWD diagnosis confirmed by genetic testing and multimer analysis, documented in patient history or at screening<br>Patients in the pdVWF switch cohort who have received prophylactic treatment with pdVWF products for ≥12 months prior to screening<br>Patients in the on-demand cohort who are currently receiving on-demand treatment for whom prophylactic treatment is recommended by the investigator<br>Patients in the on-demand cohort who have ≥3 documented spontaneous bleeds (not including menorrhagia) requiring VWF treatment during the previous 12 months | Diagnosed with type 2N VWD, pseudo VWD, or another hereditary or acquired coagulation disorder other than VWD<br>Currently receiving prophylactic treatment with >5 infusions per week<br>Currently receiving prophylactic treatment with a weekly dose >240 IU/kg<br>History or presence of a VWF inhibitor at screening<br>Known hypersensitivity to any of the components of the study drugs, such as to mouse or hamster proteins |
| pdVWF, plasma-derived von Willebrand factor; VWD, von Willebrand disease; VWF, von Willebrand factor; VWF:RCo, von Willebrand factor ristocetin cofactor activity; VWF:Ag, von Willebrand factor antigen. | |

FIG. 3

Example dosing schedules for rVWF prophylaxis

| Schedule | Mon | Tue | Wed | Thu | Fri | Sat | Sun | Mon | Tue | Wed | Thu | Fri | Sat | Sun |
|---|---|---|---|---|---|---|---|---|---|---|---|---|---|---|
| A | ✓ | | | | ✓ | | | ✓ | | | | ✓ | | |
| B | ✓ | | ✓ | | | ✓ | | ✓ | | ✓ | | | ✓ | |

FIG. 4

Main study outcome measures

| Type | Measure |
|---|---|
| Primary | • ABRs for spontaneous BEs (i.e., BEs not related to trauma) during prophylactic treatment with rVWF |
| Secondary | Efficacy<br>• Proportion of patients in the on-demand cohort achieving a reduction of ≥25% in ABR for spontaneous BEs during rVWF prophylaxis relative to their prestudy ABR<br>• Proportion of patients in the switch cohort achieving an ABR for spontaneous BEs during rVWF prophylaxis that is no greater than their prestudy ABR obtained during prophylactic treatment with pdVWF<br>• ABR for spontaneous BEs by bleed location during prophylactic treatment with rVWF<br>• Categorized ABR for spontaneous BEs defined as 0, 1–2, 3–5, or >5 BEs during 12 months of prophylactic treatment with rVWF<br>• Total and average number of rVWF infusions per week during prophylactic treatment<br>• Total weight-adjusted consumption of rVWF during prophylactic treatment |
|  | Safety<br>• Adverse events – incidence, severity, and causality<br>• Thromboembolic events<br>• Hypersensitivity reactions<br>• Development of neutralizing antibodies to VWF and FVIII<br>• Development of total binding antibodies to VWF and FVIII<br>• Development of binding antibodies to Chinese hamster ovary proteins, mouse immunoglobulin G, and rFurin<br>• Clinically significant changes in vital signs and clinical laboratory parameters relative to baseline |
|  | PK and PD parameters<br>• PK and PD parameters (on-demand cohort) and steady-state parameters (on-demand and switch cohorts)<br>  – PK parameters: based on VWF:RCo, VWF:Ag, and VWF collagen-binding capacity activity versus time profiles<br>  – PD parameters: based on FVIII:C, measured by the 1-stage clotting assay) versus time profiles |
| Exploratory | • Assessments of health-related quality of life parameters will be carried out |

ABR, annualized bleeding rate; BE, bleeding episode; FVIII, factor VIII; FVIII:C, FVIII activity; PD, pharmacodynamic; pdVWF, plasma-derived von Willebrand factor; PK, pharmacokinetic; rVWF, recombinant von Willebrand factor; VWF:RCo, von Willebrand factor ristocetin cofactor activity; VWF:Ag, von Willebrand factor antigen.

FIG. 5A

SEQ ID NO:1

```
agctcacagc tattgtggtg ggaaagggag ggtggttggt ggatgtcaca gcttgggctt      60
tatctccccc agcagtgggg actccacagc ccctgggcta cataacagca agacagtccg     120
gagctgtagc agacctgatt gagcctttgc agcagctgag agcatggcct agggtgggcg     180
gcaccattgt ccagcagctg agtttcccag ggaccttgga gatagccgca gccctcattt     240
gcaggggaag atgattcctg ccagatttgc cggggtgctg cttgctctgg ccctcatttt     300
gccagggacc ctttgtgcag aaggaactcg cggcaggtca tccacggccc gatgcagcct     360
tttcggaagt gacttcgtca acacctttga tgggagcatg tacagctttg cgggatactg     420
cagttacctc ctggcagggg gctgccagaa acgctccttc tcgattattg gggacttcca     480
gaatggcaag agagtgagcc tctccgtgta tcttggggaa tttttttgaca tccatttgtt     540
tgtcaatggt accgtgacac aggggaccca aagagtctcc atgccctatg cctccaaagg     600
gctgtatcta gaaactgagg ctgggtacta caagctgtcc ggtgaggcct atggctttgt     660
ggccaggatc gatggcagcg gcaactttca agtcctgctg tcagacagat acttcaacaa     720
gacctgcggg ctgtgtggca acttttaacat ctttgctgaa gatgacttta tgacccaaga     780
agggaccttg acctcggacc cttatgactt tgccaactca tgggctctga gcagtggaga     840
acagtggtgt gaacgggcat ctcctcccag cagctcatgc aacatctcct ctggggaaat     900
gcagaagggc ctgtgggagc agtgccagct tctgaagagc acctcggtgt tgcccgctg      960
ccaccctctg gtggaccccg agccttttgt ggccctgtgt gagaagactt tgtgtgagtg    1020
tgctgggggg ctggagtgcg cctgccctgc cctcctggag tacgcccgga cctgtgccca    1080
ggagggaatg gtgctgtacg gctggaccga ccacagcgcg tgcagcccag tgtgccctgc    1140
tggtatggag tataggcagt gtgtgtcccc ttgcgccagg acctgccaga gctgcacat     1200
caatgaaatg tgtcaggagc gatgcgtgga tggctgcagc tgccctgagg acagctcct    1260
ggatgaaggc ctctgcgtgg agagcaccga gtgtccctgc gtgcattccg aaagcgcta    1320
ccctcccggc acctccctct ctcgagactg caacacctgc atttgccgaa acagccagtg    1380
gatctgcagc aatgaagaat gtccagggga gtgccttgtc acaggtcaat cacacttcaa    1440
gagctttgac aacagatact tcaccttcag tgggatctgc cagtacctgc tggcccggga    1500
ttgccaggac cactccttct ccattgtcat tgagactgtc cagtgtgctg atgaccgcga    1560
cgctgtgtgc acccgctccg tcaccgtccg gctgcctggc tgcacaacga gccttgtgaa    1620
actgaagcat ggggcaggag ttgccatgga tggccaggac gtccagctcc cctcctgaa    1680
aggtgacctc cgcatccagc atacagtgac ggcctccgtg cgcctcagct acggggagga    1740
cctgcagatg gactgggatg ccgcgggag gctgctggtg aagctgtccc cgtctatgc     1800
cgggaagacc tgcggcctgt gtgggaatta caatggcaac cagggcgacg acttccttac    1860
ccctctggg ctggcggagc cccgggtgga ggacttcggg aacgcctgga gctgcacgg     1920
ggactgccag gacctgcaga agcagcacag cgatccctgc gccctcaacc cgcgcatgac    1980
caggttctcc gaggaggcgt gcgcggtcct gacgtccccc acattgcagg cctgccatcg    2040
tgccgtcagc ccgctgccct acctgcggaa ctgccgctac gacgtgtgct cctgctcga    2100
cggccgcgag tgcctgtgcg gcgccctggc cagctatgcc gcggcctgcg cggggagagg    2160
cgtgcgcgtc gcgtggcgcg agccaggccg ctgtgagctg aactgcccga aaggccaggt    2220
gtacctgcag tgcgggaccc cctgcaacct gacctgccgc tctctctctt acccggatga    2280
ggaatgcaat gaggcctgcc tggagggctg cttctgcccc caggctct acatggatga     2340
gagggggac tgcgtgccca aggcccagtg ccctgttac tatgacggtg agatcttcca     2400
gccagaagac atcttctcag accatcacac catgtgctac tgtgaggatg gcttcatgca    2460
ctgtaccatg agtggagtcc ccggaagctt gctgcctgac gctgtcctca gcagtcccct    2520
gtctcatcgc agcaaaagga gcctatcctg tcggccccc atggtcaagc tggtgtgtcc    2580
cgctgacaac ctgcgggctg aagggtcga gtgtaccaaa acgtgccaga actatgacct    2640
ggagtgcatg agcatgggct gtgtctctgg ctgcctctgc cccccgggca tggtccggca    2700
tgagaacaga tgtgtggccc tggaaaggtg tccctgcttc catcagggca aggagtatgc    2760
ccctggagaa acagtgaaga ttggctgcaa cacttgtgtc tgtcgggacc ggaagtggaa    2820
ctgcacagac catgtgtgtg atgccacgtg ctccacgatc ggcatggccc actacctcac    2880
cttcgacggg ctcaaatacc tgttccccgg ggagtgccag tacgttctgg tgcaggatta    2940
ctgcggcagt aaccctggga cctttcggat cctagtgggg aataagggat gcagccaccc    3000
ctcagtgaaa tgcaagaaac gggtcaccat cctggtggag ggaggagaga ttgagctgtt    3060
tgacggggag gtgaatgtga agaggcccat gaaggatgag actcactttg aggtggtgga    3120
gtctggccgg tacatcattc tgctgctggg caaagccctc cgcgtggtct ggaccgcca    3180
cctgagcatc tccgtggtcc tgaagcagac ataccaggag aaagtgtgtg gcctgtgtgg    3240
gaattttgat ggcatccaga caatgacct caccagcagc aacctccaag tggaggaaga    3300
ccctgtggac tttgggaact cctggaaagt gagctcgcag tgtgctgaca ccagaaaagt    3360
gcctctggac tcatcccctg ccacctgcca taacaacatc atgaagcaga cgatggtgga    3420
```

FIG. 5B

```
ttcctcctgt agaatcctta ccagtgacgt cttccaggac tgcaacaagc tggtggaccc    3480
cgagccatat ctggatgtct gcatttacga cacctgctcc tgtgagtcca ttggggactg    3540
cgcctgcttc tgcgacacca ttgctgccta tgcccacgtg tgtgcccagc atggcaaggt    3600
ggtgacctgg aggacggcca cattgtgccc ccagagctgc gaggagagga atctccggga    3660
gaacgggtat gagtgtgagt ggcgctataa cagctgtgca cctgcctgtc aagtcacgtg    3720
tcagcaccct gagccactgg cctgcctgt gcagtgtgtg gagggctgcc atgcccactg    3780
ccctccaggg aaaatcctgg atgagctttt gcagacctgc gttgaccctg aagactgtcc    3840
agtgtgtgag gtggctggcc ggcgttttgc ctcaggaaag aaagtcacct tgaatcccag    3900
tgaccctgag cactgccaga tttgccactg tgatgttgtc aacctcacct gtgaagcctg    3960
ccaggagccg gaggcctgg tggtgcctcc cacagatgcc ccggtgagcc ccaccactct    4020
gtatgtggag gacatctcgg aaccgccgtt gcacgatttc tactgcagca ggctactgga    4080
cctggtcttc ctgctggatg gctcctccag gctgtccgag gctgagtttg aagtgctgaa    4140
ggcctttgtg gtggacatga tggagcggct gcgcatctcc cagaagtggg tccgcgtggc    4200
cgtggtggag taccacgacg gctcccacgc ctacatcggg ctcaaggacc ggaagcgacc    4260
gtcagagctg cggcgcattg ccagccaggt gaagtatgcg ggcagccagg tggcctccac    4320
cagcgaggtc ttgaaataca cactgttcca aatcttcagc aagatcgacc gccctgaagc    4380
ctcccgcatc accctgctcc tgatggccag ccaggagccc aacggatgt cccggaactt    4440
tgtccgctac gtccagggcc tgaagaagaa gaaggtcatt gtgatcccgg tgggcattgg    4500
gcccatgcc aacctcaagc agatccgcct catcgagaag caggcccctg agaacaaggc    4560
cttcgtgctg agcagtgtgg atgagctgga gcagcaaagg gacgagatcg ttagctacct    4620
ctgtgacctt gcccctgaag cccctcctcc tactctgccc ccgacatgg cacaagtcac    4680
tgtgggccg gggctcttgg gggtttcgac cctggggccc aagaggaact ccatggttct    4740
ggatgtggcg ttcgtcctgg aaggatcgga caaaattggt gaagccgact tcaacaggag    4800
caaggagttc atggaggagg tgattcagcg gatggatgtg ggccaggaca gcatccacgt    4860
cacggtgctg cagtactcct acatggtgac tgtggagtac cccttcagcg aggcacagtc    4920
caaaggggac atcctgcagc gggtgcgaga gatccgctac cagggcggca acaggaccaa    4980
cactgggctg gcctgcggt acctctctga ccacagcttc ttggtcagcc agggtgaccg    5040
ggagcaggcg cccaacctgg tctacatggt caccggaaat cctgcctctg atgagatcaa    5100
gaggctgcct ggagacatcc aggtggtgcc cattggagtg ggcccaatg ccaacgtgca    5160
ggagctggag aggattggct ggcccaatgc ccctatcctc atccaggact ttgagacgct    5220
ccccgagag gctcctgacc tggtgctgca gaggtgctgc tccggagagg ggctgcagat    5280
ccccaccctc tcccctgcac ctgactgcag ccagccctg gacgtgatcc ttctcctgga    5340
tggctcctcc agtttcccag cttcttattt tgatgaaatg aagagtttcg ccaaggcttt    5400
catttcaaaa gccaatatag gcctcgtct cactcaggtg tcagtgctgc agtatggaag    5460
catcaccacc attgacgtgc catgaacgt ggtcccggag aaagcccatt tgctgagcct    5520
tgtggacgtc atgcagcggg agggagccc cagccaaatc ggggatgcct tgggcttgc    5580
tgtgcgatac ttgacttcag aaatgcatgg tgccaggccg ggagcctcaa aggcggtggt    5640
catcctggtc acggacgtct ctgtggattc agtggatgca gcagctgatg ccgccaggtc    5700
caacagagtg acagtgttcc ctattggaat tggagatcgc tacgatgcag cccagctacg    5760
gatcttggca ggccagcag gcgactccaa cgtggtgaag ctccagcgaa tcgaagacct    5820
ccctaccatg gtcaccttgg gcaattcctt cctccacaaa ctgtgctctg gatttgttag    5880
gatttgcatg gatgaggatg ggaatgagaa gaggcccggg gacgtctgga ccttgccaga    5940
ccagtgccac accgtgactt gccagccaga tggccagacc ttgctgaaga gtcatcgggt    6000
caactgtgac cgggggctga ggccttcgtg cctaacagc cagtcccctg ttaaagtgga    6060
agagacctgt ggctgccgct ggacctgccc ctgcgtgtgc acaggcagct ccactcggca    6120
catcgtgacc tttgatgggc agaatttcaa gctgactggc agctgttctt atgtcctatt    6180
tcaaaacaag gagcaggacc tggaggtgat tctccataat ggtgcctgca gccctggagc    6240
aaggcagggc tgcatgaaat ccatcgaggt gaagcacagt gccctctccg tcgagctgca    6300
cagtgacatg gaggtgacgg tgaatgggag actggtctct gttccttacg tgggtgggaa    6360
catggaagtc aacgtttatg gtgccatcat gcatgaggtc agattcaatc accttggtca    6420
catcttcaca ttcactccac aaaacaatga gttccaactg cagctcagcc ccaagacttt    6480
tgcttcaaag acgtatggtc tgtgtgggat ctgtgatgag aacggagcca atgacttcat    6540
gctgagggat ggcacagtca ccacagactg gaaaacactt gttcaggaat ggactgtgca    6600
gcggccaggg cagacgtgcc agcccatcct ggaggagcag tgtcttgtcc ccgacagctc    6660
ccactgccag gtcctcctct taccactgtt tgctgaatgc cacaaggtcc tggctccagc    6720
cacattctat gccatctgcc agcaggacag ttgccaccag gagcaagtgt gtgaggtgat    6780
cgcctcttat gcccacctct gtcggaccaa cggggtctgc gttgactgga gacacctga    6840
tttctgtgct atgtcatgcc caccatctct ggtctacaac cactgtgagc atggctgtcc    6900
ccggcactgt gatggcaacg tgagctcctg tgggaccat ccctccgaag gctgtttctg    6960
```

FIG. 5C

```
ccctccagat aaagtcatgt tggaaggcag ctgtgtccct gaagaggcct gcactcagtg    7020
cattggtgag gatggagtcc agcaccagtt cctggaagcc tgggtcccgg accaccagcc    7080
ctgtcagatc tgcacatgcc tcagcgggcg gaaggtcaac tgcacaacgc agccctgccc    7140
cacggccaaa gctcccacgt gtggcctgtg tgaagtagcc cgcctccgcc agaatgcaga    7200
ccagtgctgc cccgagtatg agtgtgtgtg tgacccagtg agctgtgacc tgccccagt     7260
gcctcactgt gaacgtggcc tccagcccac actgaccaac cctggcgagt gcagacccaa    7320
cttcacctgc gcctgcagga aggaggagtg caaaagagtg tccccaccct cctgcccccc    7380
gcaccgtttg cccacccttc ggaagaccca gtgctgtgat gagtatgagt gtgcctgcaa    7440
ctgtgtcaac tccacagtga gctgtccct tgggtacttg gcctcaactg ccaccaatga    7500
ctgtggctgt accacaacca cctgccttcc cgacaaggtg tgtgtccacc gaagcaccat    7560
ctaccctgtg ggccagttct gggaggaggg ctgcgatgtg tgcacctgca ccgacatgga    7620
ggatgccgtg atgggcctcc gcgtggccca gtgctcccag aagccctgtg aggacagctg    7680
tcggtcgggc ttcacttacg ttctgcatga aggcgagtgc tgtggaaggt gcctgccatc    7740
tgcctgtgag gtggtgactg gctcaccgcg gggggactcc cagtcttcct ggaagagtgt    7800
cggctcccag tgggcctccc cggagaaccc ctgcctcatc aatgagtgtg tccgagtgaa    7860
ggaggaggtc tttatacaac aaaggaacgt ctcctgcccc cagctggagg tccctgtctg    7920
cccctcgggc tttcagctga gctgtaagac ctcagcgtgc tgcccaagct gtcgctgtga    7980
gcgcatggag gcctgcatgc tcaatggcac tgtcattggg cccgggaaga ctgtgatgat    8040
cgatgtgtgc acgacctgcc gctgcatggt gcaggtgggg gtcatctctg gattcaagct    8100
ggagtgcagg aagaccacct gcaaccctg ccccctgggt tacaaggaag aaaataacac    8160
aggtgaatgt tgtgggagat gtttgcctac ggcttgcacc attcagctaa gaggaggaca    8220
gatcatgaca ctgaagcgtg atgagacgct ccaggatggc tgtgatactc acttctgcaa    8280
ggtcaatgag agaggagagt acttctggga gaagaggtc acaggctgcc cacccttga     8340
tgaacacaag tgtctggctg agggaggtaa aattatgaaa attccaggca cctgctgtga    8400
cacatgtgag gagcctgagt gcaacgacat cactgccagg ctgcagtatg tcaaggtggg    8460
aagctgtaag tctgaagtag aggtggatat ccactactgc agggcaaat gtgccagcaa    8520
agccatgtac tccattgaca tcaacgatgt gcaggaccag tgctcctgct gctctccgac    8580
acggacggag cccatgcagg tggccctgca ctgcaccaat ggctctgttg tgtaccatga    8640
ggttctcaat gccatggagt gcaaatgctc cccaggaag tgcagcaagt gaggctgctg      8700
cagctgcatg ggtgcctgct gctgctgcc ttggcctgat ggccaggcca gagtgctgcc    8760
agtcctctgc atgttctgct cttgtgccct tctgagccca caataaaggc tgagctctta    8820
tcttgcaaaa ggc                                                       8833
```

FIG. 6A

SEQ ID NO:2

```
Met Ile Pro Ala Arg Phe Ala Gly Val Leu Leu Leu Ile Leu Pro Gly
1               5                   10                  15

Thr Leu Cys Ala Glu Gly Thr Arg Gly Arg Ser Ser Thr Ala Arg Cys
            20                  25                  30

Ser Leu Phe Gly Ser Asp Phe Val Asn Thr Phe Asp Gly Ser Met Tyr
            35                  40                  45

Ser Phe Ala Gly Tyr Cys Ser Tyr Leu Leu Ala Gly Gly Cys Gln Lys
            50                  55                  60

Arg Ser Phe Ser Ile Ile Gly Asp Phe Gln Asn Gly Lys Arg Val Ser
65                  70                  75                  80

Leu Ser Val Tyr Leu Gly Glu Phe Phe Asp Ile His Leu Phe Val Asn
                85                  90                  95

Gly Thr Val Thr Gln Gly Asp Gln Arg Val Ser Met Pro Tyr Ala Ser
            100                 105                 110

Lys Leu Glu Thr Glu Ala Gly Tyr Tyr Lys Leu Ser Gly Glu Ala Tyr
            115                 120                 125

Gly Phe Val Ala Arg Ile Asp Gly Ser Gly Asn Phe Gln Val Leu Leu
            130                 135                 140

Ser Asp Arg Tyr Phe Asn Lys Thr Cys Gly Leu Cys Gly Asn Phe Asn
145                 150                 155                 160

Ile Phe Ala Glu Asp Asp Phe Met Thr Gln Glu Gly Thr Leu Thr Ser
            165                 170                 175

Asp Pro Tyr Asp Phe Ala Asn Ser Trp Ala Leu Ser Ser Gly Glu Gln
            180                 185                 190

Trp Cys Glu Arg Pro Ser Ser Ser Cys Asn Ile Ser Ser Gly Glu Met
            195                 200                 205

Gln Lys Gly Leu Trp Glu Gln Cys Gln Leu Leu Lys Ser Thr Ser Val
            210                 215                 220

Phe Ala Arg Cys His Pro Leu Val Asp Pro Glu Pro Phe Cys Glu Lys
225                 230                 235                 240

Thr Leu Cys Glu Cys Ala Gly Gly Leu Glu Cys Ala Cys Pro Ala Leu
            245                 250                 255

Leu Glu Tyr Ala Arg Thr Cys Ala Gln Glu Gly Met Val Leu Tyr Gly
            260                 265                 270

Trp Thr Asp His Ser Ala Cys Ser Pro Val Cys Pro Ala Gly Met Glu
            275                 280                 285

Tyr Arg Gln Cys Val Ser Pro Cys Ala Arg Thr Cys Gln Ser Leu His
            290                 295                 300
```

FIG. 6B

Ile Asn Glu Met Cys Gln Glu Arg Cys Val Asp Gly Cys Ser Cys Pro
305                  310                 315                      320

Glu Gly Gln Leu Leu Asp Glu Gly Leu Cys Val Glu Ser Thr Glu Cys
                325                 330                 335

Pro Cys Val His Ser Gly Lys Arg Tyr Pro Pro Gly Thr Ser Leu Ser
              340                 345                 350

Arg Asp Cys Asn Thr Cys Ile Cys Arg Asn Ser Gln Trp Ile Cys Ser
            355                 360                 365

Asn Glu Glu Cys Pro Gly Glu Cys Leu Val Thr Gly Gln Ser His Phe
    370                 375                 380

Lys Ser Phe Asp Asn Arg Tyr Phe Thr Phe Ser Gly Ile Cys Gln Tyr
385                 390                 395                      400

Leu Leu Ala Arg Asp Cys Gln Asp His Ser Phe Ser Ile Val Ile Glu
                405                 410                 415

Thr Val Gln Cys Ala Asp Asp Arg Asp Ala Val Cys Thr Arg Ser Val
            420                 425                 430

Thr Val Arg Leu Pro Gly Leu His Asn Ser Leu Val Lys Leu Lys His
            435                 440                 445

Gly Ala Gly Val Ala Met Asp Gly Gln Asp Val Gln Leu Pro Leu Leu
450                 455                 460

Lys Gly Asp Leu Arg Ile Gln His Thr Val Thr Ala Ser Val Arg Leu
465                 470                 475                      480

Ser Tyr Gly Glu Asp Leu Gln Met Asp Trp Asp Gly Arg Gly Arg Leu
                485                 490                 495

Leu Val Lys Leu Ser Pro Val Tyr Ala Gly Lys Thr Cys Gly Leu Cys
            500                 505                 510

Gly Asn Tyr Asn Gly Asn Gln Gly Asp Asp Phe Leu Thr Pro Ser Gly
            515                 520                 525

Leu Ala Glu Pro Arg Val Glu Asp Phe Gly Asn Ala Trp Lys Leu His
        530                 535                 540

Gly Asp Cys Gln Asp Leu Gln Lys Gln His Ser Asp Pro Cys Ala Leu
545                 550                 555                      560

Asn Pro Arg Met Thr Arg Phe Ser Glu Glu Ala Cys Ala Val Leu Thr
                565                 570                 575

Ser Pro Thr Phe Glu Ala Cys His Arg Ala Val Ser Pro Leu Pro Tyr
            580                 585                 590

Leu Arg Asn Cys Arg Tyr Asp Val Cys Ser Cys Ser Asp Gly Arg Glu
            595                 600                 605

FIG. 6C

```
Cys Leu Cys Gly Ser Tyr Ala Ala Ala Cys Ala Gly Arg Gly Val Arg
    610             615             620
Val Ala Trp Arg Glu Pro Gly Arg Cys Glu Leu Asn Cys Pro Lys Gly
625             630             635             640
Gln Val Tyr Leu Gln Cys Gly Thr Pro Cys Asn Leu Thr Cys Arg Ser
            645             650             655
Leu Ser Tyr Pro Asp Glu Glu Cys Asn Glu Ala Cys Leu Glu Gly Cys
            660             665             670
Phe Cys Pro Pro Met Asp Glu Arg Gly Asp Cys Val Pro Lys Ala Gln
        675             680             685
Cys Pro Cys Tyr Tyr Asp Gly Glu Ile Phe Gln Pro Glu Asp Ile Phe
    690             695             700
Ser Asp His His Thr Met Cys Tyr Cys Glu Asp Gly Phe Met His Cys
705             710             715             720
Thr Met Ser Gly Val Pro Gly Ser Leu Leu Pro Asp Ala Val Leu Ser
            725             730             735
Ser Pro Leu Ser His Arg Ser Lys Arg Ser Leu Ser Cys Arg Pro Pro
            740             745             750
Met Val Lys Leu Val Cys Pro Ala Asp Asn Leu Arg Ala Glu Gly Leu
            755             760             765
Glu Cys Thr Lys Thr Cys Gln Asn Tyr Asp Leu Glu Cys Met Ser Met
    770             775             780
Gly Cys Val Ser Gly Cys Leu Cys Pro Pro Gly Met Val Arg His Glu
785             790             795             800
Asn Arg Cys Glu Arg Cys Pro Cys Phe His Gln Gly Lys Glu Tyr Ala
            805             810             815
Pro Gly Glu Thr Val Lys Ile Gly Cys Asn Thr Cys Val Cys Arg Asp
            820             825             830
Arg Lys Trp Asn Cys Thr Asp His Val Cys Asp Ala Thr Cys Ser Thr
            835             840             845
Ile Gly Met Ala His Tyr Leu Thr Phe Asp Gly Leu Lys Tyr Leu Phe
    850             855             860
Pro Gly Glu Cys Gln Tyr Val Leu Val Gln Asp Tyr Cys Gly Ser Asn
865             870             875             880
Pro Gly Thr Phe Arg Ile Leu Val Gly Asn Lys Gly Cys Ser His Pro
            885             890             895
Ser Val Lys Cys Lys Lys Arg Val Thr Ile Leu Val Glu Gly Gly Glu
            900             905             910
```

FIG. 6D

```
Ile Glu Leu Phe Asp Gly Glu Val Asn Val Lys Arg Pro Met Lys Asp
        915                 920                 925

Glu Thr His Phe Glu Val Val Glu Ser Gly Arg Tyr Ile Ile Leu Leu
    930                 935                 940

Leu Gly Lys Ala Leu Ser Val Val Trp Asp Arg His Leu Ser Ile Ser
945                 950                 955                 960

Val Val Leu Lys Gln Thr Tyr Gln Glu Lys Val Cys Gly Leu Cys Gly
            965                 970                 975

Asn Phe Asp Gly Ile Gln Asn Asn Asp Leu Thr Ser Ser Asn Leu Gln
            980                 985                 990

Val Glu Glu Asp Pro Val Asp Phe Gly Asn Ser Trp Lys Val Ser Ser
            995                 1000                1005

Gln Cys Ala Asp Thr Arg Lys Val Pro Leu Asp Ser Ser Pro Ala
    1010                1015                1020

Thr Cys His Asn Asn Ile Met Lys Gln Thr Met Val Asp Ser Ser
    1025                1030                1035

Cys Arg Ile Leu Thr Ser Asp Val Phe Gln Asp Cys Asn Lys Leu
    1040                1045                1050

Val Asp Pro Glu Pro Tyr Leu Asp Val Cys Ile Tyr Asp Thr Cys
    1055                1060                1065

Ser Cys Glu Ser Ile Gly Asp Cys Ala Cys Phe Cys Asp Thr Ile
    1070                1075                1080

Ala Ala Tyr Ala His Val Cys Ala Gln His Gly Lys Val Val Thr
    1085                1090                1095

Trp Arg Thr Ala Thr Leu Cys Pro Gln Ser Cys Glu Glu Arg Asn
    1100                1105                1110

Leu Arg Glu Asn Gly Tyr Glu Cys Glu Trp Arg Tyr Asn Ser Cys
    1115                1120                1125

Ala Pro Ala Cys Gln Val Thr Cys Gln His Pro Glu Pro Leu Ala
    1130                1135                1140

Cys Pro Val Gln Cys Val Glu Gly Cys His Ala His Cys Pro Pro
    1145                1150                1155

Gly Lys Ile Leu Asp Glu Leu Leu Gln Thr Cys Val Asp Pro Glu
    1160                1165                1170

Asp Cys Pro Val Cys Glu Val Ala Gly Arg Arg Phe Ala Ser Gly
    1175                1180                1185

Lys Lys Val Thr Leu Asn Pro Ser Asp Pro Glu His Cys Gln Ile
    1190                1195                1200

Cys His Cys Asp Val Val Asn Leu Thr Cys Glu Ala Cys Gln Glu
    1205                1210                1215
```

FIG. 6E

```
Pro Gly Gly Leu Val Val Pro Pro Thr Asp Ala Pro Val Ser Pro
    1220            1225            1230

Thr Thr Leu Tyr Val Glu Asp Ile Ser Glu Pro Pro Leu His Asp
    1235            1240            1245

Phe Tyr Cys Ser Arg Leu Leu Asp Leu Val Phe Leu Leu Asp Gly
    1250            1255            1260

Ser Ser Arg Leu Ser Glu Ala Glu Phe Glu Val Leu Lys Ala Phe
    1265            1270            1275

Val Val Asp Met Met Glu Arg Leu Arg Ile Ser Gln Lys Trp Val
    1280            1285            1290

Arg Val Ala Val Val Glu Tyr His Asp Gly Ser His Ala Tyr Ile
    1295            1300            1305

Gly Leu Lys Asp Arg Lys Arg Pro Ser Glu Leu Arg Arg Ile Ala
    1310            1315            1320

Ser Gln Val Lys Tyr Ala Gly Ser Gln Val Ala Ser Thr Ser Glu
    1325            1330            1335

Val Leu Lys Tyr Thr Leu Phe Gln Ile Phe Ser Lys Ile Asp Arg
    1340            1345            1350

Pro Glu Ala Ser Arg Ile Thr Leu Leu Leu Met Ala Ser Gln Glu
    1355            1360            1365

Pro Gln Arg Met Ser Arg Asn Phe Val Arg Tyr Val Gln Gly Leu
    1370            1375            1380

Lys Lys Lys Lys Val Ile Val Ile Pro Val Gly Ile Gly Pro His
    1385            1390            1395

Ala Asn Leu Lys Gln Ile Arg Leu Ile Glu Lys Gln Ala Pro Glu
    1400            1405            1410

Asn Lys Ala Phe Val Leu Ser Ser Val Asp Glu Leu Glu Gln Gln
    1415            1420            1425

Arg Asp Glu Ile Val Ser Tyr Leu Cys Asp Leu Ala Pro Glu Ala
    1430            1435            1440

Pro Pro Pro Thr Leu Pro Pro Asp Met Ala Gln Val Thr Val Gly
    1445            1450            1455

Pro Gly Leu Leu Gly Val Ser Thr Leu Gly Pro Lys Arg Asn Ser
    1460            1465            1470

Met Val Leu Asp Val Ala Phe Val Leu Glu Gly Ser Asp Lys Ile
    1475            1480            1485

Gly Glu Ala Asp Phe Asn Arg Ser Lys Glu Phe Met Glu Glu Val
    1490            1495            1500
```

FIG. 6F

Ile Gln Arg Met Asp Val Gly Gln Asp Ser Ile His Val Thr Val
1505                     1510                1515

Leu Gln Tyr Ser Tyr Met Val Thr Val Glu Tyr Pro Phe Ser Glu
1520                     1525                1530

Ala Gln Ser Lys Gly Asp Ile Leu Gln Arg Val Arg Glu Ile Arg
1535                     1540                1545

Tyr Gln Gly Gly Asn Arg Thr Asn Thr Gly Leu Ala Leu Arg Tyr
1550                     1555                1560

Leu Ser Asp His Ser Phe Leu Val Ser Gln Gly Asp Arg Glu Gln
1565                     1570                1575

Ala Pro Asn Leu Val Tyr Met Val Thr Gly Asn Pro Ala Ser Asp
1580                     1585                1590

Glu Ile Lys Arg Leu Pro Gly Asp Ile Gln Val Val Pro Ile Gly
1595                     1600                1605

Val Gly Pro Asn Ala Asn Val Gln Glu Leu Glu Arg Ile Gly Trp
1610                     1615                1620

Pro Asn Ala Pro Ile Leu Ile Gln Asp Phe Glu Thr Leu Pro Arg
1625                     1630                1635

Glu Ala Pro Asp Leu Val Leu Gln Arg Cys Cys Ser Gly Glu Gly
1640                     1645                1650

Leu Gln Ile Pro Thr Leu Ser Pro Ala Pro Asp Cys Ser Gln Pro
1655                     1660                1665

Leu Asp Val Ile Leu Leu Leu Asp Gly Ser Ser Ser Phe Pro Ala
1670                     1675                1680

Ser Tyr Phe Asp Glu Met Lys Ser Phe Ala Lys Ala Phe Ile Ser
1685                     1690                1695

Lys Ala Asn Ile Gly Pro Arg Leu Thr Gln Val Ser Val Leu Gln
1700                     1705                1710

Tyr Gly Ser Ile Thr Thr Ile Asp Val Pro Trp Asn Val Val Pro
1715                     1720                1725

Glu Lys Ala His Leu Leu Ser Leu Val Asp Val Met Gln Arg Glu
1730                     1735                1740

Gly Gly Pro Ser Gln Ile Gly Asp Ala Leu Gly Phe Ala Val Arg
1745                     1750                1755

Tyr Leu Thr Ser Glu Met His Gly Ala Arg Pro Gly Ala Ser Lys
1760                     1765                1770

Ala Val Val Ile Leu Val Thr Asp Val Ser Val Asp Ser Val Asp
1775                     1780                1785

Ala Ala Ala Asp Ala Ala Arg Ser Asn Arg Val Thr Val Phe Pro
1790                     1795                1800

FIG. 6G

```
Ile Gly Ile Gly Asp Arg Tyr Asp Ala Ala Gln Leu Arg Ile Leu
1805            1810            1815

Ala Gly Pro Ala Gly Asp Ser Asn Val Val Lys Leu Gln Arg Ile
1820            1825            1830

Glu Asp Leu Pro Thr Met Val Thr Leu Gly Asn Ser Phe Leu His
1835            1840            1845

Lys Leu Cys Ser Gly Phe Val Arg Ile Cys Met Asp Glu Asp Gly
1850            1855            1860

Asn Glu Lys Arg Pro Gly Asp Val Trp Thr Leu Pro Asp Gln Cys
1865            1870            1875

His Thr Val Thr Cys Gln Pro Asp Gly Gln Thr Leu Leu Lys Ser
1880            1885            1890

His Arg Val Asn Cys Asp Arg Gly Leu Arg Pro Ser Cys Pro Asn
1895            1900            1905

Ser Gln Ser Pro Val Lys Val Glu Glu Thr Cys Gly Cys Arg Trp
1910            1915            1920

Thr Cys Pro Cys Val Cys Thr Gly Ser Ser Thr Arg His Ile Val
1925            1930            1935

Thr Phe Asp Gly Gln Asn Phe Lys Leu Thr Gly Ser Cys Ser Tyr
1940            1945            1950

Val Leu Phe Gln Asn Lys Glu Gln Asp Leu Glu Val Ile Leu His
1955            1960            1965

Asn Gly Ala Cys Ser Pro Gly Ala Arg Gln Gly Cys Met Lys Ser
1970            1975            1980

Ile Glu Val Lys His Ser Ala Leu Ser Val Glu Leu His Ser Asp
1985            1990            1995

Met Glu Val Thr Val Asn Gly Arg Leu Val Ser Val Pro Tyr Val
2000            2005            2010

Gly Gly Asn Met Glu Val Asn Val Tyr Gly Ala Ile Met His Glu
2015            2020            2025

Val Arg Phe Asn His Leu Gly His Ile Phe Thr Phe Thr Pro Gln
2030            2035            2040

Asn Asn Glu Phe Gln Leu Gln Leu Ser Pro Lys Thr Phe Ala Ser
2045            2050            2055

Lys Thr Tyr Gly Leu Cys Gly Ile Cys Asp Glu Asn Gly Ala Asn
2060            2065            2070

Asp Phe Met Leu Arg Asp Gly Thr Val Thr Thr Asp Trp Lys Thr
2075            2080            2085
```

FIG. 6H

```
Leu Val Gln Glu Trp Thr Val Gln Arg Pro Gly Gln Thr Cys Gln
    2090            2095            2100
Pro Glu Gln Cys Leu Val Pro Asp Ser Ser His Cys Gln Val Leu
    2105            2110            2115
Leu Leu Pro Leu Phe Ala Glu Cys His Lys Val Leu Ala Pro Ala
    2120            2125            2130
Thr Phe Tyr Ala Ile Cys Gln Gln Asp Ser Cys His Gln Glu Gln
    2135            2140            2145
Val Cys Glu Val Ile Ala Ser Tyr Ala His Leu Cys Arg Thr Asn
    2150            2155            2160
Gly Val Cys Val Asp Trp Arg Thr Pro Asp Phe Cys Ala Met Ser
    2165            2170            2175
Cys Pro Pro Ser Leu Val Tyr Asn His Cys Glu His Gly Cys Pro
    2180            2185            2190
Arg His Cys Asp Gly Asn Val Ser Ser Cys Gly Asp His Pro Ser
    2195            2200            2205
Glu Gly Cys Phe Cys Pro Pro Asp Lys Val Met Leu Glu Gly Ser
    2210            2215            2220
Cys Val Pro Glu Glu Ala Cys Thr Gln Cys Ile Gly Glu Asp Gly
    2225            2230            2235
Val Gln His Gln Phe Leu Glu Ala Trp Val Pro Asp His Gln Pro
    2240            2245            2250
Cys Gln Ile Cys Thr Cys Leu Ser Gly Arg Lys Val Asn Cys Thr
    2255            2260            2265
Thr Gln Pro Cys Pro Thr Ala Lys Ala Pro Thr Cys Gly Leu Cys
    2270            2275            2280
Glu Val Ala Arg Leu Arg Gln Asn Ala Asp Gln Cys Cys Pro Glu
    2285            2290            2295
Tyr Glu Cys Val Cys Asp Pro Val Ser Cys Asp Leu Pro Pro Val
    2300            2305            2310
Pro His Cys Glu Arg Gly Leu Gln Pro Thr Leu Thr Asn Pro Gly
    2315            2320            2325
Glu Cys Arg Pro Asn Phe Thr Cys Ala Cys Arg Lys Glu Glu Cys
    2330            2335            2340
Lys Arg Val Ser Pro Pro Ser Cys Pro Pro His Arg Leu Pro Thr
    2345            2350            2355
Leu Arg Lys Thr Gln Cys Cys Asp Glu Tyr Glu Cys Ala Cys Asn
    2360            2365            2370
Cys Val Asn Ser Thr Val Ser Cys Pro Leu Gly Tyr Leu Ala Ser
    2375            2380            2385
```

FIG. 6I

```
Thr Ala Thr Asn Asp Cys Gly Cys Thr Thr Thr Cys Leu Pro
    2390            2395            2400

Asp Lys Val Cys Val His Arg Ser Thr Ile Tyr Pro Val Gly Gln
    2405            2410            2415

Phe Trp Glu Glu Gly Cys Asp Val Cys Thr Cys Thr Asp Met Glu
    2420            2425            2430

Asp Ala Val Met Gly Leu Arg Val Ala Gln Cys Ser Gln Lys Pro
    2435            2440            2445

Cys Glu Asp Ser Cys Arg Ser Gly Phe Thr Tyr Val Leu His Glu
    2450            2455            2460

Gly Glu Cys Cys Gly Arg Cys Leu Pro Ser Ala Cys Glu Val Val
    2465            2470            2475

Thr Gly Ser Pro Arg Gly Asp Ser Gln Ser Ser Trp Lys Ser Val
    2480            2485            2490

Gly Ser Gln Trp Glu Asn Pro Cys Leu Ile Asn Glu Cys Val Arg
    2495            2500            2505

Val Lys Glu Glu Val Phe Ile Gln Gln Arg Asn Val Ser Cys Pro
    2510            2515            2520

Gln Leu Glu Val Pro Val Cys Pro Ser Gly Phe Gln Leu Ser Cys
    2525            2530            2535

Lys Thr Ser Ala Cys Cys Pro Ser Cys Arg Cys Glu Arg Met Glu
    2540            2545            2550

Ala Cys Met Leu Asn Gly Thr Val Ile Gly Pro Gly Lys Thr Val
    2555            2560            2565

Met Ile Asp Val Cys Thr Thr Cys Arg Cys Met Val Gln Val Gly
    2570            2575            2580

Val Ile Ser Gly Phe Lys Leu Glu Cys Arg Lys Thr Thr Cys Asn
    2585            2590            2595

Pro Cys Pro Leu Gly Tyr Lys Glu Glu Asn Asn Thr Gly Glu Cys
    2600            2605            2610

Cys Gly Arg Cys Leu Pro Thr Ala Cys Thr Ile Gln Leu Arg Gly
    2615            2620            2625

Gly Gln Ile Met Thr Leu Lys Arg Asp Glu Thr Leu Gln Asp Gly
    2630            2635            2640

Cys Asp Thr His Phe Cys Lys Val Asn Glu Arg Gly Glu Tyr Phe
    2645            2650            2655

Trp Glu Lys Arg Val Thr Gly Cys Pro Pro Phe Asp Glu His Lys
    2660            2665            2670
```

FIG. 6J

```
Cys Leu Ala Glu Gly Gly Lys Ile Met Lys Ile Pro Gly Thr Cys
    2675            2680                2685

Cys Asp Thr Cys Glu Glu Pro Glu Cys Asn Asp Ile Thr Ala Arg
    2690            2695                2700

Leu Gln Tyr Val Lys Val Gly Ser Cys Lys Ser Glu Val Glu Val
    2705            2710                2715

Asp Ile His Tyr Cys Gln Gly Lys Cys Ala Ser Lys Ala Met Tyr
    2720            2725                2730

Ser Ile Asp Ile Asn Asp Val Gln Asp Gln Cys Ser Cys Cys Ser
    2735            2740                2745

Pro Thr Arg Thr Glu Pro Met Gln His Cys Thr Asn Gly Ser Val
    2750            2755                2760

Val Tyr His Glu Val Leu Asn Ala Met Glu Cys Lys Cys Ser Pro
    2765            2770                2775

Arg Lys Cys Ser Lys
    2780
```

FIG. 7A

SEQ ID NO:3

```
Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
            35                  40                  45

Pro Gly Met Val Arg His Glu Asn Arg Cys Val Ala Leu Glu Arg Cys
        50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
            115                 120                 125

Val Leu Val Gln Asp Tyr Cys Gly Ser Asn Pro Gly Thr Phe Arg Ile
        130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
            195                 200                 205

Val Val Trp Asp Arg His Leu Ser Ile Ser Val Val Leu Lys Gln Thr
        210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
            245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
290                 295                 300
```

FIG. 7B

```
Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
            325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
            355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly Leu
465                 470                 475                 480

Val Val Pro Pro Thr Asp Ala Pro Val Ser Pro Thr Thr Leu Tyr Val
            485                 490                 495

Glu Asp Ile Ser Glu Pro Pro Leu His Asp Phe Tyr Cys Ser Arg Leu
            500                 505                 510

Leu Asp Leu Val Phe Leu Leu Asp Gly Ser Ser Arg Leu Ser Glu Ala
        515                 520                 525

Glu Phe Glu Val Leu Lys Ala Phe Val Val Asp Met Met Glu Arg Leu
    530                 535                 540

Arg Ile Ser Gln Lys Trp Val Arg Val Ala Val Val Glu Tyr His Asp
545                 550                 555                 560

Gly Ser His Ala Tyr Ile Gly Leu Lys Asp Arg Lys Arg Pro Ser Glu
            565                 570                 575

Leu Arg Arg Ile Ala Ser Gln Val Lys Tyr Ala Gly Ser Gln Val Ala
            580                 585                 590

Ser Thr Ser Glu Val Leu Lys Tyr Thr Leu Phe Gln Ile Phe Ser Lys
        595                 600                 605

Ile Asp Arg Pro Glu Ala Ser Arg Ile Thr Leu Leu Leu Met Ala Ser
610                 615                 620
```

FIG. 7C

```
Gln Glu Pro Gln Arg Met Ser Arg Asn Phe Val Arg Tyr Val Gln Gly
625             630             635             640

Leu Lys Lys Lys Val Ile Val Ile Pro Val Gly Ile Gly Pro His
        645             650             655

Ala Asn Leu Lys Gln Ile Arg Leu Ile Glu Lys Gln Ala Pro Glu Asn
        660             665             670

Lys Ala Phe Val Leu Ser Ser Val Asp Glu Leu Glu Gln Gln Arg Asp
        675             680             685

Glu Ile Val Ser Tyr Leu Cys Asp Leu Ala Pro Glu Ala Pro Pro Pro
        690             695             700

Thr Leu Pro Pro Asp Met Ala Gln Val Thr Val Gly Pro Gly Leu Leu
705             710             715             720

Gly Val Ser Thr Leu Gly Pro Lys Arg Asn Ser Met Val Leu Asp Val
                725             730             735

Ala Phe Val Leu Glu Gly Ser Asp Lys Ile Gly Glu Ala Asp Phe Asn
                740             745             750

Arg Ser Lys Glu Phe Met Glu Glu Val Ile Gln Arg Met Asp Val Gly
        755             760             765

Gln Asp Ser Ile His Val Thr Val Leu Gln Tyr Ser Tyr Met Val Thr
        770             775             780

Val Glu Tyr Pro Phe Ser Glu Ala Gln Ser Lys Gly Asp Ile Leu Gln
785             790             795             800

Arg Val Arg Glu Ile Arg Tyr Gln Gly Gly Asn Arg Thr Asn Thr Gly
                805             810             815

Leu Ala Leu Arg Tyr Leu Ser Asp His Ser Phe Leu Val Ser Gln Gly
                820             825             830

Asp Arg Glu Gln Ala Pro Asn Leu Val Tyr Met Val Thr Gly Asn Pro
        835             840             845

Ala Ser Asp Glu Ile Lys Arg Leu Pro Gly Asp Ile Gln Val Val Pro
850             855             860

Ile Gly Val Gly Pro Asn Ala Asn Val Gln Glu Leu Glu Arg Ile Gly
865             870             875             880

Trp Pro Asn Ala Pro Ile Leu Ile Gln Asp Phe Glu Thr Leu Pro Arg
                885             890             895

Glu Ala Pro Asp Leu Val Leu Gln Arg Cys Cys Ser Gly Glu Gly Leu
        900             905             910

Gln Ile Pro Thr Leu Ser Pro Ala Pro Asp Cys Ser Gln Pro Leu Asp
        915             920             925
```

FIG. 7D

```
Val Ile Leu Leu Leu Asp Gly Ser Ser Phe Pro Ala Ser Tyr Phe
    930             935             940

Asp Glu Met Lys Ser Phe Ala Lys Ala Phe Ile Ser Lys Ala Asn Ile
945             950             955             960

Gly Pro Arg Leu Thr Gln Val Ser Val Leu Gln Tyr Gly Ser Ile Thr
                965             970             975

Thr Ile Asp Val Pro Trp Asn Val Val Pro Glu Lys Ala His Leu Leu
            980             985             990

Ser Leu Val Asp Val Met Gln Arg Glu Gly Gly Pro Ser Gln Ile Gly
        995             1000            1005

Asp Ala  Leu Gly Phe Ala Val Arg Tyr Leu Thr  Ser Glu Met His
    1010            1015            1020

Gly Ala  Arg Pro Gly Ala Ser  Lys Ala Val Val Ile  Leu Val Thr
    1025            1030            1035

Asp Val  Ser Val Asp Ser Val  Asp Ala Ala Ala Asp  Ala Ala Arg
    1040            1045            1050

Ser Asn  Arg Val Thr Val Phe  Pro Ile Gly Ile Gly  Asp Arg Tyr
    1055            1060            1065

Asp Ala  Ala Gln Leu Arg Ile  Leu Ala Gly Pro Ala  Gly Asp Ser
    1070            1075            1080

Asn Val  Val Lys Leu Gln Arg  Ile Glu Asp Leu Pro  Thr Met Val
    1085            1090            1095

Thr Leu  Gly Asn Ser Phe Leu  His Lys Leu Cys Ser  Gly Phe Val
    1100            1105            1110

Arg Ile  Cys Met Asp Glu Asp  Gly Asn Glu Lys Arg  Pro Gly Asp
    1115            1120            1125

Val Trp  Thr Leu Pro Asp Gln  Cys His Thr Val Thr  Cys Gln Pro
    1130            1135            1140

Asp Gly  Gln Thr Leu Leu Lys  Ser His Arg Val Asn  Cys Asp Arg
    1145            1150            1155

Gly Leu  Arg Pro Ser Cys Pro  Asn Ser Gln Ser Pro  Val Lys Val
    1160            1165            1170

Glu Glu  Thr Cys Gly Cys Arg  Trp Thr Cys Pro Cys  Val Cys Thr
    1175            1180            1185

Gly Ser  Ser Thr Arg His Ile  Val Thr Phe Asp Gly  Gln Asn Phe
    1190            1195            1200

Lys Leu  Thr Gly Ser Cys Ser  Tyr Val Leu Phe Gln  Asn Lys Glu
    1205            1210            1215
```

FIG. 7E

```
Gln Asp Leu Glu Val Ile Leu His Asn Gly Ala Cys Ser Pro Gly
1220                1225                1230

Ala Arg Gln Gly Cys Met Lys Ser Ile Glu Val Lys His Ser Ala
1235                1240                1245

Leu Ser Val Glu Leu His Ser Asp Met Glu Val Thr Val Asn Gly
1250                1255                1260

Arg Leu Val Ser Val Pro Tyr Val Gly Gly Asn Met Glu Val Asn
1265                1270                1275

Val Tyr Gly Ala Ile Met His Glu Val Arg Phe Asn His Leu Gly
1280                1285                1290

His Ile Phe Thr Phe Thr Pro Gln Asn Asn Glu Phe Gln Leu Gln
1295                1300                1305

Leu Ser Pro Lys Thr Phe Ala Ser Lys Thr Tyr Gly Leu Cys Gly
1310                1315                1320

Ile Cys Asp Glu Asn Gly Ala Asn Asp Phe Met Leu Arg Asp Gly
1325                1330                1335

Thr Val Thr Thr Asp Trp Lys Thr Leu Val Gln Glu Trp Thr Val
1340                1345                1350

Gln Arg Pro Gly Gln Thr Cys Gln Pro Ile Leu Glu Glu Gln Cys
1355                1360                1365

Leu Val Pro Asp Ser Ser His Cys Gln Val Leu Leu Leu Pro Leu
1370                1375                1380

Phe Ala Glu Cys His Lys Val Leu Ala Pro Ala Thr Phe Tyr Ala
1385                1390                1395

Ile Cys Gln Gln Asp Ser Cys His Gln Glu Gln Val Cys Glu Val
1400                1405                1410

Ile Ala Ser Tyr Ala His Leu Cys Arg Thr Asn Gly Val Cys Val
1415                1420                1425

Asp Trp Arg Thr Pro Asp Phe Cys Ala Met Ser Cys Pro Pro Ser
1430                1435                1440

Leu Val Tyr Asn His Cys Glu His Gly Cys Pro Arg His Cys Asp
1445                1450                1455

Gly Asn Val Ser Ser Cys Gly Asp His Pro Ser Glu Gly Cys Phe
1460                1465                1470

Cys Pro Pro Asp Lys Val Met Leu Glu Gly Ser Cys Val Pro Glu
1475                1480                1485

Glu Ala Cys Thr Gln Cys Ile Gly Glu Asp Gly Val Gln His Gln
1490                1495                1500

Phe Leu Glu Ala Trp Val Pro Asp His Gln Pro Cys Gln Ile Cys
1505                1510                1515
```

FIG. 7F

Thr Cys Leu Ser Gly Arg Lys Val Asn Cys Thr Thr Gln Pro Cys
1520                1525                1530

Pro Thr Ala Lys Ala Pro Thr Cys Gly Leu Cys Glu Val Ala Arg
1535                1540                1545

Leu Arg Gln Asn Ala Asp Gln Cys Cys Pro Glu Tyr Glu Cys Val
1550                1555                1560

Cys Asp Pro Val Ser Cys Asp Leu Pro Pro Val Pro His Cys Glu
1565                1570                1575

Arg Gly Leu Gln Pro Thr Leu Thr Asn Pro Gly Glu Cys Arg Pro
1580                1585                1590

Asn Phe Thr Cys Ala Cys Arg Lys Glu Glu Cys Lys Arg Val Ser
1595                1600                1605

Pro Pro Ser Cys Pro Pro His Arg Leu Pro Thr Leu Arg Lys Thr
1610                1615                1620

Gln Cys Cys Asp Glu Tyr Glu Cys Ala Cys Asn Cys Val Asn Ser
1625                1630                1635

Thr Val Ser Cys Pro Leu Gly Tyr Leu Ala Ser Thr Ala Thr Asn
1640                1645                1650

Asp Cys Gly Cys Thr Thr Thr Thr Cys Leu Pro Asp Lys Val Cys
1655                1660                1665

Val His Arg Ser Thr Ile Tyr Pro Val Gly Gln Phe Trp Glu Glu
1670                1675                1680

Gly Cys Asp Val Cys Thr Cys Thr Asp Met Glu Asp Ala Val Met
1685                1690                1695

Gly Leu Arg Val Ala Gln Cys Ser Gln Lys Pro Cys Glu Asp Ser
1700                1705                1710

Cys Arg Ser Gly Phe Thr Tyr Val Leu His Glu Gly Glu Cys Cys
1715                1720                1725

Gly Arg Cys Leu Pro Ser Ala Cys Glu Val Val Thr Gly Ser Pro
1730                1735                1740

Arg Gly Asp Ser Gln Ser Ser Trp Lys Ser Val Gly Ser Gln Trp
1745                1750                1755

Ala Ser Pro Glu Asn Pro Cys Leu Ile Asn Glu Cys Val Arg Val
1760                1765                1770

Lys Glu Glu Val Phe Ile Gln Gln Arg Asn Val Ser Cys Pro Gln
1775                1780                1785

Leu Glu Val Pro Val Cys Pro Ser Gly Phe Gln Leu Ser Cys Lys
1790                1795                1800

FIG. 7G

Thr Ser Ala Cys Cys Pro Ser Cys Arg Cys Glu Arg Met Glu Ala
1805                1810                1815

Cys Met Leu Asn Gly Thr Val Ile Gly Pro Gly Lys Thr Val Met
1820                1825                1830

Ile Asp Val Cys Thr Thr Cys Arg Cys Met Val Gln Val Gly Val
1835                1840                1845

Ile Ser Gly Phe Lys Leu Glu Cys Arg Lys Thr Thr Cys Asn Pro
1850                1855                1860

Cys Pro Leu Gly Tyr Lys Glu Glu Asn Asn Thr Gly Glu Cys Cys
1865                1870                1875

Gly Arg Cys Leu Pro Thr Ala Cys Thr Ile Gln Leu Arg Gly Gly
1880                1885                1890

Gln Ile Met Thr Leu Lys Arg Asp Glu Thr Leu Gln Asp Gly Cys
1895                1900                1905

Asp Thr His Phe Cys Lys Val Asn Glu Arg Gly Glu Tyr Phe Trp
1910                1915                1920

Glu Lys Arg Val Thr Gly Cys Pro Pro Phe Asp Glu His Lys Cys
1925                1930                1935

Leu Ala Glu Gly Gly Lys Ile Met Lys Ile Pro Gly Thr Cys Cys
1940                1945                1950

Asp Thr Cys Glu Glu Pro Glu Cys Asn Asp Ile Thr Ala Arg Leu
1955                1960                1965

Gln Tyr Val Lys Val Gly Ser Cys Lys Ser Glu Val Glu Val Asp
1970                1975                1980

Ile His Tyr Cys Gln Gly Lys Cys Ala Ser Lys Ala Met Tyr Ser
1985                1990                1995

Ile Asp Ile Asn Asp Val Gln Asp Gln Cys Ser Cys Cys Ser Pro
2000                2005                2010

Thr Arg Thr Glu Pro Met Gln Val Ala Leu His Cys Thr Asn Gly
2015                2020                2025

Ser Val Val Tyr His Glu Val Leu Asn Ala Met Glu Cys Lys Cys
2030                2035                2040

Ser Pro Arg Lys Cys Ser Lys
2045                2050

```
                         SEQUENCE LISTING

<160> NUMBER OF SEQ ID NOS: 3

<210> SEQ ID NO 1
<211> LENGTH: 8833
<212> TYPE: DNA
<213> ORGANISM: Artificial Sequence
<220> FEATURE:
<223> OTHER INFORMATION: prepro-VWF

<400> SEQUENCE: 1
agctcacagc tattgtggtg ggaaagggag ggtggttggt ggatgtcaca gcttgggctt      60
tatctccccc agcagtgggg actccacagc ccctgggcta cataacagca agacagtccg     120
gagctgtagc agacctgatt gagcctttgc agcagctgag agcatggcct agggtgggcg     180
gcaccattgt ccagcagctg agtttcccag ggaccttgga gatagccgca gccctcattt     240
gcaggggaag atgattcctg ccagatttgc cggggtgctg cttgctctgg ccctcatttt     300
gccagggacc ctttgtgcag aaggaactcg cggcaggtca tccacggccc gatgcagcct     360
tttcggaagt gacttcgtca acacctttga tgggagcatg tacagctttg cgggatactg     420
cagttacctc ctggcagggg gctgccagaa acgctccttc tcgattattg gggacttcca     480
gaatggcaag agagtgagcc tctccgtgta tcttgggaa ttttttgaca tccatttgtt     540
tgtcaatggt accgtgacac aggggggacca aagagtctcc atgccctatg cctccaaagg     600
gctgtatcta gaaactgagg ctgggtacta caagctgtcc ggtgaggcct atggctttgt     660
ggccaggatc gatggcagcg gcaactttca agtcctgctg tcagacagat acttcaacaa     720
gacctgcggg ctgtgtggca ctttaacat ctttgctgaa gatgacttta tgacccaaga     780
agggaccttg acctcggacc cttatgactt tgccaactca tgggctctga gcagtggaga     840
acagtggtgt gaacgggcat ctcctcccag cagctcatgc aacatctcct ctgggggaaat     900 gcagaaggc ctgtgggagc agtgccagct tctgaagagc acctcggtgt ttgcccgctg     960
ccaccctctg gtggacccccg agccttttgt ggccctgtgt gagaagactt tgtgtgagtg    1020
tgctgggggg ctggagtgcg cctgccctgc cctcctggag tacgcccgga cctgtgccca    1080
ggagggaatg gtgctgtacg gctggaccga ccacagcgcg tgcagcccag tgtgccctgc    1140
tggtatggag tataggcagt gtgtgtcccc ttgcgccagg acctgccaga gcctgcacat    1200
caatgaaatg tgtcaggagc gatgcgtgga tggctgcagc tgccctgagg acagctcct    1260 ggatgaaggc ctctgcgtgg agagcaccga gtgtccctgc gtgcattccg aaagcgcta    1320 ccctcccggc acctccctct ctcgagactg caacacctgc atttgccgaa acagccagtg    1380
gatctgcagc aatgaagaat gtccagggga gtgccttgtc acaggtcaat cacacttcaa    1440
gagctttgac aacagatact tcaccttcag tgggatctgc cagtacctgc tggcccggga    1500
ttgccaggac cactcctcct ccattgtcat tgagactgtc cagtgtgctg atgaccgcga    1560
cgctgtgtgc acccgctccg tcaccgtccg gctgcctggc ctgcacaaca gccttgtgaa    1620
actgaagcat ggggcaggag ttgccatgga tggccaggac gtccagctcc cctcctgaa    1680 aggtgacctc cgcatccagc atacagtgac ggcctccgtg cgcctcagct acgggaggag    1740
cctgcagatg gactgggatg gccgcgggag gctgctggtg aagctgtccc ccgtctatgc    1800
```

```
cgggaagacc tgcggcctgt gtgggaatta caatggcaac cagggcgacg acttccttac    1860
cccctctggg ctggcggagc cccgggtgga ggacttcggg aacgcctgga agctgcacgg    1920
ggactgccag gacctgcaga agcagcacag cgatccctgc gccctcaacc cgcgcatgac    1980
caggttctcc gaggaggcgt gcgcggtcct gacgtccccc acattcgagg cctgccatcg    2040
tgccgtcagc ccgctgccct acctgcggaa ctgccgctac gacgtgtgct cctgctcgga    2100
cggccgcgag tgcctgtgcg gcgccctggc cagctatgcc gcggcctgcg cggggagagg    2160
cgtgcgcgtc gcgtggcgcg agccaggccg ctgtgagctg aactgcccga aaggccaggt    2220
gtacctgcag tgcgggaccc cctgcaacct gacctgccgc tctctctctt acccggatga    2280
ggaatgcaat gaggcctgcc tggagggctg cttctgcccc cagggctctc catggatga    2340
gaggggggac tgcgtgccca aggcccagtg cccctgttac tatgacggtg agatcttcca    2400
gccagaagac atcttctcag accatcacac catgtgctac tgtgaggatg gcttcatgca    2460
ctgtaccatg agtggagtcc ccggaagctt gctgcctgac gctgtcctca gcagtccccct    2520
gtctcatcgc agcaaaagga gcctatcctg tcggcccccc atggtcaagc tggtgtgtcc    2580
cgctgacaac ctgcgggctg aagggctcga gtgtaccaaa acgtgccaga actatgacct    2640
ggagtgcatg agcatgggct gtgtctctgg ctgcctctgc cccccgggca tggtccggca    2700
tgagaacaga tgtgtggccc tggaaaggtg tccctgcttc catcagggca aggagtatgc    2760
ccctggagaa acagtgaaga ttggctgcaa cacttgtgtc tgtcgggacc ggaagtggaa    2820
ctgcacagac catgtgtgtg atgccacgtg ctccacgatc ggcatggccc actacctcac    2880
cttcgacggg ctcaaatacc tgttccccgg ggagtgccag tacgttctgg tgcaggatta    2940
ctgcggcagt aaccctggga ccttcggat cctagtgggg aataagggat gcagccaccc    3000
ctcagtgaaa tgcaagaaac gggtcaccat cctggtggag ggaggagaga ttgagctgtt    3060
tgacggggag gtgaatgtga agaggcccat gaaggatgag actcactttg aggtggtgga    3120
gtctggccgg tacatcattc tgctgctggg caaagccctc tccgtggtct gggaccgcca    3180
cctgagcatc tccgtggtcc tgaagcagac ataccaggag aaagtgtgtg gcctgtgtgg    3240
gaattttgat ggcatccaga caatgacct caccagcagc aacctccaag tggaggaaga    3300
ccctgtggac tttgggaact cctggaaagt gagctcgcag tgtgctgaca ccagaaaagt    3360
gcctctggac tcatcccctg ccacctgcca taacaacatc atgaagcaga cgatggtgga    3420
ttcctcctgt agaatcctta ccagtgacgt cttccaggac tgcaacaagc tggtggaccc    3480
cgagccatat ctggatgtct gcatttacga cacctgctcc tgtgagtcca ttggggactg    3540
cgcctgcttc tgcgacacca ttgctgccta tgcccacgtg tgtgcccagc atggcaaggt    3600
ggtgacctgg aggacggcca cattgtgccc ccagagctgc gaggagagga atctccggga    3660
gaacgggtat gagtgtgagt ggcgctataa cagctgtgca cctgcctgtc aagtcacgtg    3720
tcagcaccct gagccactgg cctgcccctgt gcagtgtgtg gagggctgcc atgcccactg    3780
ccctccaggg aaaatcctgg atgagctttt gcagacctgc gttgaccctg aagactgtcc    3840
agtgtgtgag gtggctggcc ggcgttttgc ctcaggaaag aaagtcacct tgaatcccag    3900
tgaccctgag cactgccaga tttgccactg tgatgttgtc aacctcacct gtgaagcctg    3960
ccaggagccg ggaggcctgg tggtgcctcc cacagatgcc ccggtgagcc ccaccactct    4020
gtatgtggag gacatctcgg aaccgccgtt gcacgatttc tactgcagca ggctactgga    4080
cctggtcttc ctgctggatg gctcctccag gctgtccgag gctgagtttg aagtgctgaa    4140
ggcctttgtg gtggacatga tggagcggct gcgcatctcc cagaagtggg tccgcgtggc    4200
```

```
cgtggtggag taccacgacg gctcccacgc ctacatcggg ctcaaggacc ggaagcgacc    4260
gtcagagctg cggcgcattg ccagccaggt gaagtatgcg ggcagccagg tggcctccac    4320
cagcgaggtc ttgaaataca cactgttcca aatcttcagc aagatcgacc gccctgaagc    4380
ctcccgcatc accctgctcc tgatggccag ccaggagccc aacggatgt cccggaactt    4440 tgtccgctac gtccagggcc tgaagaagaa aaggtcatt gtgatcccgg tgggcattgg    4500
gccccatgcc aacctcaagc agatccgcct catcgagaag caggccctg agaacaaggc    4560 cttcgtgctg agcagtgtgg atgagctgga gcagcaaagg gacgagatcg ttagctacct    4620
ctgtgacctt gccctgaag cccctcctcc tactctgccc cccgacatgg cacaagtcac    4680
tgtgggcccg gggctcttgg gggtttcgac cctggggccc aagaggaact ccatggttct    4740
ggatgtggcg ttcgtcctgg aaggatcgga caaaattggt gaagccgact caacaggag    4800 caaggagttc atggaggagg tgattcagcg gatggatgtg ggccaggaca gcatccacgt    4860
cacggtgctg cagtactcct acatggtgac tgtggagtac cccttcagcg aggcacagtc    4920
caaaggggac atcctgcagc gggtgcgaga gatccgctac cagggcggca acaggaccaa    4980
cactgggctg gccctgcggt acctctctga ccacagcttc ttggtcagcc agggtgaccg    5040
ggagcaggcg cccaacctgg tctacatggt caccggaaat cctgcctctg atgagatcaa    5100
gaggctgcct ggagacatcc aggtggtgcc cattggagtg ggccctaatg ccaacgtgca    5160
ggagctggag aggattggct ggcccaatgc ccctatcctc atccaggact tgagacgct    5220 cccccgagag gctcctgacc tggtgctgca gaggtgctgc tccggagagg ggctgcagat    5280 ccccacccctc tcccctgcac ctgactgcag ccagcccctg gacgtgatcc ttctcctgga    5340
tggctcctcc agtttcccag cttcttattt tgatgaaatg aagagtttcg ccaaggcttt    5400
catttcaaaa gccaatatag ggcctcgtct cactcaggtg tcagtgctgc agtatggaag    5460
catcaccacc attgacgtgc catggaacgt ggtcccggag aaagcccatt tgctgagcct    5520
tgtggacgtc atgcagcggg agggaggccc cagccaaatc ggggatgcct tgggctttgc    5580
tgtgcgatac ttgacttcag aaatgcatgg tgccaggccg ggagcctcaa aggcggtggt    5640
catcctggtc acgacgtct ctgtggattc agtggatgca gcagctgatg ccgccaggtc    5700
caacagagtg acagtgttcc ctattggaat tggagatcgc tacgatgcag cccagctacg    5760
gatcttggca ggcccagcag gcgactccaa cgtggtgaag ctccagcgaa tcgaagacct    5820
ccctaccatg gtcaccttgg gcaattcctt cctccacaaa ctgtgctctg gatttgttag    5880
gatttgcatg gatgaggatg ggaatgagaa gaggcccggg gacgtctgga ccttgccaga    5940
ccagtgccac accgtgactt gccagccaga tggccagacc ttgctgaaga gtcatcgggt    6000
caactgtgac cgggggctga ggccttcgtg ccctaacagc cagtcccctg ttaaagtgga    6060
agagacctgt ggctgccgct ggacctgccc ctgcgtgtgc acaggcagct ccactcggca    6120
catcgtgacc tttgatgggc agaatttcaa gctgactggc agctgttctt atgtcctatt    6180
tcaaaacaag gagcaggacc tggaggtgat tctccataat ggtgcctgca gccctggagc    6240
aaggcagggc tgcatgaaat ccatcgaggt gaagcacagt gccctctccg tcgagctgca    6300
cagtgacatg gaggtgacgg tgaatgggag actggtctct gttccttacg tgggtgggaa    6360
catggaagtc aacgtttatg gtgccatcat gcatgaggtc agattcaatc accttggtca    6420
catcttcaca ttcactccac aaaacaatga gttccaactg cagctcagcc ccaagacttt    6480
tgcttcaaag acgtatggtc tgtgtgggat ctgtgatgag aacggagcca atgacttcat    6540
```

```
gctgagggat ggcacagtca ccacagactg gaaaacactt gttcaggaat ggactgtgca    6600
gcggccaggg cagacgtgcc agcccatcct ggaggagcag tgtcttgtcc ccgacagctc    6660
ccactgccag gtcctcctct taccactgtt tgctgaatgc cacaaggtcc tggctccagc    6720
cacattctat gccatctgcc agcaggacag ttgccaccag gagcaagtgt gtgaggtgat    6780
cgcctcttat gcccacctct gtcggaccaa cggggtctgc gttgactgga ggacacctga    6840
tttctgtgct atgtcatgcc caccatctct ggtctacaac cactgtgagc atggctgtcc    6900
ccggcactgt gatggcaacg tgagctcctg tggggaccat ccctccgaag gctgtttctg    6960
ccctccagat aaagtcatgt tggaaggcag ctgtgtccct gaagaggcct gcactcagtg    7020
cattggtgag gatggagtcc agcaccagtt cctggaagcc tgggtcccgg accaccagcc    7080
ctgtcagatc tgcacatgcc tcagcgggcg gaaggtcaac tgcacaacgc agccctgccc    7140
cacggccaaa gctcccacgt gtggcctgtg tgaagtagcc cgcctccgcc agaatgcaga    7200
ccagtgctgc cccgagtatg agtgtgtgtg tgacccagtg agctgtgacc tgccccagt     7260
gcctcactgt gaacgtggcc tccagcccac actgaccaac cctggcgagt gcagacccaa    7320
cttcacctgc gcctgcagga aggaggagtg caaaagagtg tccccaccct cctgccccc     7380
gcaccgtttg cccaccttc ggaagaccca gtgctgtgat gagtatgagt gtgcctgcaa     7440
ctgtgtcaac tccacagtga gctgtccct tgggtacttg gcctcaactg ccaccaatga    7500
ctgtggctgt accacaacca cctgccttcc cgacaaggtg tgtgtccacc gaagcaccat    7560
ctaccctgtg ggccagttct gggaggaggg ctgcgatgtg tgcacctgca ccgacatgga    7620
ggatgccgtg atgggcctcc gcgtggccca gtgctcccag aagccctgtg aggacagctg    7680
tcggtcgggc ttcacttacg ttctgcatga aggcgagtgc tgtggaaggt gcctgccatc    7740
tgcctgtgag gtggtgactg gctcaccgcg ggggactcc cagtcttcct ggaagagtgt     7800
cggctcccag tgggcctccc cggagaaccc ctgcctcatc aatgagtgtg tccgagtgaa    7860
ggaggaggtc tttatacaac aaaggaacgt ctcctgcccc cagctggagg tccctgtctg    7920
cccctcgggc tttcagctga ctgtaagac ctcagcgtgc tgcccaagct gtcgctgtga     7980
gcgcatggag gcctgcatgc tcaatggcac tgtcattggg cccgggaaga ctgtgatgat    8040
cgatgtgtgc acgacctgcc gctgcatggt gcaggtgggg gtcatctctg gattcaagct    8100
ggagtgcagg aagaccacct gcaacccctg cccctgggt tacaaggaag aaaataacac     8160
aggtgaatgt tgtgggagat gttttgcctac ggcttgcacc attcagctaa gaggaggaca    8220
gatcatgaca ctgaagcgtg atgagacgct ccaggatggc tgtgatactc acttctgcaa    8280
ggtcaatgag agaggagagt acttctggga gaagagggtc acaggctgcc cacccttttga    8340
tgaacacaag tgtctggctg agggaggtaa aattatgaaa attccaggca cctgctgtga    8400
cacatgtgag gagcctgagt gcaacgacat cactgccagg ctgcagtatg tcaaggtggg    8460
aagctgtaag tctgaagtag aggtggatat ccactactgc cagggcaaat gtgccagcaa    8520
agccatgtac tccattgaca tcaacgatgt gcaggaccag tgctcctgct gctctccgac    8580
acggacggag cccatgcagg tggccctgca ctgcaccaat ggctctgttg tgtaccatga    8640
ggttctcaat gccatggagt gcaaatgctc ccccaggaag tgcagcaagt gaggctgctg    8700
cagctgcatg ggtgcctgct gctgcctgcc ttggcctgat ggccaggcca gagtgctgcc    8760
agtcctctgc atgttctgct cttgtgccct tctgagccca caataaaggc tgagctctta    8820
tcttgcaaaa ggc                                                      8833
```

```
<210> SEQ ID NO 2
<211> LENGTH: 2783
<212> TYPE: PRT
<213> ORGANISM: Artificial Sequence
<220> FEATURE:
<223> OTHER INFORMATION: prepro-VWF

<400> SEQUENCE: 2
```

| | | | | | | | | | | | | | | |
|---|---|---|---|---|---|---|---|---|---|---|---|---|---|---|
| Met | Ile | Pro | Ala | Arg | Phe | Ala | Gly | Val | Leu | Leu | Ile | Leu | Pro | Gly |
| 1 | | | | 5 | | | | | 10 | | | | | 15 |
| Thr | Leu | Cys | Ala | Glu | Gly | Thr | Arg | Gly | Arg | Ser | Ser | Thr | Ala | Arg | Cys |
| | | | 20 | | | | | 25 | | | | | 30 | | |
| Ser | Leu | Phe | Gly | Ser | Asp | Phe | Val | Asn | Thr | Phe | Asp | Gly | Ser | Met | Tyr |
| | | 35 | | | | | 40 | | | | | 45 | | | |
| Ser | Phe | Ala | Gly | Tyr | Cys | Ser | Tyr | Leu | Leu | Ala | Gly | Gly | Cys | Gln | Lys |
| | 50 | | | | | 55 | | | | | 60 | | | | |
| Arg | Ser | Phe | Ser | Ile | Ile | Gly | Asp | Phe | Gln | Asn | Gly | Lys | Arg | Val | Ser |
| 65 | | | | | 70 | | | | | 75 | | | | | 80 |
| Leu | Ser | Val | Tyr | Leu | Gly | Glu | Phe | Phe | Asp | Ile | His | Leu | Phe | Val | Asn |
| | | | | 85 | | | | | 90 | | | | | 95 | |
| Gly | Thr | Val | Thr | Gln | Gly | Asp | Gln | Arg | Val | Ser | Met | Pro | Tyr | Ala | Ser |
| | | | 100 | | | | | 105 | | | | | 110 | | |
| Lys | Leu | Glu | Thr | Glu | Ala | Gly | Tyr | Tyr | Lys | Leu | Ser | Gly | Glu | Ala | Tyr |
| | | 115 | | | | | 120 | | | | | 125 | | | |
| Gly | Phe | Val | Ala | Arg | Ile | Asp | Gly | Ser | Gly | Asn | Phe | Gln | Val | Leu | Leu |
| | 130 | | | | | 135 | | | | | 140 | | | | |
| Ser | Asp | Arg | Tyr | Phe | Asn | Lys | Thr | Cys | Gly | Leu | Cys | Gly | Asn | Phe | Asn |
| 145 | | | | | 150 | | | | | 155 | | | | | 160 |
| Ile | Phe | Ala | Glu | Asp | Asp | Phe | Met | Thr | Gln | Glu | Gly | Thr | Leu | Thr | Ser |
| | | | | 165 | | | | | 170 | | | | | 175 | |
| Asp | Pro | Tyr | Asp | Phe | Ala | Asn | Ser | Trp | Ala | Leu | Ser | Ser | Gly | Glu | Gln |
| | | | 180 | | | | | 185 | | | | | 190 | | |
| Trp | Cys | Glu | Arg | Pro | Ser | Ser | Cys | Asn | Ile | Ser | Ser | Gly | Glu | Met |
| | | 195 | | | | | 200 | | | | | 205 | | | |
| Gln | Lys | Gly | Leu | Trp | Glu | Gln | Cys | Gln | Leu | Leu | Lys | Ser | Thr | Ser | Val |
| | 210 | | | | | 215 | | | | | 220 | | | | |
| Phe | Ala | Arg | Cys | His | Pro | Leu | Val | Asp | Pro | Glu | Pro | Phe | Cys | Glu | Lys |
| 225 | | | | | 230 | | | | | 235 | | | | | 240 |
| Thr | Leu | Cys | Glu | Cys | Ala | Gly | Gly | Leu | Glu | Cys | Ala | Cys | Pro | Ala | Leu |
| | | | | 245 | | | | | 250 | | | | | 255 | |
| Leu | Glu | Tyr | Ala | Arg | Thr | Cys | Ala | Gln | Glu | Gly | Met | Val | Leu | Tyr | Gly |
| | | | 260 | | | | | 265 | | | | | 270 | | |
| Trp | Thr | Asp | His | Ser | Ala | Cys | Ser | Pro | Val | Cys | Pro | Ala | Gly | Met | Glu |
| | | 275 | | | | | 280 | | | | | 285 | | | |
| Tyr | Arg | Gln | Cys | Val | Ser | Pro | Cys | Ala | Arg | Thr | Cys | Gln | Ser | Leu | His |
| | 290 | | | | | 295 | | | | | 300 | | | | |
| Ile | Asn | Glu | Met | Cys | Gln | Glu | Arg | Cys | Val | Asp | Gly | Cys | Ser | Cys | Pro |
| 305 | | | | | 310 | | | | | 315 | | | | | 320 |
| Glu | Gly | Gln | Leu | Leu | Asp | Glu | Gly | Leu | Cys | Val | Glu | Ser | Thr | Glu | Cys |
| | | | | 325 | | | | | 330 | | | | | 335 | |
| Pro | Cys | Val | His | Ser | Gly | Lys | Arg | Tyr | Pro | Pro | Gly | Thr | Ser | Leu | Ser |
| | | | 340 | | | | | 345 | | | | | 350 | | |
| Arg | Asp | Cys | Asn | Thr | Cys | Ile | Cys | Arg | Asn | Ser | Gln | Trp | Ile | Cys | Ser |
| | | 355 | | | | | 360 | | | | | 365 | | | |
| Asn | Glu | Glu | Cys | Pro | Gly | Glu | Cys | Leu | Val | Thr | Gly | Gln | Ser | His | Phe |

|     |     |     | 370 |     |     |     | 375 |     |     |     | 380 |     |     |
| --- | --- | --- | --- | --- | --- | --- | --- | --- | --- | --- | --- | --- | --- |
| Lys | Ser | Phe | Asp | Asn | Arg | Tyr | Phe | Thr | Phe | Ser | Gly | Ile | Cys | Gln | Tyr |
| 385 |     |     |     |     | 390 |     |     |     |     | 395 |     |     |     |     | 400 |

Leu Leu Ala Arg Asp Cys Gln Asp His Ser Phe Ser Ile Val Ile Glu
            405                     410                     415

Thr Val Gln Cys Ala Asp Asp Arg Asp Ala Val Cys Thr Arg Ser Val
            420                     425                     430

Thr Val Arg Leu Pro Gly Leu His Asn Ser Leu Val Lys Leu Lys His
            435                     440                     445

Gly Ala Gly Val Ala Met Asp Gly Gln Asp Val Gln Leu Pro Leu Leu
450                     455                     460

Lys Gly Asp Leu Arg Ile Gln His Thr Val Thr Ala Ser Val Arg Leu
465                     470                     475                     480

Ser Tyr Gly Glu Asp Leu Gln Met Asp Trp Asp Gly Arg Gly Arg Leu
            485                     490                     495

Leu Val Lys Leu Ser Pro Val Tyr Ala Gly Lys Thr Cys Gly Leu Cys
            500                     505                     510

Gly Asn Tyr Asn Gly Asn Gln Gly Asp Asp Phe Leu Thr Pro Ser Gly
            515                     520                     525

Leu Ala Glu Pro Arg Val Glu Asp Phe Gly Asn Ala Trp Lys Leu His
            530                     535                     540

Gly Asp Cys Gln Asp Leu Gln Lys Gln His Ser Asp Pro Cys Ala Leu
545                     550                     555                     560

Asn Pro Arg Met Thr Arg Phe Ser Glu Glu Ala Cys Ala Val Leu Thr
                    565                     570                     575

Ser Pro Thr Phe Glu Ala Cys His Arg Ala Val Ser Pro Leu Pro Tyr
            580                     585                     590

Leu Arg Asn Cys Arg Tyr Asp Val Cys Ser Cys Ser Asp Gly Arg Glu
            595                     600                     605

Cys Leu Cys Gly Ser Tyr Ala Ala Ala Cys Ala Gly Arg Gly Val Arg
            610                     615                     620

Val Ala Trp Arg Glu Pro Gly Arg Cys Glu Leu Asn Cys Pro Lys Gly
625                     630                     635                     640

Gln Val Tyr Leu Gln Cys Gly Thr Pro Cys Asn Leu Thr Cys Arg Ser
                    645                     650                     655

Leu Ser Tyr Pro Asp Glu Glu Cys Asn Glu Ala Cys Leu Glu Gly Cys
                    660                     665                     670

Phe Cys Pro Pro Met Asp Glu Arg Gly Asp Cys Val Pro Lys Ala Gln
            675                     680                     685

Cys Pro Cys Tyr Tyr Asp Gly Glu Ile Phe Gln Pro Glu Asp Ile Phe
            690                     695                     700

Ser Asp His His Thr Met Cys Tyr Cys Glu Asp Gly Phe Met His Cys
705                     710                     715                     720

Thr Met Ser Gly Val Pro Gly Ser Leu Leu Pro Asp Ala Val Leu Ser
                    725                     730                     735

Ser Pro Leu Ser His Arg Ser Lys Arg Ser Leu Ser Cys Arg Pro Pro
            740                     745                     750

Met Val Lys Leu Val Cys Pro Ala Asp Asn Leu Arg Ala Glu Gly Leu
            755                     760                     765

Glu Cys Thr Lys Thr Cys Gln Asn Tyr Asp Leu Glu Cys Met Ser Met
            770                     775                     780

Gly Cys Val Ser Gly Cys Leu Cys Pro Pro Gly Met Val Arg His Glu
785                     790                     795                     800

-continued

```
Asn Arg Cys Glu Arg Cys Pro Cys Phe His Gln Gly Lys Glu Tyr Ala
            805                 810                 815
Pro Gly Glu Thr Val Lys Ile Gly Cys Asn Thr Cys Val Cys Arg Asp
            820                 825                 830
Arg Lys Trp Asn Cys Thr Asp His Val Cys Asp Ala Thr Cys Ser Thr
            835                 840                 845
Ile Gly Met Ala His Tyr Leu Thr Phe Asp Gly Leu Lys Tyr Leu Phe
            850                 855                 860
Pro Gly Glu Cys Gln Tyr Val Leu Val Gln Asp Tyr Cys Gly Ser Asn
865                 870                 875                 880
Pro Gly Thr Phe Arg Ile Leu Val Gly Asn Lys Gly Cys Ser His Pro
            885                 890                 895
Ser Val Lys Cys Lys Lys Arg Val Thr Ile Leu Val Glu Gly Gly Glu
            900                 905                 910
Ile Glu Leu Phe Asp Gly Glu Val Asn Val Lys Arg Pro Met Lys Asp
            915                 920                 925
Glu Thr His Phe Glu Val Val Glu Ser Gly Arg Tyr Ile Ile Leu Leu
            930                 935                 940
Leu Gly Lys Ala Leu Ser Val Val Trp Asp Arg His Leu Ser Ile Ser
945                 950                 955                 960
Val Val Leu Lys Gln Thr Tyr Gln Glu Lys Val Cys Gly Leu Cys Gly
            965                 970                 975
Asn Phe Asp Gly Ile Gln Asn Asn Asp Leu Thr Ser Ser Asn Leu Gln
            980                 985                 990
Val Glu Asp Pro Val Asp Phe Gly Asn Ser Trp Lys Val Ser Ser
            995                 1000                 1005
Gln Cys Ala Asp Thr Arg Lys Val Pro Leu Asp Ser Ser Pro Ala
            1010                1015                1020
Thr Cys His Asn Asn Ile Met Lys Gln Thr Met Val Asp Ser Ser
            1025                1030                1035
Cys Arg Ile Leu Thr Ser Asp Val Phe Gln Asp Cys Asn Lys Leu
            1040                1045                1050
Val Asp Pro Glu Pro Tyr Leu Asp Val Cys Ile Tyr Asp Thr Cys
            1055                1060                1065
Ser Cys Glu Ser Ile Gly Asp Cys Ala Cys Phe Cys Asp Thr Ile
            1070                1075                1080
Ala Ala Tyr Ala His Val Cys Ala Gln His Gly Lys Val Val Thr
            1085                1090                1095
Trp Arg Thr Ala Thr Leu Cys Pro Gln Ser Cys Glu Glu Arg Asn
            1100                1105                1110
Leu Arg Glu Asn Gly Tyr Glu Cys Glu Trp Arg Tyr Asn Ser Cys
            1115                1120                1125
Ala Pro Ala Cys Gln Val Thr Cys Gln His Pro Glu Pro Leu Ala
            1130                1135                1140
Cys Pro Val Gln Cys Val Glu Gly Cys His Ala His Cys Pro Pro
            1145                1150                1155
Gly Lys Ile Leu Asp Glu Leu Leu Gln Thr Cys Val Asp Pro Glu
            1160                1165                1170
Asp Cys Pro Val Cys Glu Val Ala Gly Arg Arg Phe Ala Ser Gly
            1175                1180                1185
Lys Lys Val Thr Leu Asn Pro Ser Asp Pro Glu His Cys Gln Ile
            1190                1195                1200
```

```
Cys His Cys Asp Val Val Asn Leu Thr Cys Glu Ala Cys Gln Glu
1205                1210                1215

Pro Gly Gly Leu Val Val Pro Pro Thr Asp Ala Pro Val Ser Pro
1220                1225                1230

Thr Thr Leu Tyr Val Glu Asp Ile Ser Glu Pro Pro Leu His Asp
1235                1240                1245

Phe Tyr Cys Ser Arg Leu Leu Asp Leu Val Phe Leu Leu Asp Gly
1250                1255                1260

Ser Ser Arg Leu Ser Glu Ala Glu Phe Glu Val Leu Lys Ala Phe
1265                1270                1275

Val Val Asp Met Met Glu Arg Leu Arg Ile Ser Gln Lys Trp Val
1280                1285                1290

Arg Val Ala Val Glu Tyr His Asp Gly Ser His Ala Tyr Ile
1295                1300                1305

Gly Leu Lys Asp Arg Lys Arg Pro Ser Glu Leu Arg Arg Ile Ala
1310                1315                1320

Ser Gln Val Lys Tyr Ala Gly Ser Gln Val Ala Ser Thr Ser Glu
1325                1330                1335

Val Leu Lys Tyr Thr Leu Phe Gln Ile Phe Ser Lys Ile Asp Arg
1340                1345                1350

Pro Glu Ala Ser Arg Ile Thr Leu Leu Leu Met Ala Ser Gln Glu
1355                1360                1365

Pro Gln Arg Met Ser Arg Asn Phe Val Arg Tyr Val Gln Gly Leu
1370                1375                1380

Lys Lys Lys Lys Val Ile Val Ile Pro Val Gly Ile Gly Pro His
1385                1390                1395

Ala Asn Leu Lys Gln Ile Arg Leu Ile Glu Lys Gln Ala Pro Glu
1400                1405                1410

Asn Lys Ala Phe Val Leu Ser Ser Val Asp Glu Leu Glu Gln Gln
1415                1420                1425

Arg Asp Glu Ile Val Ser Tyr Leu Cys Asp Leu Ala Pro Glu Ala
1430                1435                1440

Pro Pro Pro Thr Leu Pro Pro Asp Met Ala Gln Val Thr Val Gly
1445                1450                1455

Pro Gly Leu Leu Gly Val Ser Thr Leu Gly Pro Lys Arg Asn Ser
1460                1465                1470

Met Val Leu Asp Val Ala Phe Val Leu Glu Gly Ser Asp Lys Ile
1475                1480                1485

Gly Glu Ala Asp Phe Asn Arg Ser Lys Glu Phe Met Glu Glu Val
1490                1495                1500

Ile Gln Arg Met Asp Val Gly Gln Asp Ser Ile His Val Thr Val
1505                1510                1515

Leu Gln Tyr Ser Tyr Met Val Thr Val Glu Tyr Pro Phe Ser Glu
1520                1525                1530

Ala Gln Ser Lys Gly Asp Ile Leu Gln Arg Val Arg Glu Ile Arg
1535                1540                1545

Tyr Gln Gly Gly Asn Arg Thr Asn Thr Gly Leu Ala Leu Arg Tyr
1550                1555                1560

Leu Ser Asp His Ser Phe Leu Val Ser Gln Gly Asp Arg Glu Gln
1565                1570                1575

Ala Pro Asn Leu Val Tyr Met Val Thr Gly Asn Pro Ala Ser Asp
1580                1585                1590

Glu Ile Lys Arg Leu Pro Gly Asp Ile Gln Val Val Pro Ile Gly
```

-continued

```
            1595                1600                1605
Val Gly Pro Asn Ala Asn Val Gln Glu Leu Glu Arg Ile Gly Trp
            1610                1615                1620
Pro Asn Ala Pro Ile Leu Ile Gln Asp Phe Glu Thr Leu Pro Arg
            1625                1630                1635
Glu Ala Pro Asp Leu Val Leu Gln Arg Cys Cys Ser Gly Glu Gly
            1640                1645                1650
Leu Gln Ile Pro Thr Leu Ser Pro Ala Pro Asp Cys Ser Gln Pro
            1655                1660                1665
Leu Asp Val Ile Leu Leu Leu Asp Gly Ser Ser Ser Phe Pro Ala
            1670                1675                1680
Ser Tyr Phe Asp Glu Met Lys Ser Phe Ala Lys Ala Phe Ile Ser
            1685                1690                1695
Lys Ala Asn Ile Gly Pro Arg Leu Thr Gln Val Ser Val Leu Gln
            1700                1705                1710
Tyr Gly Ser Ile Thr Thr Ile Asp Val Pro Trp Asn Val Val Pro
            1715                1720                1725
Glu Lys Ala His Leu Leu Ser Leu Val Asp Val Met Gln Arg Glu
            1730                1735                1740
Gly Gly Pro Ser Gln Ile Gly Asp Ala Leu Gly Phe Ala Val Arg
            1745                1750                1755
Tyr Leu Thr Ser Glu Met His Gly Ala Arg Pro Gly Ala Ser Lys
            1760                1765                1770
Ala Val Val Ile Leu Val Thr Asp Val Ser Val Asp Ser Val Asp
            1775                1780                1785
Ala Ala Ala Asp Ala Ala Arg Ser Asn Arg Val Thr Val Phe Pro
            1790                1795                1800
Ile Gly Ile Gly Asp Arg Tyr Asp Ala Ala Gln Leu Arg Ile Leu
            1805                1810                1815
Ala Gly Pro Ala Gly Asp Ser Asn Val Val Lys Leu Gln Arg Ile
            1820                1825                1830
Glu Asp Leu Pro Thr Met Val Thr Leu Gly Asn Ser Phe Leu His
            1835                1840                1845
Lys Leu Cys Ser Gly Phe Val Arg Ile Cys Met Asp Glu Asp Gly
            1850                1855                1860
Asn Glu Lys Arg Pro Gly Asp Val Trp Thr Leu Pro Asp Gln Cys
            1865                1870                1875
His Thr Val Thr Cys Gln Pro Asp Gly Gln Thr Leu Leu Lys Ser
            1880                1885                1890
His Arg Val Asn Cys Asp Arg Gly Leu Arg Pro Ser Cys Pro Asn
            1895                1900                1905
Ser Gln Ser Pro Val Lys Val Glu Glu Thr Cys Gly Cys Arg Trp
            1910                1915                1920
Thr Cys Pro Cys Val Cys Thr Gly Ser Ser Thr Arg His Ile Val
            1925                1930                1935
Thr Phe Asp Gly Gln Asn Phe Lys Leu Thr Gly Ser Cys Ser Tyr
            1940                1945                1950
Val Leu Phe Gln Asn Lys Glu Gln Asp Leu Glu Val Ile Leu His
            1955                1960                1965
Asn Gly Ala Cys Ser Pro Gly Ala Arg Gln Gly Cys Met Lys Ser
            1970                1975                1980
Ile Glu Val Lys His Ser Ala Leu Ser Val Glu Leu His Ser Asp
            1985                1990                1995
```

-continued

```
Met Glu Val Thr Val Asn Gly Arg Leu Val Ser Val Pro Tyr Val
    2000            2005            2010

Gly Gly Asn Met Glu Val Asn Val Tyr Gly Ala Ile Met His Glu
    2015            2020            2025

Val Arg Phe Asn His Leu Gly His Ile Phe Thr Phe Thr Pro Gln
    2030            2035            2040

Asn Asn Glu Phe Gln Leu Gln Leu Ser Pro Lys Thr Phe Ala Ser
    2045            2050            2055

Lys Thr Tyr Gly Leu Cys Gly Ile Cys Asp Glu Asn Gly Ala Asn
    2060            2065            2070

Asp Phe Met Leu Arg Asp Gly Thr Val Thr Thr Asp Trp Lys Thr
    2075            2080            2085

Leu Val Gln Glu Trp Thr Val Gln Arg Pro Gly Gln Thr Cys Gln
    2090            2095            2100

Pro Glu Gln Cys Leu Val Pro Asp Ser Ser His Cys Gln Val Leu
    2105            2110            2115

Leu Leu Pro Leu Phe Ala Glu Cys His Lys Val Leu Ala Pro Ala
    2120            2125            2130

Thr Phe Tyr Ala Ile Cys Gln Gln Asp Ser Cys His Gln Glu Gln
    2135            2140            2145

Val Cys Glu Val Ile Ala Ser Tyr Ala His Leu Cys Arg Thr Asn
    2150            2155            2160

Gly Val Cys Val Asp Trp Arg Thr Pro Asp Phe Cys Ala Met Ser
    2165            2170            2175

Cys Pro Pro Ser Leu Val Tyr Asn His Cys Glu His Gly Cys Pro
    2180            2185            2190

Arg His Cys Asp Gly Asn Val Ser Ser Cys Gly Asp His Pro Ser
    2195            2200            2205

Glu Gly Cys Phe Cys Pro Pro Asp Lys Val Met Leu Glu Gly Ser
    2210            2215            2220

Cys Val Pro Glu Glu Ala Cys Thr Gln Cys Ile Gly Glu Asp Gly
    2225            2230            2235

Val Gln His Gln Phe Leu Glu Ala Trp Val Pro Asp His Gln Pro
    2240            2245            2250

Cys Gln Ile Cys Thr Cys Leu Ser Gly Arg Lys Val Asn Cys Thr
    2255            2260            2265

Thr Gln Pro Cys Pro Thr Ala Lys Ala Pro Thr Cys Gly Leu Cys
    2270            2275            2280

Glu Val Ala Arg Leu Arg Gln Asn Ala Asp Gln Cys Cys Pro Glu
    2285            2290            2295

Tyr Glu Cys Val Cys Asp Pro Val Ser Cys Asp Leu Pro Pro Val
    2300            2305            2310

Pro His Cys Glu Arg Gly Leu Gln Pro Thr Leu Thr Asn Pro Gly
    2315            2320            2325

Glu Cys Arg Pro Asn Phe Thr Cys Ala Cys Arg Lys Glu Glu Cys
    2330            2335            2340

Lys Arg Val Ser Pro Pro Ser Cys Pro Pro His Arg Leu Pro Thr
    2345            2350            2355

Leu Arg Lys Thr Gln Cys Cys Asp Glu Tyr Glu Cys Ala Cys Asn
    2360            2365            2370

Cys Val Asn Ser Thr Val Ser Cys Pro Leu Gly Tyr Leu Ala Ser
    2375            2380            2385
```

-continued

```
Thr Ala Thr Asn Asp Cys Gly Cys Thr Thr Thr Thr Cys Leu Pro
    2390                2395                2400

Asp Lys Val Cys Val His Arg Ser Thr Ile Tyr Pro Val Gly Gln
    2405                2410                2415

Phe Trp Glu Glu Gly Cys Asp Val Cys Thr Cys Thr Asp Met Glu
    2420                2425                2430

Asp Ala Val Met Gly Leu Arg Val Ala Gln Cys Ser Gln Lys Pro
    2435                2440                2445

Cys Glu Asp Ser Cys Arg Ser Gly Phe Thr Tyr Val Leu His Glu
    2450                2455                2460

Gly Glu Cys Cys Gly Arg Cys Leu Pro Ser Ala Cys Glu Val Val
    2465                2470                2475

Thr Gly Ser Pro Arg Gly Asp Ser Gln Ser Ser Trp Lys Ser Val
    2480                2485                2490

Gly Ser Gln Trp Glu Asn Pro Cys Leu Ile Asn Glu Cys Val Arg
    2495                2500                2505

Val Lys Glu Glu Val Phe Ile Gln Gln Arg Asn Val Ser Cys Pro
    2510                2515                2520

Gln Leu Glu Val Pro Val Cys Pro Ser Gly Phe Gln Leu Ser Cys
    2525                2530                2535

Lys Thr Ser Ala Cys Cys Pro Ser Cys Arg Cys Glu Arg Met Glu
    2540                2545                2550

Ala Cys Met Leu Asn Gly Thr Val Ile Gly Pro Gly Lys Thr Val
    2555                2560                2565

Met Ile Asp Val Cys Thr Thr Cys Arg Cys Met Val Gln Val Gly
    2570                2575                2580

Val Ile Ser Gly Phe Lys Leu Glu Cys Arg Lys Thr Thr Cys Asn
    2585                2590                2595

Pro Cys Pro Leu Gly Tyr Lys Glu Glu Asn Asn Thr Gly Glu Cys
    2600                2605                2610

Cys Gly Arg Cys Leu Pro Thr Ala Cys Thr Ile Gln Leu Arg Gly
    2615                2620                2625

Gly Gln Ile Met Thr Leu Lys Arg Asp Glu Thr Leu Gln Asp Gly
    2630                2635                2640

Cys Asp Thr His Phe Cys Lys Val Asn Glu Arg Gly Glu Tyr Phe
    2645                2650                2655

Trp Glu Lys Arg Val Thr Gly Cys Pro Pro Phe Asp Glu His Lys
    2660                2665                2670

Cys Leu Ala Glu Gly Gly Lys Ile Met Lys Ile Pro Gly Thr Cys
    2675                2680                2685

Cys Asp Thr Cys Glu Glu Pro Glu Cys Asn Asp Ile Thr Ala Arg
    2690                2695                2700

Leu Gln Tyr Val Lys Val Gly Ser Cys Lys Ser Glu Val Glu Val
    2705                2710                2715

Asp Ile His Tyr Cys Gln Gly Lys Cys Ala Ser Lys Ala Met Tyr
    2720                2725                2730

Ser Ile Asp Ile Asn Asp Val Gln Asp Gln Cys Ser Cys Cys Ser
    2735                2740                2745

Pro Thr Arg Thr Glu Pro Met Gln His Cys Thr Asn Gly Ser Val
    2750                2755                2760

Val Tyr His Glu Val Leu Asn Ala Met Glu Cys Lys Cys Ser Pro
    2765                2770                2775

Arg Lys Cys Ser Lys
```

2780

<210> SEQ ID NO 3
<211> LENGTH: 2050
<212> TYPE: PRT
<213> ORGANISM: Artificial Sequence
<220> FEATURE:
<223> OTHER INFORMATION: mature VWF

<400> SEQUENCE: 3

```
Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
```

```
            355                 360                 365
Glu Arg Asn Leu Arg Glu Asn Gly Tyr Glu Cys Glu Trp Arg Tyr Asn
            370                 375                 380
Ser Cys Ala Pro Ala Cys Gln Val Thr Cys Gln His Pro Glu Pro Leu
385                 390                 395                 400
Ala Cys Pro Val Gln Cys Val Glu Gly Cys His Ala His Cys Pro Pro
                    405                 410                 415
Gly Lys Ile Leu Asp Glu Leu Leu Gln Thr Cys Val Asp Pro Glu Asp
                    420                 425                 430
Cys Pro Val Cys Glu Val Ala Gly Arg Arg Phe Ala Ser Gly Lys Lys
            435                 440                 445
Val Thr Leu Asn Pro Ser Asp Pro Glu His Cys Gln Ile Cys His Cys
            450                 455                 460
Asp Val Val Asn Leu Thr Cys Glu Ala Cys Gln Glu Pro Gly Gly Leu
465                 470                 475                 480
Val Val Pro Pro Thr Asp Ala Pro Val Ser Pro Thr Thr Leu Tyr Val
                    485                 490                 495
Glu Asp Ile Ser Glu Pro Pro Leu His Asp Phe Tyr Cys Ser Arg Leu
                    500                 505                 510
Leu Asp Leu Val Phe Leu Leu Asp Gly Ser Ser Arg Leu Ser Glu Ala
            515                 520                 525
Glu Phe Glu Val Leu Lys Ala Phe Val Val Asp Met Met Glu Arg Leu
            530                 535                 540
Arg Ile Ser Gln Lys Trp Val Arg Val Ala Val Val Glu Tyr His Asp
545                 550                 555                 560
Gly Ser His Ala Tyr Ile Gly Leu Lys Asp Arg Lys Arg Pro Ser Glu
                    565                 570                 575
Leu Arg Arg Ile Ala Ser Gln Val Lys Tyr Ala Gly Ser Gln Val Ala
                    580                 585                 590
Ser Thr Ser Glu Val Leu Lys Tyr Thr Leu Phe Gln Ile Phe Ser Lys
            595                 600                 605
Ile Asp Arg Pro Glu Ala Ser Arg Ile Thr Leu Leu Leu Met Ala Ser
            610                 615                 620
Gln Glu Pro Gln Arg Met Ser Arg Asn Phe Val Arg Tyr Val Gln Gly
625                 630                 635                 640
Leu Lys Lys Lys Lys Val Ile Val Ile Pro Val Gly Ile Gly Pro His
                    645                 650                 655
Ala Asn Leu Lys Gln Ile Arg Leu Ile Glu Lys Gln Ala Pro Glu Asn
                    660                 665                 670
Lys Ala Phe Val Leu Ser Ser Val Asp Glu Leu Glu Gln Gln Arg Asp
            675                 680                 685
Glu Ile Val Ser Tyr Leu Cys Asp Leu Ala Pro Glu Ala Pro Pro Pro
            690                 695                 700
Thr Leu Pro Pro Asp Met Ala Gln Val Thr Val Gly Pro Gly Leu Leu
705                 710                 715                 720
Gly Val Ser Thr Leu Gly Pro Lys Arg Asn Ser Met Val Leu Asp Val
                    725                 730                 735
Ala Phe Val Leu Glu Gly Ser Asp Lys Ile Gly Glu Ala Asp Phe Asn
                    740                 745                 750
Arg Ser Lys Glu Phe Met Glu Glu Val Ile Gln Arg Met Asp Val Gly
            755                 760                 765
Gln Asp Ser Ile His Val Thr Val Leu Gln Tyr Ser Tyr Met Val Thr
            770                 775                 780
```

```
Val Glu Tyr Pro Phe Ser Glu Ala Gln Ser Lys Gly Asp Ile Leu Gln
785                 790                 795                 800

Arg Val Arg Glu Ile Arg Tyr Gln Gly Gly Asn Arg Thr Asn Thr Gly
                805                 810                 815

Leu Ala Leu Arg Tyr Leu Ser Asp His Ser Phe Leu Val Ser Gln Gly
            820                 825                 830

Asp Arg Glu Gln Ala Pro Asn Leu Val Tyr Met Val Thr Gly Asn Pro
        835                 840                 845

Ala Ser Asp Glu Ile Lys Arg Leu Pro Gly Asp Ile Gln Val Val Pro
850                 855                 860

Ile Gly Val Gly Pro Asn Ala Asn Val Gln Glu Leu Glu Arg Ile Gly
865                 870                 875                 880

Trp Pro Asn Ala Pro Ile Leu Ile Gln Asp Phe Glu Thr Leu Pro Arg
                885                 890                 895

Glu Ala Pro Asp Leu Val Leu Gln Arg Cys Cys Ser Gly Glu Gly Leu
            900                 905                 910

Gln Ile Pro Thr Leu Ser Pro Ala Pro Asp Cys Ser Gln Pro Leu Asp
        915                 920                 925

Val Ile Leu Leu Leu Asp Gly Ser Ser Ser Phe Pro Ala Ser Tyr Phe
930                 935                 940

Asp Glu Met Lys Ser Phe Ala Lys Ala Phe Ile Ser Lys Ala Asn Ile
945                 950                 955                 960

Gly Pro Arg Leu Thr Gln Val Ser Val Leu Gln Tyr Gly Ser Ile Thr
                965                 970                 975

Thr Ile Asp Val Pro Trp Asn Val Val Pro Glu Lys Ala His Leu Leu
            980                 985                 990

Ser Leu Val Asp Val Met Gln Arg Glu Gly Gly Pro Ser Gln Ile Gly
        995                 1000                1005

Asp Ala Leu Gly Phe Ala Val Arg Tyr Leu Thr Ser Glu Met His
    1010                1015                1020

Gly Ala Arg Pro Gly Ala Ser Lys Ala Val Val Ile Leu Val Thr
    1025                1030                1035

Asp Val Ser Val Asp Ser Val Asp Ala Ala Ala Asp Ala Ala Arg
    1040                1045                1050

Ser Asn Arg Val Thr Val Phe Pro Ile Gly Ile Gly Asp Arg Tyr
    1055                1060                1065

Asp Ala Ala Gln Leu Arg Ile Leu Ala Gly Pro Ala Gly Asp Ser
    1070                1075                1080

Asn Val Val Lys Leu Gln Arg Ile Glu Asp Leu Pro Thr Met Val
    1085                1090                1095

Thr Leu Gly Asn Ser Phe Leu His Lys Leu Cys Ser Gly Phe Val
    1100                1105                1110

Arg Ile Cys Met Asp Glu Gly Asn Glu Lys Arg Pro Gly Asp
    1115                1120                1125

Val Trp Thr Leu Pro Asp Gln Cys His Thr Val Thr Cys Gln Pro
    1130                1135                1140

Asp Gly Gln Thr Leu Leu Lys Ser His Arg Val Asn Cys Asp Arg
    1145                1150                1155

Gly Leu Arg Pro Ser Cys Pro Asn Ser Gln Ser Pro Val Lys Val
    1160                1165                1170

Glu Glu Thr Cys Gly Cys Arg Trp Thr Cys Pro Cys Val Cys Thr
    1175                1180                1185
```

-continued

Gly Ser Ser Thr Arg His Ile Val Thr Phe Asp Gly Gln Asn Phe
1190             1195             1200

Lys Leu Thr Gly Ser Cys Ser Tyr Val Leu Phe Gln Asn Lys Glu
1205             1210             1215

Gln Asp Leu Glu Val Ile Leu His Asn Gly Ala Cys Ser Pro Gly
1220             1225             1230

Ala Arg Gln Gly Cys Met Lys Ser Ile Glu Val Lys His Ser Ala
1235             1240             1245

Leu Ser Val Glu Leu His Ser Asp Met Glu Val Thr Val Asn Gly
1250             1255             1260

Arg Leu Val Ser Val Pro Tyr Val Gly Asn Met Glu Val Asn
1265             1270             1275

Val Tyr Gly Ala Ile Met His Glu Val Arg Phe Asn His Leu Gly
1280             1285             1290

His Ile Phe Thr Phe Thr Pro Gln Asn Asn Glu Phe Gln Leu Gln
1295             1300             1305

Leu Ser Pro Lys Thr Phe Ala Ser Lys Thr Tyr Gly Leu Cys Gly
1310             1315             1320

Ile Cys Asp Glu Asn Gly Ala Asn Asp Phe Met Leu Arg Asp Gly
1325             1330             1335

Thr Val Thr Thr Asp Trp Lys Thr Leu Val Gln Glu Trp Thr Val
1340             1345             1350

Gln Arg Pro Gly Gln Thr Cys Gln Pro Ile Leu Glu Glu Cys
1355             1360             1365

Leu Val Pro Asp Ser Ser His Cys Gln Val Leu Leu Pro Leu
1370             1375             1380

Phe Ala Glu Cys His Lys Val Leu Ala Pro Ala Thr Phe Tyr Ala
1385             1390             1395

Ile Cys Gln Gln Asp Ser Cys His Gln Glu Gln Val Cys Glu Val
1400             1405             1410

Ile Ala Ser Tyr Ala His Leu Cys Arg Thr Asn Gly Val Cys Val
1415             1420             1425

Asp Trp Arg Thr Pro Asp Phe Cys Ala Met Ser Cys Pro Pro Ser
1430             1435             1440

Leu Val Tyr Asn His Cys Glu His Gly Cys Pro Arg His Cys Asp
1445             1450             1455

Gly Asn Val Ser Ser Cys Gly Asp His Pro Ser Glu Gly Cys Phe
1460             1465             1470

Cys Pro Pro Asp Lys Val Met Leu Glu Gly Ser Cys Val Pro Glu
1475             1480             1485

Glu Ala Cys Thr Gln Cys Ile Gly Glu Asp Gly Val Gln His Gln
1490             1495             1500

Phe Leu Glu Ala Trp Val Pro Asp His Gln Pro Cys Gln Ile Cys
1505             1510             1515

Thr Cys Leu Ser Gly Arg Lys Val Asn Cys Thr Thr Gln Pro Cys
1520             1525             1530

Pro Thr Ala Lys Ala Pro Thr Cys Gly Leu Cys Glu Val Ala Arg
1535             1540             1545

Leu Arg Gln Asn Ala Asp Gln Cys Cys Pro Glu Tyr Glu Cys Val
1550             1555             1560

Cys Asp Pro Val Ser Cys Asp Leu Pro Pro Val Pro His Cys Glu
1565             1570             1575

Arg Gly Leu Gln Pro Thr Leu Thr Asn Pro Gly Glu Cys Arg Pro

```
                 1580                 1585                 1590
Asn Phe Thr Cys Ala Cys Arg Lys Glu Glu Cys Lys Arg Val Ser
       1595                 1600                 1605

Pro Pro Ser Cys Pro Pro His Arg Leu Pro Thr Leu Arg Lys Thr
       1610                 1615                 1620

Gln Cys Cys Asp Glu Tyr Glu Cys Ala Cys Asn Cys Val Asn Ser
       1625                 1630                 1635

Thr Val Ser Cys Pro Leu Gly Tyr Leu Ala Ser Thr Ala Thr Asn
       1640                 1645                 1650

Asp Cys Gly Cys Thr Thr Thr Thr Cys Leu Pro Asp Lys Val Cys
       1655                 1660                 1665

Val His Arg Ser Thr Ile Tyr Pro Val Gly Gln Phe Trp Glu Glu
       1670                 1675                 1680

Gly Cys Asp Val Cys Thr Cys Thr Asp Met Glu Asp Ala Val Met
       1685                 1690                 1695

Gly Leu Arg Val Ala Gln Cys Ser Gln Lys Pro Cys Glu Asp Ser
       1700                 1705                 1710

Cys Arg Ser Gly Phe Thr Tyr Val Leu His Glu Gly Glu Cys Cys
       1715                 1720                 1725

Gly Arg Cys Leu Pro Ser Ala Cys Glu Val Val Thr Gly Ser Pro
       1730                 1735                 1740

Arg Gly Asp Ser Gln Ser Ser Trp Lys Ser Val Gly Ser Gln Trp
       1745                 1750                 1755

Ala Ser Pro Glu Asn Pro Cys Leu Ile Asn Glu Cys Val Arg Val
       1760                 1765                 1770

Lys Glu Glu Val Phe Ile Gln Gln Arg Asn Val Ser Cys Pro Gln
       1775                 1780                 1785

Leu Glu Val Pro Val Cys Pro Ser Gly Phe Gln Leu Ser Cys Lys
       1790                 1795                 1800

Thr Ser Ala Cys Cys Pro Ser Cys Arg Cys Glu Arg Met Glu Ala
       1805                 1810                 1815

Cys Met Leu Asn Gly Thr Val Ile Gly Pro Gly Lys Thr Val Met
       1820                 1825                 1830

Ile Asp Val Cys Thr Thr Cys Arg Cys Met Val Gln Val Gly Val
       1835                 1840                 1845

Ile Ser Gly Phe Lys Leu Glu Cys Arg Lys Thr Thr Cys Asn Pro
       1850                 1855                 1860

Cys Pro Leu Gly Tyr Lys Glu Asn Asn Thr Gly Glu Cys Cys
       1865                 1870                 1875

Gly Arg Cys Leu Pro Thr Ala Cys Thr Ile Gln Leu Arg Gly Gly
       1880                 1885                 1890

Gln Ile Met Thr Leu Lys Arg Asp Glu Thr Leu Gln Asp Gly Cys
       1895                 1900                 1905

Asp Thr His Phe Cys Lys Val Asn Glu Arg Gly Glu Tyr Phe Trp
       1910                 1915                 1920

Glu Lys Arg Val Thr Gly Cys Pro Pro Phe Asp Glu His Lys Cys
       1925                 1930                 1935

Leu Ala Glu Gly Gly Lys Ile Met Lys Ile Pro Gly Thr Cys Cys
       1940                 1945                 1950

Asp Thr Cys Glu Glu Pro Glu Cys Asn Asp Ile Thr Ala Arg Leu
       1955                 1960                 1965

Gln Tyr Val Lys Val Gly Ser Cys Lys Ser Glu Val Glu Val Asp
       1970                 1975                 1980
```

```
Ile His Tyr Cys Gln Gly Lys Cys Ala Ser Lys Ala Met Tyr Ser
    1985             1990             1995

Ile Asp Ile Asn Asp Val Gln Asp Gln Cys Ser Cys Cys Ser Pro
    2000             2005             2010

Thr Arg Thr Glu Pro Met Gln Val Ala Leu His Cys Thr Asn Gly
    2015             2020             2025

Ser Val Val Tyr His Glu Val Leu Asn Ala Met Glu Cys Lys Cys
    2030             2035             2040

Ser Pro Arg Lys Cys Ser Lys
    2045             2050
```

METHODS OF PROPHYLACTIC TREATMENT USING RECOMBINANT VWF (rVWF)

CROSS REFERENCE TO RELATED APPLICATION

This application claims priority to U.S. Provisional Patent Application No. 62/800,370, filed on Feb. 1, 2019, which is hereby incorporated by reference in its entirety.

REFERENCE TO SEQUENCE LISTING

The Sequence Listing text copy submitted herewith via EFS-Web was created on Mar. 30, 2020, is entitled 008073-5207-US Sequence Listing.txt, is 53,949 bytes in size and is herein incorporated by reference in its entirety.

BACKGROUND OF THE INVENTION

Coagulation diseases, such as von Willebrand Disease (VWD) generally result from a deficiency in the coagulation cascade. von Willebrand Disease (VWD) refers to the group of diseases caused by a deficiency of von Willebrand factor. Von Willebrand factor helps blood platelets clump together and stick to the blood vessel wall, which is necessary for normal blood clotting.

von Willebrand disease (VWD) is the most common inherited bleeding disorder, with an estimated prevalence rate of 1% (Veyradier A, et al., Medicine (Baltimore). 2016, 95(11):e3038). However, excluding milder forms of the disease, only about 1/10,000 patients actually require treatment. Current treatment for these coagulopathies includes a replacement therapy using pharmaceutical preparations comprising the normal coagulation factor.

VWF is a glycoprotein circulating in plasma as a series of multimers ranging in size from about 500 to 20,000 kD. The full length of cDNA of VWF has been cloned; the propolypeptide corresponds to amino acid residues 23 to 764 of the full-length prepro-VWF (Eikenboom et al (1995) Haemophilia 1, 77 90). Multimeric forms of VWF are composed of 250 kD polypeptide subunits linked together by disulfide bonds. VWF mediates the initial platelet adhesion to the sub-endothelium of the damaged vessel wall, with the larger multimers exhibiting enhanced hemostatic activity. Multimerized VWF binds to the platelet surface glycoprotein Gp1bα, through an interaction in the A1 domain of VWF, facilitating platelet adhesion. Other sites on VWF mediate binding to the blood vessel wall. Thus, VWF forms a bridge between the platelet and the vessel wall that is essential to platelet adhesion and primary hemostasis under conditions of high shear stress. Normally, endothelial cells secrete large polymeric forms of VWF and those forms of VWF that have a lower molecular weight arise from proteolytic cleavage. The multimers of exceptionally large molecular masses are stored in the Weibel-Pallade bodies of the endothelial cells and liberated upon stimulation by agonists such as thrombin and histamine.

For patients with VWD, it is recommended that they be treated with von Willebrand factor (VWF) replacement given the need for prolonged hemostasis, particularly in major surgery and in response to other bleeding episodes. However, prophylactic treatments are not well described or known. There remains a need in the art to help patients in advance of such bleeding episodes by means of prophylactic treatment regimens. The present invention meets this need by providing methods for the prophylactic treatment of VWD with human rVWF.

BRIEF SUMMARY OF THE INVENTION

The present invention provides a method for prophylactically treating spontaneous bleeding episodes in a subject with severe von Willebrand Disease (VWD). The method comprises administering to the subject twice-weekly at least one dose of recombinant von Willebrand Factor (rVWF) ranging from at least about 40 IU/kg to about 80 IU/kg, thereby reducing the frequency and/or duration of spontaneous bleeding episodes.

In some embodiments, the at least one dose of rVWF ranges from at least about 50 IU/kg to about 80 IU/kg.

In some embodiments, the subject has a baseline VWF ristocetin cofactor activity (VWF:RCo) ranging from 20 IU/dL or less, or is diagnosed with Type 1 VWD. In certain embodiments, the subject is diagnosed with Type 2A, 2B, or 2M VWD. In particular embodiments, the subject has a VWF:antigen content (VWF:Ag) ranging from 3 IU/dL or greater, or is diagnosed with Type 3 VWD.

In some embodiments, the subject has been administered prophylactic treatment of plasma-derived VWF (pdVWF) within the past 12 months before initial administration of rVWF.

In some embodiments, the subject has experienced at least 3 spontaneous bleeding episodes within the past 12 months.

In some embodiments of the method, the administration of rVWF occurs every 3 to 4 days. In some embodiments, the administration occurs on day 1 and day 5, day 2 and day 6, or day 3 and day 7 of a 7 day period. In certain embodiments, the administration occurs at least every 24 hours, 36 hours, 48 hours, 72 hours, or 84 hours. In some embodiments, the administration occurs at least every 72 hours.

In some embodiments, the method as outlined further comprises administering to the subject at least one dose of recombinant Factor VIII (rFVIII). In some embodiments, the administration of the at least one dose of rFVIII is concomitantly or sequentially administered with the at least one dose of rVWF.

In some embodiments, the subject resumes the prophylactic treatment after receiving elective surgery or oral surgery. In some embodiments, if the elective surgery is minor surgery or oral surgery and the subject has FVIII activity (FVIII:C) of at least 0.4 IU/mL or greater, the subject is administered rVWF without rFVIII before surgery. In certain embodiments, if the elective surgery is major surgery and the subject has FVIII activity (FVIII:C) of at least 0.8 IU/mL or greater, the subject is administered rVWF without rFVIII before surgery.

In some embodiments, prophylactic treatment efficacy is indicated by a reduction of ≥25% in annual bleeding rate (ABR) for spontaneous bleeding episodes during rVWF prophylaxis relative to the pretreatment ABR.

In some embodiments, prophylactic treatment efficacy is indicated by a reduction of ≥25%, ≥30%, ≥35%, ≥40%, ≥45%, ≥50%, ≥55%, ≥60%, ≥65%, ≥70%, ≥75%, ≥80%, ≥85%, ≥90%, or ≥95% in annual bleeding rate (ABR) for spontaneous bleeding episodes during rVWF prophylaxis relative to the pretreatment ABR.

In some embodiments, prophylactic treatment efficacy is measured by examining vWF:RCo and/or FVIII activities in samples obtained from the subject before and after prophylactic treatment with rVWF.

In some embodiments, prophylactic treatment efficacy is measured by examining FVIII, FVIII:C, VWF:RCo, VWF:Ag, and/or VWF collagen-binding capacity activities in samples obtained from the subject before and after prophylactic treatment with rVWF.

In some embodiments, the samples for examining FVIII, FVIII:C, VWF:RCo, VWF:Ag, and/or VWF collagen-binding capacity activities are obtained 15 minutes, 30 minutes, 60 minutes, 3 hours, 6 hours, 12 hours, 24 hours, 28 hours, 32 hours, 48 hours, 72 hours, or 96 hours, after prophylactic treatment with rVWF.

In some embodiments, the samples for examining FVIII, FVIII:C, VWF:RCo, VWF:Ag, and/or VWF collagen-binding capacity activities are obtained 25 to 31 days after prophylactic treatment with rVWF.

In some embodiments, prophylactic treatment efficacy is determined after or during a bleeding episode, wherein samples for examining FVIII, FVIII:C, VWF:RCo, VWF:Ag, and/or VWF collagen-binding capacity activities are obtained after the bleeding episode, and further wherein the samples are obtained prior to rVWF administration, 2 hours after rVWF administration and then every 12-24 hours until resolution of the bleeding episode.

In some embodiments, prophylactic treatment efficacy is indicated by an improvement in FVIII, FVIII:C, VWF:RCo, VWF:Ag, and/or VWF collagen-binding capacity activity levels after the prophylactic treatment with rVWF as compared to the levels prior to the prophylactic treatment with rVWF.

Also provided herein is a method for prophylactically treating spontaneous bleeding episodes in a subject with severe von Willebrand Disease (VWD). The method comprises administering to the subject a weekly dose of recombinant von Willebrand Factor (rVWF) substantially equivalent to a corresponding weekly dose of plasma-derived VWF (pdVWF) previously administered to said subject, thereby reducing the frequency and/or duration of spontaneous bleeding episodes.

In some embodiments, the weekly dose of rVWF is about 10% less than the corresponding weekly dose of pdVWF. In some embodiments, the weekly dose of rVWF is about 10% more than the corresponding weekly dose of pdVWF.

In some embodiments, the weekly dose of rVWF is two individual infusions administered on separate days. In some embodiments, the weekly dose of rVWF is three individual infusions administered on separate days. In some embodiments, the weekly dose of rVWF is a single infusion.

In some embodiments, each individual infusion comprises up to 80 IU/kg rVWF.

In some embodiments, each individual infusion comprises 80 IU/kg rVWF.

In some embodiments, each individual infusion comprises 50 IU/kg rVWF.

In some embodiments, the subject has a baseline VWF ristocetin cofactor activity (VWF:RCo) ranging from 20 IU/dL or less, or is diagnosed with Type 1 VWD. In some embodiments, the subject is diagnosed with Type 2A, 2B, or 2M VWD. In some embodiments, the subject has a VWF:antigen content (VWF:Ag) ranging from 3 IU/dL or greater, or is diagnosed with Type 3 VWD.

In some embodiments, the subject has received prophylactic treatment of pdVWF for at least 12 months.

In some embodiments, the two individual infusions are administered on day 1 and day 5, or day 2 and day 6, or day 3 and day 7 of a 7 day period. In certain embodiments, the three individual infusions are administered on day 1, day 3, and day 6 of a 7 day period. In some embodiments, the administration occurs at least every 24 hours, 36 hours, 48 hours, 72 hours, or 84 hours. In particular embodiments, the administration occurs at least every 72 hours.

In some embodiments, the method provided herein further comprises administering to the subject at least one dose of recombinant Factor VIII (rFVIII).

In some embodiments, the administration of the at least one dose of rFVIII is concomitantly or sequentially administered with the weekly dose of rVWF.

In some embodiments, the subject resumes the prophylactic treatment after receiving elective surgery or oral surgery. In some embodiments, if the elective surgery is minor surgery or oral surgery and the subject has a FVIII activity (FVIII:C) of at least 0.4 IU/mL or greater, the subject is administered rVWF without rFVIII prior to surgery. In some embodiments, if the elective surgery is major surgery and the subject has a FVIII activity (FVIII:C) of at least 0.8 IU/mL or greater, the subject is administered rVWF without rFVIII prior to surgery.

In some embodiments, prophylactic treatment efficacy is indicated by a reduction of ≥25% in annual bleeding rate (ABR) for spontaneous bleeding episodes during rVWF prophylaxis relative to the pretreatment ABR.

In some embodiments, prophylactic treatment efficacy is indicated by a reduction of ≥25%, ≥30%, ≥35%, ≥40%, ≥45%, ≥50%, ≥55%, ≥60%, ≥65%, ≥70%, ≥75%, ≥80%, ≥85%, ≥90%, or ≥95% in annual bleeding rate (ABR) for spontaneous bleeding episodes during rVWF prophylaxis relative to the pretreatment ABR.

In some embodiments, prophylactic treatment efficacy is measured by examining vWF:RCo and/or FVIII activities in samples obtained from the subject before and after prophylactic treatment with rVWF.

In some embodiments, prophylactic treatment efficacy is measured by examining FVIII, FVIII:C, VWF:RCo, VWF:Ag, and/or VWF collagen-binding capacity activities in samples obtained from the subject before and after prophylactic treatment with rVWF.

In some embodiments, the samples for examining FVIII, FVIII:C, VWF:RCo, VWF:Ag, and/or VWF collagen-binding capacity activities are obtained 15 minutes, 30 minutes, 60 minutes, 3 hours, 6 hours, 12 hours, 24 hours, 28 hours, 32 hours, 48 hours, 72 hours, or 96 hours, after prophylactic treatment with rVWF.

In some embodiments, the samples for examining FVIII, FVIII:C, VWF:RCo, VWF:Ag, and/or VWF collagen-binding capacity activities are obtained 25 to 31 days after prophylactic treatment with rVWF.

In some embodiments, prophylactic treatment efficacy is determined after or during a bleeding episode, wherein samples for examining FVIII, FVIII:C, VWF:RCo, VWF:Ag, and/or VWF collagen-binding capacity activities are obtained after the bleeding episode, and further wherein the samples are obtained prior to rVWF administration, 2 hours after rVWF administration and then every 12-24 hours until resolution of the bleeding episode.

In some embodiments, prophylactic treatment efficacy is indicated by an improvement in FVIII, FVIII:C, VWF:RCo, VWF:Ag, and/or VWF collagen-binding capacity activity levels after the prophylactic treatment with rVWF as compared to the levels prior to the prophylactic treatment with rVWF.

In some embodiments, spontaneous bleeding or bleeding episode comprises any one selected from the group consisting of hemarthrosis, epistaxis, muscle bleeding, oral bleeding, and gastrointestinal bleeding.

In some embodiments of any of the methods described, the subject is not diagnosed with type 2N VWD or pseudo VWD.

Other objects, advantages and embodiments of the invention will be apparent from the detailed description following.

BRIEF DESCRIPTION OF THE DRAWINGS

FIG. 2 shows a table of the key study inclusion and exclusion criteria.

FIG. 3 shows a table of exemplary dosing schedules for rVWF prophylaxis.

FIG. 4 shows a table of main study outcome measures.

FIG. 5A-FIG. 5C depict the nucleic acid sequence of human recombinant prepro-VWF.

FIG. 6A-FIG. 6J depict the amino acid sequence of human recombinant prepro-VWF.

FIG. 7A-FIG. 7G depict the amino acid sequence of human recombinant mature VWF.

DETAILED DESCRIPTION OF THE INVENTION

Introduction

Figure 1:
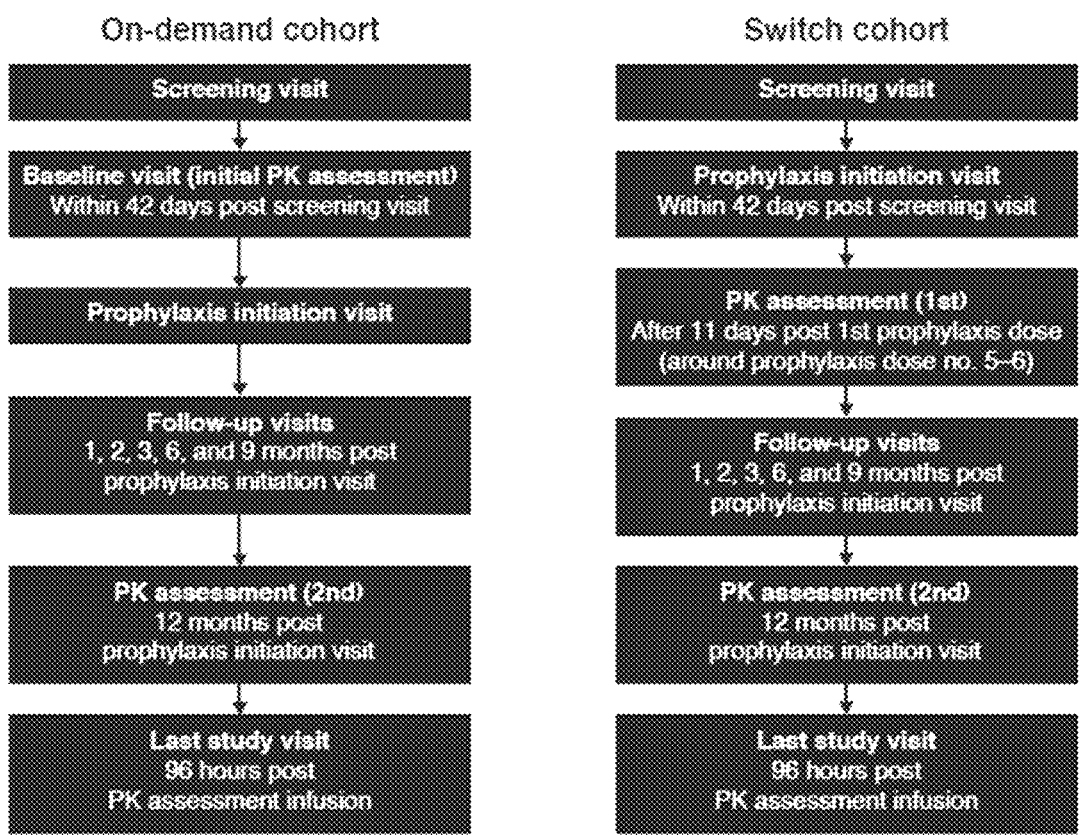
FIG. 1 shows the study design for the global, multicenter, open-label, phase 3 study (NCT02973087, EudraCT no.: 2016-001478-14) described herein.

For patients with VWD, it is recommended that they be treated with von Willebrand factor (VWF) replacement given the need for prolonged hemostasis, particularly in major surgery (Mannucci P M and Franchini M., Haemophilia, 2017, 23(2):182-187; National Institutes of Health. National Heart, Lung, and Blood Institute. The Diagnosis, Evaluation, and Management of von Willebrand Disease NIH Publication No. 08-5832; December, 2007). Plasma-derived VWF therapies contain factor VIII (FVIII) and have the potential for FVIII accumulation with repeated dosing.

VONVENDI® which is approved for the US and its EU approved equivalent, VEYVONDI® each cover recombinant von Willebrand factor (rVWF) concentrates that are manufactured by recombinant DNA technology in the Chinese hamster ovary cell line without the addition of exogenous human or animal-derived protein (Turecek P L, et al. Hamostaseologie. 2009; 29(suppl 1):S32-38; Mannucci P M, et al. Blood, 2013; 122(5):648-657; Gill J C, et al. Blood, 2015; 126(17):2038-2046; European Medicines Agency. VEYVONDI Summary of Product Characteristics). rVWF contains the full VWF multimer profile, including ultra-large multimers that are usually deficient in plasma-derived VWF (pdVWF) concentrates exposed to ADAMTS13, the VWF-cleaving protein.

Most patient with VWD present with mild to moderate mucosal bleeding and bleeding after trauma or surgery, although life-threatening bleeding may also occur, particularly in patient with severe disease (Nichols et al., Haemophilia, 2008, 14:171-232; Leebeek F W and Eikenboom J C, N Engl J Med, 2016, 375:2067-80). Reducing the frequency and duration of bleeding episodes would be expected to decrease the need for red blood cell transfusions and lower the risk of debilitating comorbidities including arthopathy.

Patients with severe VWD may benefit from prophylactic rVWF treatment to maintain VWF and FVIII levels so that the risk of spontaneous bleeding episodes (BEs), including hemarthrosis, epistaxis, and gastrointestinal bleeding, is reduced (Abshire T C, Thromb Res 2009, 124(suppl 1):S23-6; Berntorp E, Haemophilia 2008, 14(suppl 5):47-53; Berntorp E and Petrini P, Blood Coagul Fibrinolysis, 2005, 16 (suppl 1): S23-6; Berntorp E, Semin Thromb Hemost, 2006, 32:621-5; Abshire et al., Haemophilia, 2013, 19:76-81; Abshire T C, J Thromb Haemost, 2015, 13:1585-9).

The present invention provides methods for prophylactically treating spontaneous bleeding in a patient with severe von Willebrand Disease (VWD). The method comprises administering to the subject recombinant von Willebrand factor (rVWF). In some embodiments, the subject is administered a twice-weekly dose ranging from about 40-80 IU/kg of rVWF. In some embodiments, the subject is administered a weekly dose ranging from about 40-80 IU/kg of rVWF. In some instances, the weekly dose is provided as a single administration once a week. In certain instances, the weekly dose is provided as two separate administrations on different days over a week. In other instances, the weekly dose is provided as three separate administrations on different days over a week.

The disclosure of PCT Application Publication No. WO2012/171031 is herein incorporated by reference in its entirety for all purposes.

Definitions

Before the invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

As used herein. "rVWF" refers to recombinant VWF.

As used herein, "rFVIII" refers to recombinant FVIII.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

As used herein, "recombinant VWF" includes VWF obtained via recombinant DNA technology. In certain embodiments, VWF proteins of the invention can comprise a construct, for example, prepared as in WO 1986/06096 published on Oct. 23, 1986 and U.S. patent application Ser. No. 07/559,509, filed on Jul. 23, 1990, in the name of Ginsburg et al., which is incorporated herein by reference with respect to the methods of producing recombinant VWF. The VWF in the present invention can include all potential forms, including the monomeric and multimeric forms. It should also be understood that the present invention encompasses different forms of VWF to be used in combination. For example, the VWF of the present invention may include different multimers, different derivatives and both biologically active derivatives and derivatives not biologically active.

In the context of the present invention, the recombinant VWF embraces any member of the VWF family from, for example, a mammal such as a primate, human, monkey, rabbit, pig, rodent, mouse, rat, hamster, gerbil, canine, feline, and biologically active derivatives thereof. Mutant and variant VWF proteins having activity are also embraced, as are functional fragments and fusion proteins of the VWF proteins. Furthermore, the VWF of the invention may further comprise tags that facilitate purification, detection, or both. The VWF described herein may further be modified with a therapeutic moiety or a moiety suitable imaging in vitro or in vivo.

As used herein, "plasma-derived VWF" or "pdVWF" includes all forms of the protein found in blood including the mature VWF obtained from a mammal having the property of in vivo-stabilizing, e.g. binding, of at least one FVIII molecule.

The term "highly multimeric VWF" or "high molecular weight VWF" refers to VWF comprising at least 10 subunits, or 12, 14, or 16 subunits, to about 20, 22, 24 or 26 subunits or more. The term "subunit" refers to a monomer of VWF. As is known in the art, it is generally dimers of VWF that polymerize to form the larger order multimers (see Turecek et al., Semin. Thromb. Hemost. 2010, 36(5): 510-521 which is hereby incorporated by reference in its entirety for all purposes and in particular for all teachings regarding multimer analysis of VWF).

As used herein, the term "factor VIII" or "FVIII" refers to any form of factor VIII molecule with the typical characteristics of blood coagulation factor VIII, whether endogenous to a patient, derived from blood plasma, or produced through the use of recombinant DNA techniques, and including all modified forms of factor VIII. Factor VIII (FVIII) exists naturally and in therapeutic preparations as a heterogeneous distribution of polypeptides arising from a single gene product (see, e.g., Andersson et al., Proc. Natl. Acad. Sci. USA, 83:2979-2983 (1986)). Commercially available examples of therapeutic preparations containing Factor VIII include those sold under the trade names of HEMOFIL M, ADVATE, and RECOMBINATE (available from Baxter Healthcare Corporation, Deerfield, Ill., U.S.A.).

As used herein, "plasma FVIII activity" and "in vivo FVIII activity" are used interchangeably. The in vivo FVIII activity measured using standard assays may be endogenous FVIII activity, the activity of a therapeutically administered FVIII (recombinant or plasma derived), or both endogenous and administered FVIII activity. Similarly, "plasma FVIII" refers to endogenous FVIII or administered recombinant or plasma derived FVIII.

As used herein "von Willebrand Disease" refers to the group of diseases caused by a deficiency of von Willebrand factor. Von Willebrand factor helps blood platelets clump together and stick to the blood vessel wall, which is necessary for normal blood clotting. As described in further detail herein, there are several types of Von Willebrand disease including type 1, 2A, 2B, 2M and 3.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. VWF is the predominant species present in a preparation is substantially purified. The term "purified" in some embodiments denotes that a nucleic acid or protein gives rise to essentially one band in an electrophoretic gel. In other embodiments, it means that the nucleic acid or protein is at least 50% pure, more preferably at least 60%, 65%, 70%, 75%, 80%, 85%, 90%, 95%, 96%, 97%, 98%, 99% or more pure. "Purify" or "purification" in other embodiments means removing at least one contaminant from the composition to be purified. In this sense, purification does not require that the purified compound be homogenous, e.g., 100% pure.

As used herein, "administering" (and all grammatical equivalents) includes intravenous administration, intramuscular administration, subcutaneous administration, oral administration, administration as a suppository, topical contact, intraperitoneal, intralesional, or intranasal administration, or the implantation of a slow-release device, e.g., a mini-osmotic pump, to a subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The terms "therapeutically effective amount or dose" or "therapeutically sufficient amount or dose" or "effective or sufficient amount or dose" refer to a dose that produces therapeutic effects for which it is administered. For example, a therapeutically effective amount of a drug useful for treating hemophilia can be the amount that is capable of preventing or relieving one or more symptoms associated with hemophilia. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

As used herein, the terms "patient" and "subject" are used interchangeably and refer to a mammal (preferably human) that has a disease or has the potential of contracting a disease.

As used herein, the term "about" denotes an approximate range of plus or minus 10% from a specified value. For instance, the language "about 20%" encompasses a range of 18-22%.

As used herein, the term "half-life" refers to the period of time it takes for the amount of a substance undergoing decay (or clearance from a sample or from a patient) to decrease by half.

I. Recombinant von Willebrand Factor (rVWF)

The present invention utilizes compositions comprising von Willebrand Factor (rVWF) for prophylactic treatment for spontaneous bleeding episodes in a subject with severe VWD. In some embodiments, the treatment reduces the severity, incidence (frequency) and/or duration of spontaneous bleeding episodes.

In certain embodiments, VWF proteins of the invention may comprise a construct, for example, prepared as in WO 1986/06096 published on Oct. 23, 1986 and U.S. patent application Ser. No. 07/559,509, filed on Jul. 23, 1990, in the name of Ginsburg et al., which is incorporated herein by reference with respect to the methods of producing recombinant VWF. The VWF useful for the present invention includes all potential forms, including the monomeric and multimeric forms. One particularly useful form of VWF are homo-multimers of at least two VWFs. The VWF proteins may be either a biologically active derivative, or when to be used solely as a stabilizer for FVIII the VWF may be of a form not biologically active. It should also be understood that the present invention encompasses different forms of VWF to be used in combination. For example, a composition useful for the present invention may include different multimers, different derivatives and both biologically active derivatives and derivatives not biologically active.

In primary hemostasis VWF serves as a bridge between platelets and specific components of the extracellular matrix, such as collagen. The biological activity of VWF in this process can be measured by different in vitro assays (Turecek et al., Semin. Thromb. Hemost. 28: 149-160, 2002). The ristocetin cofactor assay is based on the agglutination of fresh or formalin-fixed platelets induced by the antibiotic ristocetin in the presence of VWF.

The degree of platelet agglutination depends on the VWF concentration and can be measured by the turbidimetric method, e.g. by use of an aggregometer (Weiss et al., J. Clin. Invest. 52: 2708-2716, 1973; Macfarlane et al., Thromb. Diath. Haemorrh. 34: 306-308, 1975). The second method is the collagen binding assay, which is based on ELISA technology (Brown et Bosak, Thromb. Res. 43: 303-311, 1986; Favaloro, Thromb. Haemost. 83: 127-135, 2000). A microtiter plate is coated with type I or III collagen. Then the VWF is bound to the collagen surface and subsequently detected with an enzyme-labeled polyclonal antibody. The last step is the substrate reaction, which can be photometrically monitored with an ELISA reader. As provided herein, the specific Ristocetin Cofactor activity of the VWF (VWF:RCo) of the present invention is generally described in terms of mU/μg of VWF, as measured using in vitro assays.

An advantage of the rVWF compositions of the present invention over pdVWF is that rVWF exhibits a higher specific activity than pdVWF. In some embodiments, the rVWF of the invention has a specific activity of at least about 20, 22.5, 25, 27.5, 30, 32.5, 35, 37.5, 40, 42.5, 45, 47.5, 50, 52.5, 55, 57.5, 60, 62.5, 65, 67.5, 70, 72.5, 75, 77.5, 80, 82.5, 85, 87.5, 90, 92.5, 95, 97.5, 100, 105, 110, 115, 120, 125, 130, 135, 140, 145, 150 or more mU/μg.

The rVWF of the present invention is highly multimeric comprising about 10 to about 40 subunits. In further embodiments, the multimeric rVWF produced using methods of the present invention comprise about 10-30, 12-28, 14-26, 16-24, 18-22, 20-21 subunits. In further embodiments, the rVWF is present in multimers varying in size from dimers to multimers of over 40 subunits (>10 million Daltons). The largest multimers provide multiple binding sites that can interact with both platelet receptors and subendothelial matrix sites of injury, and are the most hemostatically active form of VWF. Application of ADAMTS13 will cleave the ultra-large rVWF multimers over time, but during production (generally through expression in cell culture), rVWF compositions of the present invention are generally not exposed to ADAMTS13 and retain their highly multimeric structure.

In one embodiment, a rVWF composition used in the methods described herein has a distribution of rVWF oligomers characterized in that 95% of the oligomers have between 6 subunits and 20 subunits. In other embodiments, the a rVWF composition has a distribution of rVWF oligomers characterized in that 95% of the oligomers have a range of subunits selected from variations 458 to 641 found in Table 2 of WO 2012/171031, which is herein incorporated by reference in its entirety for all purposes.

In one embodiment, a rVWF composition can be characterized according to the percentage of rVWF molecules that are present in a particular higher order rVWF multimer or larger multimer. For example, in one embodiment, at least 20% of rVWF molecules in a rVWF composition used in the methods described herein are present in an oligomeric complex of at least 10 subunits. In another embodiment, at least 20% of rVWF molecules in a rVWF composition used in the methods described herein are present in an oligomeric complex of at least 12 subunits. In yet other embodiments, a rVWF composition used in the methods provided herein has a minimal percentage (e.g., has at least X %) of rVWF molecules present in a particular higher-order rVWF multimer or larger multimer (e.g., a multimer of at least Y subunits) according to any one of variations 134 to 457 found in Table 3 to Table 5, which is herein incorporated by reference in its entirety for all purposes.

In accordance with the above, the rVWF composition administered to the subject (with or without FVIII) generally comprises a significant percentage of high molecular weight (HMW) rVWF multimers. In further embodiments, the BMW rVWF multimer composition comprises at least 10%-80% rVWF decamers or higher order multimers. In further embodiments, the composition comprises about 10-95%, 20-90%, 30-85%, 40-80%, 50-75%, 60-70% decamers or higher order multimers. In further embodiments, the HMW rVWF multimer composition comprises at least about 10%, 20%, 30%, 40%, 50%, 60%, 70%, 80%, 90% decamers or higher order multimers.

Assessment of the number and percentage of rVWF multimers can be conducted using methods known in the art, including without limitation methods using electrophoresis and size exclusion chromatography methods to separate VWF multimers by size, for example as discussed by Cumming et al., (J Clin Pathol. 1993 May; 46(5): 470-473, which is hereby incorporated by reference in its entirety for all purposes and in particular for all teachings related to assessment of VWF multimers). Such techniques may further include immunoblotting techniques (such as Western Blot), in which the gel is immunoblotted with a radiolabeled antibody against VWF followed by chemiluminescent detection (see, for example Wen et al., (1993), J. Clin. Lab. Anal., 7: 317-323, which is hereby incorporated by reference in its entirety for all purposes and in particular for all teachings related to assessment of VWF multimers). Further assays for VWF include VWF:Antigen (VWF:Ag), VWF:Ristocetin Cofactor (VWF:RCof), and VWF:Collagen Binding Activity assay (VWF:CBA), which are often used for diagnosis and classification of Von Willebrand Disease. (see for example Favaloro et al., Pathology, 1997, 29(4): 341-456, which is hereby incorporated by reference in its entirety for all purposes and in particular for all teachings related to assays for VWF).

In further embodiments, higher order rVWF multimers of the invention are stable for about 1 to about 90 hours post-administration. In still further embodiments, the higher order rVWF multimers are stable for about 5-80, 10-70, 15-60, 20-50, 25-40, 30-35 hours post-administration. In yet further embodiments, the higher order rVWF multimers are stable for at least 3, 6, 12, 18, 24, 36, 48, 72 hours post-administration. In certain embodiments the stability of the rVWF multimers is assessed in vitro.

In one embodiment, higher order rVWF multimers used in the compositions and methods provided herein have a half-life of at least 12 hours post administration. In another embodiment, the higher order rVWF multimers have a half-life of at least 24 hours post administration. In yet other embodiments, the higher order rVWF multimers have a half-life selected from variations 642 to 1045 found in Table 6 of WO 2012/171031, which is herein incorporated by reference in its entirety for all purposes.

In specific aspects, the rVWF (recombinant or plasma derived) used in accordance with the present invention are not modified with any conjugation, post-translation or covalent modifications. In particular embodiments, the rVWF of the present invention is not modified with a water soluble polymer, including without limitation, a polyethylene glycol (PEG), a polypropylene glycol, a polyoxyalkylene, a polysialic acid, hydroxyl ethyl starch, a poly-carbohydrate moiety, and the like.

In other aspects, the rVWF (recombinant or plasma derived) used in accordance with the present invention is modified through conjugation, post-translation modification, or covalent modification, including modifications of the N- or C-terminal residues as well as modifications of selected side chains, for example, at free sulfhydryl-groups, primary amines, and hydroxyl-groups. In one embodiment, a water soluble polymer is linked to the protein (directly or via a linker) by a lysine group or other primary amine. In one embodiment, the rVWF proteins of the present invention may be modified by conjugation of a water soluble polymer, including without limitation, a polyethylene glycol (PEG), a polypropylene glycol, a polyoxyalkylene, a polysialic acid, hydroxyl ethyl starch, a poly-carbohydrate moiety, and the like.

Water soluble polymers that may be used to modify the rVWF and/or FVIII include linear and branched structures. The conjugated polymers may be attached directly to the coagulation proteins of the invention, or alternatively may be attached through a linking moiety. Non-limiting examples of protein conjugation with water soluble polymers can be found in U.S. Pat. Nos. 4,640,835; 4,496,689; 4,301,144; 4,670,417; 4,791,192, and 4,179,337, as well as in Abuchowski and Davis "Enzymes as Drugs," Holcenberg and Roberts, Eds., pp. 367 383, John Wiley and Sons, New York (1981), and Hermanson G., Bioconjugate Techniques 2nd Ed., Academic Press, Inc. 2008.

Protein conjugation may be performed by a number of well-known techniques in the art, for example, see Hermanson G., Bioconjugate Techniques 2nd Ed., Academic Press, Inc. 2008. Examples include linkage through the peptide bond between a carboxyl group on one of either the coagulation protein or water-soluble polymer moiety and an amine group of the other, or an ester linkage between a carboxyl group of one and a hydroxyl group of the other. Another linkage by which a coagulation protein of the invention could be conjugated to a water-soluble polymer compound is via a Schiff base, between a free amino group on the polymer moiety being reacted with an aldehyde group formed at the non-reducing end of the polymer by periodate oxidation (Jennings and Lugowski, J. Immunol. 1981; 127: 1011-8; Femandes and Gregonradis, Biochim Biophys Acta. 1997; 1341; 26-34). The generated Schiff Base can be stabilized by specific reduction with $NaCNBH_3$ to form a secondary amine. An alternative approach is the generation of terminal free amino groups on the polymer by reductive amination with $NH_4Cl$ after prior oxidation. Bifunctional reagents can be used for linking two amino or two hydroxyl groups. For example, a polymer containing an amino group can be coupled to an amino group of the coagulation protein with reagents like $BS_3$ (Bis(sulfosuccinimidyl)suberate/ Pierce, Rockford, Ill.). In addition, heterobifunctional cross linking reagents like Sulfo-EMCS (N-epsilon-Maleimidocaproyloxy) sulfosuccinimide ester/Pierce) can be used for instance to link amine and thiol groups. In other embodiments, an aldehyde reactive group, such as PEG alkoxide plus diethyl acetal of bromoacetaldehyde; PEG plus DMSO and acetic anhydride, and PEG chloride plus the phenoxide of 4-hydroxybenzaldehyde, succinimidyl active esters, activated dithiocarbonate PEG, 2,4,5-trichlorophenylcloroformate and P-nitrophenylcloroformate activated PEG, may be used in the conjugation of a coagulation protein.

In some aspects, the rVWF used in methods of the present invention has been matured in vitro with furin. In further embodiments, the furin is recombinant furin.

In further aspects, the rVWF used in the methods of the present invention are produced by expression in a mammalian cell culture using methods known in the art. In particular embodiments, the mammalian culture comprises CHO cells. In an exemplary embodiment, the rVWF of the invention comprises rVWF protein isolated from a CHO cell expression system. In a further embodiment, the propeptide removal is mediated in vitro through exposure of the pro-VWF to furin—in a still further embodiment, the Furin used for propeptide removal is recombinant furin. In as yet further embodiment, fully glycosylated/ABO blood group glycans are absent.

In yet further embodiments, the rVWF used in methods and compositions of the present invention by expression in a suitable eukaryotic host system. Examples of eukaryotic cells include, without limitation, mammalian cells, such as CHO, COS, HEK 293, BHK, SK-Hep, and HepG2; insect cells, e.g., SF9 cells, SF21 cells, S2 cells, and High Five cells; and yeast cells, e.g., *Saccharomyces* or *Schizosaccharomyces* cells. In one embodiment, the VWF can be expressed in yeast cells, insect cells, avian cells, mammalian cells, and the like. For example, in a human cell line, a hamster cell line, or a murine cell line. In one particular embodiment, the cell line is a CHO, BHK, or HEK cell line. Typically, mammalian cells, e.g., CHO cell from a continuous cell line, can be used to express the VWF of the present invention.

In certain embodiments, the nucleic acid sequence comprising a sequence coding for VWF can be a vector. The vector can be delivered by a virus or can be a plasmid. The nucleic acid sequence coding for the protein can be a specific gene or a biologically functional part thereof. In one embodiment, the protein is at least a biologically active part of VWF. A wide variety of vectors can be used for the expression of the VWF and can be selected from eukaryotic expression vectors. Examples of vectors for eukaryotic expression include: (i) for expression in yeast, vectors such as pAO, pPIC, pYES, pMET, using promoters such as AOX1, GAP, GAL1, AUG1, etc; (ii) for expression in insect cells, vectors such as pMT, pAc5, pIB, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived from viral systems such as vaccinia virus, adeno-associated viruses, herpes viruses, retroviruses, etc., using promoters such as CMV, SV40, EF-1, UbC, RSV, ADV, BPV, and β-actin.

In some embodiments of the present invention, the nucleic acid sequence further comprises other sequences suitable for a controlled expression of a protein such as promoter sequences, enhancers, TATA boxes, transcription initiation sites, polylinkers, restriction sites, poly-A-sequences, protein processing sequences, selection markers, and the like which are generally known to a person of ordinary skill in the art.

In certain embodiments, the cell-culture methods of the invention may comprise the use of a microcarrier. In some embodiments, the cell-cultures of the embodiments can be performed in large bioreactors under conditions suitable for providing high volume-specific culture surface areas to achieve high cell densities and protein expression. One means for providing such growth conditions is to use microcarriers for cell-culture in stirred tank bioreactors. The concept of cell-growth on microcarriers was first described by van Wezel (van Wezel, A. L., Nature 216:64-5 (1967)) and allows for cell attachment on the surface of small solid particles suspended in the growth medium. These methods provide for high surface-to-volume ratios and thus allow for efficient nutrient utilization. Furthermore, for expression of secreted proteins in eukaryotic cell lines, the increased surface-to-volume ratio allows for higher levels of secretion and thus higher protein yields in the supernatant of the culture. Finally, these methods allow for the easy scale-up of eukaryotic expression cultures.

The cells expressing VWF can be bound to a spherical or a porous microcarrier during cell culture growth. The microcarrier can be a microcarrier selected from the group of microcarriers based on dextran, collagen, plastic, gelatine and cellulose and others as described in Butler (1988. In: Spier & Griffiths, Animal Cell Biotechnology 3:283-303). It is also possible to grow the cells to a biomass on spherical microcarriers and subculture the cells when they have reached final fermenter biomass and prior to production of the expressed protein on a porous microcarrier or vice versa. Suitable spherical microcarriers can include smooth surface microcarriers, such as Cytodex™ 1, Cytodex™ 2, and Cytode™ 3 (GE Healthcare) and macroporous microcarriers such as Cytopore™ 1, Cytopore™ 2, Cytoline™ 1, and Cytoline™ 2 (GE Healthcare).

In certain embodiments, rVWF is expressed in cells cultured in cell culture media that produces high molecular weight rVWF. The terms "cell culture solution," "cell culture medium or media," and "cell culture supernatant" refer to aspects of cell culture processes generally well known in the art. In the context of the present invention, a cell culture solution can include cell culture media and cell culture supernatant. The cell culture media are externally added to the cell culture solution, optionally together with supplements, to provide nutrients and other components for culturing the cells expressing VWF. The cell culture supernatant refers to a cell culture solution comprising the nutrients and other components from the cell culture medium as well as products released, metabolized, and/or excreted from the cells during culture. In further embodiments, the media can be animal protein-free and chemically defined. Methods of preparing animal protein-free and chemically defined culture media are known in the art, for example in US 2008/0009040 and US 2007/0212770, which are both incorporated herein for all purposes and in particular for all teachings related to cell culture media. "Protein free" and related terms refers to protein that is from a source exogenous to or other than the cells in the culture, which naturally shed proteins during growth. In another embodiment, the culture medium is polypeptide free. In another embodiment, the culture medium is serum free. In another embodiment the culture medium is animal protein free. In another embodiment the culture medium is animal component free. In another embodiment, the culture medium contains protein, e.g., animal protein from serum such as fetal calf serum. In another embodiment, the culture has recombinant proteins exogenously added. In another embodiment, the proteins are from a certified pathogen free animal. The term "chemically defined" as used herein shall mean, that the medium does not comprise any undefined supplements, such as, for example, extracts of animal components, organs, glands, plants, or yeast. Accordingly, each component of a chemically defined medium is accurately defined. In a preferred embodiment, the media are animal-component free and protein free.

In further embodiments, subsequent to purification from a mammalian cell culture, rFVIII is reconstituted prior to administration. In still further embodiments, the rVWF is treated with furin prior to or subsequent to reconstitution. In further embodiments, the furin is recombinant furin. In still further embodiments, the rVWF of the invention is not exposed to ADAMTS13, with the result that ultra large (i.e., comprising 10 or more subunits) are present in rVWF compositions of the invention.

In specific aspects, the rVWF used in methods of the present invention is contained in a formulation containing a buffer, a sugar and/or a sugar alcohol (including without limitation trehalose and mannitol), a stabilizer (such as glycine), and a surfactant (such as polysorbate 80). In further embodiments, for formulations containing rFVIII, the formulation may further include sodium, histidine, calcium, and glutathione.

In one aspect, the formulations comprising rVWF is lyophilized prior to administration. Lyophilization is carried out using techniques common in the art and should be optimized for the composition being developed [Tang et al., Pharm Res. 21:191-200. (2004) and Chang et al., Pharm Res. 13:243-9 (1996)].

Methods of preparing pharmaceutical formulations can include one or more of the following steps: adding a stabilizing agent as described herein to said mixture prior to lyophilizing, adding at least one agent selected from a bulking agent, an osmolarity regulating agent, and a surfactant, each of which as described herein, to said mixture prior to lyophilization. A lyophilized formulation is, in one aspect, at least comprised of one or more of a buffer, a bulking agent, and a stabilizer. In this aspect, the utility of a surfactant is evaluated and selected in cases where aggregation during the lyophilization step or during reconstitution becomes an issue. An appropriate buffering agent is included to maintain the formulation within stable zones of pH during lyophilization.

The standard reconstitution practice for lyophilized material is to add back a volume of pure water or sterile water for injection (WFI) (typically equivalent to the volume removed during lyophilization), although dilute solutions of antibacterial agents are sometimes used in the production of pharmaceuticals for parenteral administration [Chen, Drug Development and Industrial Pharmacy, 18:1311-1354 (1992)]. Accordingly, methods are provided for preparation of reconstituted recombinant VWF compositions comprising the step of adding a diluent to a lyophilized recombinant VWF composition of the invention.

The lyophilized material may be reconstituted as an aqueous solution. A variety of aqueous carriers, e.g., sterile water for injection, water with preservatives for multi dose use, or water with appropriate amounts of surfactants (for example, an aqueous suspension that contains the active compound in admixture with excipients suitable for the manufacture of aqueous suspensions). In various aspects, such excipients are suspending agents, for example and without limitation, sodium carboxymethylcellulose, methylcellulose, hydroxypropylmethylcellulose, sodium alginate, polyvinylpyrrolidone, gum tragacanth and gum acacia; dispersing or wetting agents are a naturally-occurring phosphatide, for example and without limitation, lecithin, or condensation products of an alkylene oxide with fatty acids, for example and without limitation, polyoxyethylene stearate, or condensation products of ethylene oxide with long chain aliphatic alcohols, for example and without limitation, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example and without limitation, polyethylene sorbitan monooleate. In various aspects, the aqueous suspensions also contain one or more preservatives, for example and without limitation, ethyl, or n-propyl, p-hydroxybenzoate.

In certain embodiments, compositions of the present invention are liquid formulations for administration with the use of a syringe or other storage vessel. In further embodiments, these liquid formulations are produced from lyophilized material described herein reconstituted as an aqueous solution.

In a further aspect, the compositions of the invention further comprise one or more pharmaceutically acceptable carriers. The phrases "pharmaceutically" or "pharmacologically" acceptable refer to molecular entities and compositions that are stable, inhibit protein degradation such as aggregation and cleavage products, and in addition do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like, including those agents disclosed above.

II. Production of Recombinant VWF

The free mature recombinant von Willebrand Factor (rVWF) of the present invention can be produced recombinantly. One skilled in the art recognizes useful methods for expressing a recombinant protein in a host cell. In some instances, the method includes expressing a nucleic acid sequence encoding rVWF in a host cell such as a CHO cell and culturing the resulting host cell under certain conditions to produce rVWF, prepro-VWF, pro-VWF, and the like.

In certain embodiments, the nucleic acid sequence comprising a sequence coding for VWF can be an expression vector. The vector can be delivered by a virus or can be a plasmid. The nucleic acid sequence coding for the protein can be a specific gene or a biologically functional part thereof. In one embodiment, the protein is at least a biologically active part of VWF. The nucleic acid sequence can further comprise other sequences suitable for a controlled expression of a protein such as promoter sequences, enhancers, TATA boxes, transcription initiation sites, polylinkers, restriction sites, poly-A-sequences, protein processing sequences, selection markers, and the like which are generally known to a person of ordinary skill in the art.

A wide variety of vectors can be used for the expression of the VWF and can be selected from eukaryotic expression vectors. Examples of vectors for eukaryotic expression include: (i) for expression in yeast, vectors such as pAO, pPIC, pYES, pMET, using promoters such as AOX1, GAP, GAL1, AUG1, etc; (ii) for expression in insect cells, vectors such as pMT, pAc5, pIB, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived from viral systems such as vaccinia virus, adeno-associated viruses, herpes viruses, retroviruses, etc., using promoters such as CMV, SV40, EF-1, UbC, RSV, ADV, BPV, and β-actin.

In some aspects, the rVWF used in the methods of the present invention is produced by expression in a mammalian cell culture using methods known in the art. In particular embodiments, the mammalian culture comprises CHO cells. In further embodiments, the rVWF is co-expressed with recombinant Factor VIII (rFVIII) in the same culture. In such embodiments, the rVWF and the rFVIII are purified together (co-purified) or separately using methods known in the art. In other embodiments, the rVWF is expressed in a culture that does not contain rFVIII.

In some embodiments, rVWF is expressed and isolated from a suitable eukaryotic host system. Examples of eukaryotic cells include, without limitation, mammalian cells, such as CHO, COS, HEK 293, BHK, SK-Hep, and HepG2; insect cells, e.g., SF9 cells, SF21 cells, S2 cells, and High Five cells; and yeast cells, e.g., *Saccharomyces* or *Schizosaccharomyces* cells. In one embodiment, the VWF can be expressed in yeast cells, insect cells, avian cells, mammalian cells, and the like. For example, in a human cell line, a hamster cell line, or a murine cell line. In one particular embodiment, the cell line is a CHO, BHK, or HEK cell line. Typically, mammalian cells, e.g., CHO cell from a continuous cell line, can be used to express the VWF of the present invention. In certain instances, VWF protein is expressed and isolated from a CHO cell expression system.

VWF can be produced in a cell culture system or according to any cell culture method recognized by those in the art. In some embodiments, the cell cultures can be performed in large bioreactors under conditions suitable for providing high volume-specific culture surface areas to achieve high cell densities and protein expression. One means for providing such growth conditions is to use microcarriers for cell-culture in stirred tank bioreactors. The concept of cell-growth on microcarriers was first described by van Wezel (van Wezel, A. L., Nature, 1967, 216:64-5) and allows for cell attachment on the surface of small solid particles suspended in the growth medium. These methods provide for high surface-to-volume ratios and thus allow for efficient nutrient utilization. Furthermore, for expression of secreted proteins in eukaryotic cell lines, the increased surface-to-volume ratio allows for higher levels of secretion and thus higher protein yields in the supernatant of the culture. Finally, these methods allow for the easy scale-up of eukaryotic expression cultures.

The cells expressing VWF can be bound to a spherical or a porous microcarrier during cell culture growth. The microcarrier can be a microcarrier selected from the group of microcarriers based on dextran, collagen, plastic, gelatine and cellulose and others as described in Butler (1988. In: Spier & Griffiths, Animal Cell Biotechnology 3:283-303). It is also possible to grow the cells to a biomass on spherical microcarriers and subculture the cells when they have reached final fermenter biomass and prior to production of the expressed protein on a porous microcarrier or vice versa. Suitable spherical microcarriers can include smooth surface microcarriers, such as Cytodex™ 1, Cytodex™ 2, and Cytodex™ 3 (GE Healthcare) and macroporous microcarriers such as Cytopore™ 1, Cytopore™ 2, Cytoline™ 1, and Cytoline™ 2 (GE Healthcare).

In a further embodiment, the VWF propeptide is cleaved from the non-mature VWF in vitro through exposure of the pro-VWF to furin. In some embodiments, the furin used for propeptide cleavage is recombinant furin.

In certain embodiments, rVWF is expressed in cells cultured in cell culture media that produces high molecular weight rVWF. The terms "cell culture solution," "cell culture medium or media," and "cell culture supernatant" refer to aspects of cell culture processes generally well known in the art. In the context of the present invention, a cell culture solution can include cell culture media and cell culture supernatant. The cell culture media are externally added to the cell culture solution, optionally together with supplements, to provide nutrients and other components for culturing the cells expressing VWF. The cell culture supernatant refers to a cell culture solution comprising the nutrients and other components from the cell culture medium as well as products released, metabolized, and/or excreted from the cells during culture. In further embodiments, the media can be animal protein-free and chemically defined. Methods of preparing animal protein-free and chemically defined culture media are known in the art, for example in US 2006/0094104, US 2007/0212770, and US 2008/0009040, which are both incorporated herein for all purposes and in particular for all teachings related to cell culture media. "Protein free" and related terms refers to protein that is from a source exogenous to or other than the cells in the culture, which naturally shed proteins during growth. In another embodiment, the culture medium is polypeptide free. In another embodiment, the culture medium is serum free. In another embodiment the culture medium is animal protein free. In another embodiment the culture medium is animal component free. In another embodiment, the culture medium contains protein, e.g., animal protein from serum such as fetal calf serum. In another embodiment, the culture has recombinant proteins exogenously added. In another embodiment, the proteins are from a certified pathogen free animal. The term "chemically defined" as used herein shall mean, that the medium does not comprise any undefined supplements, such as, for example, extracts of animal components, organs, glands, plants, or yeast. Accordingly, each component of a chemically defined medium is accurately defined. In a preferred embodiment, the media are animal-component free and protein free.

In certain embodiments, the culture of cells expressing VWF can be maintained for at least about 7 days, or at least about 14 days, 21 days, 28 days, or at least about 5 weeks, 6 weeks, 7 weeks, or at least about 2 months, or 3, 4, 5, 6, 7, 8, 9, 10, 11, 12, 13, 14, 15, 16, 17, 18 months or longer. The cell density at which a cell-culture is maintained at for production of a recombinant VWF protein will depend upon the culture-conditions and medium used for protein expression. One of skill in the art will readily be able to determine the optimal cell density for a cell-culture producing an VWF. In one embodiment, the culture is maintained at a cell density of between about $0.5 \times 10^6$ and $4 \times 10^7$ cells/ml for an extended period of time. In other embodiments, the cell density is maintained at a concentration of between about $1.0 \times 10^6$ and about $1.0 \times 10^7$ cells/ml for an extended period of time. In other embodiments, the cell density is maintained at a concentration of between about $1.0 \times 10^6$ and about $4.0 \times 10^6$ cells/ml for an extended period of time. In other embodiments, the cell density is maintained at a concentration of between about $1.0 \times 10^6$ and about $4.0 \times 10^6$ cells/ml for an extended period of time. In yet other embodiments, the cell density may be maintained at a concentration between about $2.0 \times 10^6$ and about $4.0 \times 10^6$, or between about $1.0 \times 10^6$ and about $2.5 \times 10^6$, or between about $1.5 \times 10^6$ and about $3.5 \times 10^6$, or any other similar range, for an extended period of time. After an appropriate time in cell culture, the rVWF can be isolated from the expression system using methods known in the art.

In a specific embodiment, the cell density of the continuous cell culture for production of rVWF is maintained at a concentration of no more than $2.5 \times 10^6$ cells/mL for an extended period. In other specific embodiments, the cell density is maintained at no more than $2.0 \times 10^6$ cells/mL, $1.5 \times 10^6$ cells/mL, $1.0 \times 10^6$ cells/mL, $0.5 \times 10^6$ cells/mL, or less. In one embodiment, the cell density is maintained at between $1.5 \times 10^6$ cells/mL and $2.5 \times 10^6$ cells/mL.

In one embodiment of the cell cultures described above, the cell culture solution comprises a medium supplement comprising copper. Such cell culture solutions are described, for example, in U.S. Pat. Nos. 8,852,888 and 9,409,971, which is hereby incorporated by reference in its entirety for all purposes and in particular for all teachings related to cell culture methods and compositions for producing recombinant VWF.

The polynucleotide and amino acid sequences of prepro-VWF are set out in SEQ ID NO:1 and SEQ ID NO:2, respectively, and are available at GenBank Accession Nos. NM_000552 (*Homo sapiens* von Willebrand factor (VWF) mRNA) and NP_000543, respectively. The amino acid sequence corresponding to the mature VWF protein is set out in SEQ ID NO: 3 (corresponding to amino acids 764-2813 of the full length prepro-VWF amino acid sequence). In some embodiments, the VWF exhibits at least 80%, at least 85%, at least 90%, at least 95%, at least 96%, at least 97%, at least 98%, at least 99%, or at least 100% identity to the sequence of SEQ ID NO:3. In some embodiments, the rVWF of the invention exhibits at least 80%, at least 85%, at least 90%, at least 95%, at least 96%, at least 97%, at least 98%, at least 99%, or at least 100% identity to the sequence of SEQ ID NO:3. See, for example, U.S. Pat. No. 8,597,910, U.S. Patent Publication No. 2016/0129090, as well as FIGS. 5A-5C, 6A-6J, and 7A-7G.

One form of useful rVWF has at least the property of in vivo-stabilizing, e.g. binding, of at least one Factor VIII (FVIII) molecule and having optionally a glycosylation pattern which is pharmacologically acceptable. Specific examples thereof include VWF without the A2 domain thus resistant to proteolysis (Lankhof et al., Thromb. Haemost. 77: 1008-1013, 1997), and a VWF fragment from Val 449 to Asn 730 including the glycoprotein 1b-binding domain and binding sites for collagen and heparin (Pietu et al., Biochem. Biophys. Res. Commun. 164: 1339-1347, 1989). The determination of the ability of a VWF to stabilize at least one FVIII molecule is, in one aspect, carried out in VWF-deficient mammals according to methods known in the state in the art.

The rVWF of the present invention can be produced by any method known in the art. One specific example is disclosed in WO86/06096 published on Oct. 23, 1986 and U.S. patent application Ser. No. 07/559,509, filed on Jul. 23, 1990, which is incorporated herein by reference with respect to the methods of producing recombinant VWF. Thus, methods are known in the art for (i) the production of recombinant DNA by genetic engineering, e.g. via reverse transcription of RNA and/or amplification of DNA, (ii) introducing recombinant DNA into prokaryotic or eukaryotic cells by transfection, e.g. via electroporation or microinjection, (iii) cultivating the transformed cells, e.g. in a continuous or batchwise manner, (iv) expressing VWF, e.g. constitutively or upon induction, and (v) isolating the VWF, e.g. from the culture medium or by harvesting the transformed cells, in order to (vi) obtain purified rVWF, e.g. via anion exchange chromatography or affinity chromatography. A recombinant VWF is, in one aspect, made in transformed host cells using recombinant DNA techniques well known in the art. For instance, sequences coding for the polypeptide could be excised from DNA using suitable restriction enzymes. Alternatively, the DNA molecule is, in another aspect, synthesized using chemical synthesis techniques, such as the phosphoramidate method. Also, in still another aspect, a combination of these techniques is used.

The invention also provides vectors encoding polypeptides of the invention in an appropriate host. The vector comprises the polynucleotide that encodes the polypeptide operatively linked to appropriate expression control sequences. Methods of effecting this operative linking, either before or after the polynucleotide is inserted into the vector, are well known. Expression control sequences include promoters, activators, enhancers, operators, ribosomal binding sites, start signals, stop signals, cap signals, polyadenylation signals, and other signals involved with the control of transcription or translation. The resulting vector having the polynucleotide therein is used to transform an appropriate host. This transformation may be performed using methods well known in the art.

Any of a large number of available and well-known host cells are used in the practice of this invention. The selection of a particular host is dependent upon a number of factors recognized by the art, including, for example, compatibility with the chosen expression vector, toxicity of the peptides encoded by the DNA molecule, rate of transformation, ease of recovery of the peptides, expression characteristics, biosafety and costs. A balance of these factors must be struck with the understanding that not all host cells are equally effective for the expression of a particular DNA sequence. Within these general guidelines, useful microbial host cells include, without limitation, bacteria, yeast and other fungi, insects, plants, mammalian (including human) cells in culture, or other hosts known in the art.

Transformed host cells are cultured under conventional fermentation conditions so that the desired compounds are expressed. Such fermentation conditions are well known in the art. Finally, the polypeptides are purified from culture media or the host cells themselves by methods well known in the art.

Depending on the host cell utilized to express a compound of the invention, carbohydrate (oligosaccharide) groups are optionally attached to sites that are known to be glycosylation sites in proteins. Generally, O-linked oligosaccharides are attached to serine (Ser) or threonine (Thr) residues while N-linked oligosaccharides are attached to asparagine (Asn) residues when they are part of the sequence Asn-X-Ser/Thr, where X can be any amino acid except proline. X is preferably one of the 19 naturally occurring amino acids not counting proline. The structures of N-linked and O-linked oligosaccharides and the sugar residues found in each type are different. One type of sugar that is commonly found on both N-linked and 0-linked oligosaccharides is N-acetyl-neuraminic acid (referred to as sialic acid). Sialic acid is usually the terminal residue of both N-linked and O-linked oligosaccharides and, by virtue of its negative charge, in one aspect, confers acidic properties to the glycosylated compound. Such site(s) may be incorporated in the linker of the compounds of this invention and are preferably glycosylated by a cell during recombinant production of the polypeptide compounds (e.g., in mammalian cells such as CHO, BHK, COS). In other aspects, such sites are glycosylated by synthetic or semi-synthetic procedures known in the art.

In some embodiments, sialysation (also referred to as sialylation), can be performed on the column as part of the purification procedures described herein (including the anion exchange, cation exchange, size exclusion, and/or immunoaffinity methods). In some embodiments, the sialylation results in increased stability of the rVWF as compared to rVWF that has not undergone sialylation. In some embodiments, the sialylation results in increased stability of the rVWF in blood circulation (for example, after administration to a subject) as compared to rVWF that has not undergone sialylation. In some embodiments, the increased stability of salivated rVWF results in an increase of 10%, 20%, 30%, 40%, 50%, 60%, 70%, 80%, 90%, or more as compared rVWF that has not undergone sialylation. In some embodiments, the sialylation results in increased half-life for the rVWF as compared to rVWF that has not undergone sialylation. In some embodiments, the sialylation results in increased half-life for the rVWF in blood circulation (for example, after administration to a subject) as compared to rVWF that has not undergone sialylation. In some embodiments, the increased half-life of sialylated rVWF results in an increase of 10%, 20%, 30%, 40%, 50%, 60%, 70%, 80%, 90%, or more as compared rVWF that has not undergone sialylation. In some embodiments, the increased half-life of sialylated rVWF results in rVWF that is stable for 1 hour, 2 hours, 3 hours, 4 hours, 6 hours, 12 hours, 24 hours or more in blood circulation (for example, after administration to a subject) as compared to rVWF that has not undergone sialylation. In some embodiments, sialylation increases the number of 2,3 sialylation and/or 2,6 sialylation. In some embodiments, sialylation is increased by the addition of 2,3 sialyltransferase and/or 2,6 sialyltransferase and CMP-NANA (Cytidine-5'-monophospho-N-acetylneuraminic acid sodium salt) as an additional buffer step. In some embodiments, sialylation is increased by the addition of 2,3 sialyltransferase and CMP-NANA (Cytidine-5'-monophospho-N-acetylneuraminic acid sodium salt) as an additional buffer step. In some embodiments, 2,3 sialylation is increased by the addition of 2,3 sialyltransferase and CMP-NANA (Cytidine-5'-monophospho-N-acetylneuraminic acid sodium salt) as an additional buffer step.

In some embodiments, 2,6 sialylation is increased by the addition of 2,6 sialyltransferase and CMP-NANA (Cytidine-5'-monophospho-N-acetylneuraminic acid sodium salt) as an additional buffer step. In some embodiments, 2,3 sialylation and/or 2,6 sialylation are increased by the addition of 2,3 sialyltransferase and/or 2,6 sialyltransferase and CMP-NANA (Cytidine-5'-monophospho-N-acetylneuraminic acid sodium salt) as an additional buffer step. In some embodiments, CMP-NANA is chemically or enzymatic modified to transfer modified sialic acid to potential free position. In some embodiments, sialylation is performed by loading rVWF onto the resin, washing with one or more buffers as described herein to deplete unwanted impurities, apply one or more buffers containing sialyltransferase and CMP-NANA at conditions that allow additional sialylation, and washing with one or more buffers to deplete excess of the sialylation reagents, and eluting with one or more buffers the enhanced rVWF (e.g., the rVWF with increased sialylation). In some embodiments, the sialylation process is performed as part of a cation exchange method, an anion exchange method, a size exclusion method, or an immunoaffinity purification method, as described herein.

Alternatively, the compounds are made by synthetic methods using, for example, solid phase synthesis techniques. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941,763; Finn et al. (1976), The Proteins (3rd ed.) 2: 105-253; and Erickson et al. (1976), The Proteins (3rd ed.) 2: 257-527. Solid phase synthesis is the preferred technique of making individual peptides since it is the most cost-effective method of making small peptides Fragments, variants and analogs of VWF can be produced according to methods that are well-known in the art. Fragments of a polypeptide can be prepared using, without limitation, enzymatic cleavage (e.g., trypsin, chymotrypsin) and also using recombinant means to generate a polypeptide fragments having a specific amino acid sequence. Polypeptide fragments may be generated comprising a region of the protein having a particular activity, such as a multimerization domain or any other identifiable VWF domain known in the art.

Methods of making polypeptide analogs are also well-known. Amino acid sequence analogs of a polypeptide can be substitutional, insertional, addition or deletion analogs. Deletion analogs, including fragments of a polypeptide, lack one or more residues of the native protein which are not essential for function or immunogenic activity. Insertional analogs involve the addition of, e.g., amino acid(s) at a non-terminal point in the polypeptide. This analog may include, for example and without limitation, insertion of an immunoreactive epitope or simply a single residue. Addition analogs, including fragments of a polypeptide, include the addition of one or more amino acids at either or both termini of a protein and include, for example, fusion proteins. Combinations of the aforementioned analogs are also contemplated.

Substitutional analogs typically exchange one amino acid of the wild-type for another at one or more sites within the protein, and may be designed to modulate one or more properties of the polypeptide without the complete loss of other functions or properties. In one aspect, substitutions are conservative substitutions. "Conservative amino acid substitution" is substitution of an amino acid with an amino acid having a side chain or a similar chemical character. Similar amino acids for making conservative substitutions include those having an acidic side chain (glutamic acid, aspartic acid); a basic side chain (arginine, lysine, histidine); a polar amide side chain (glutamine, asparagine); a hydrophobic, aliphatic side chain (leucine, isoleucine, valine, alanine, glycine); an aromatic side chain (phenylalanine, tryptophan, tyrosine); a small side chain (glycine, alanine, serine, threonine, methionine); or an aliphatic hydroxyl side chain (serine, threonine).

In one aspect, analogs are substantially homologous or substantially identical to the recombinant VWF from which they are derived. Analogs include those which retain at least some of the biological activity of the wild-type polypeptide, e.g. blood clotting activity.

Polypeptide variants contemplated include, without limitation, polypeptides chemically modified by such techniques as ubiquitination, glycosylation, including polysialation (or polysialylation), conjugation to therapeutic or diagnostic agents, labeling, covalent polymer attachment such as pegylation (derivatization with polyethylene glycol), introduction of non-hydrolyzable bonds, and insertion or substitution by chemical synthesis of amino acids such as ornithine, which do not normally occur in human proteins. Variants retain the same or essentially the same binding properties of non-modified molecules of the invention. Such chemical modification may include direct or indirect (e.g., via a linker) attachment of an agent to the VWF polypeptide. In the case of indirect attachment, it is contemplated that the linker may be hydrolyzable or non-hydrolyzable.

Preparing pegylated polypeptide analogs will in one aspect comprise the steps of (a) reacting the polypeptide with polyethylene glycol (such as a reactive ester or aldehyde derivative of PEG) under conditions whereby the binding construct polypeptide becomes attached to one or more PEG groups, and (b) obtaining the reaction product(s). In general, the optimal reaction conditions for the acylation reactions are determined based on known parameters and the desired result. For example, the larger the ratio of PEG:protein, the greater the percentage of poly-pegylated product. In some embodiments, the binding construct has a single PEG moiety at the N-terminus. Polyethylene glycol (PEG) may be attached to the blood clotting factor to, for example, provide a longer half-life in vivo. The PEG group may be of any convenient molecular weight and is linear or branched. The average molecular weight of the PEG ranges from about 2 kiloDalton ("kD") to about 100 kDa, from about 5 kDa to about 50 kDa, or from about 5 kDa to about 10 kDa. In certain aspects, the PEG groups are attached to the blood clotting factor via acylation or reductive alkylation through a natural or engineered reactive group on the PEG moiety (e.g., an aldehyde, amino, thiol, or ester group) to a reactive group on the blood clotting factor (e.g., an aldehyde, amino, or ester group) or by any other technique known in the art.

Methods for preparing polysialylated polypeptide are described in United States Patent Publication 20060160948, Fernandes et Gregoriadis; Biochim. Biophys. Acta 1341: 26-34, 1997, and Saenko et al., Haemophilia 12:42-51, 2006. Briefly, a solution of colominic acid (CA) containing 0.1 M NaIO4 is stirred in the dark at room temperature to oxidize the CA. The activated CA solution is dialyzed against, e.g., 0.05 M sodium phosphate buffer, pH 7.2 in the dark and this solution was added to a rVWF solution and incubated for 18 h at room temperature in the dark under gentle shaking. Free reagents are optionally separated from the rVWF-polysialic acid conjugate by, for example, ultrafiltration/diafiltration. Conjugation of rVWF with polysialic acid is achieved using glutaraldehyde as cross-linking reagent (Migneault et al., Biotechniques 37: 790-796, 2004).

It is also contemplated in another aspect that prepro-VWF and pro-VWF polypeptides will provide a therapeutic benefit in the formulations of the present invention. For example, U.S. Pat. No. 7,005,502 describes a pharmaceutical preparation comprising substantial amounts of pro-VWF that induces thrombin generation in vitro. In addition to recombinant, biologically active fragments, variants, or other analogs of the naturally-occurring mature VWF, the present invention contemplates the use of recombinant biologically active fragments, variants, or analogs of the pre-pro-VWF (set out in SEQ ID NO:2) or pro-VWF polypeptides (amino acid residues 23 to 764 of SEQ ID NO: 2), or rVWF (set out in SEQ ID NO:3) in the formulations described herein.

Polynucleotides encoding fragments, variants and analogs may be readily generated by a worker of skill to encode biologically active fragments, variants, or analogs of the naturally-occurring molecule that possess the same or similar biological activity to the naturally-occurring molecule. In various aspects, these polynucleotides are prepared using PCR techniques, digestion/ligation of DNA encoding molecule, and the like. Thus, one of skill in the art will be able to generate single base changes in the DNA strand to result in an altered codon and a missense mutation, using any method known in the art, including, but not limited to site-specific mutagenesis. As used herein, the phrase "moderately stringent hybridization conditions" means, for example, hybridization at 42° C. in 50% formamide and washing at 60° C. in 0.1×SSC, 0.1% SDS. It is understood by those of skill in the art that variation in these conditions occurs based on the length and GC nucleotide base content of the sequences to be hybridized. Formulas standard in the art are appropriate for determining exact hybridization conditions. See Sambrook et al., 9.47-9.51 in Molecular Cloning, Cold Spring Harbor Laboratory Press, Cold Spring Harbor, New York (1989).

A. VWF Multimers

Assessment of the number and percentage of rVWF multimers can be conducted using methods known in the art, including without limitation methods using electrophoresis and size exclusion chromatography methods to separate VWF multimers by size, for example as discussed by Cumming et al., (J Clin Pathol., 1993 May; 46(5): 470-473, which is hereby incorporated by reference in its entirety for all purposes and in particular for all teachings related to assessment of VWF multimers). Such techniques may further include immunoblotting techniques (such as Western Blot), in which the gel is immunoblotted with a radiolabelled antibody against VWF followed by chemiluminescent detection (see, for example, Wen et al., J. Clin. Lab. Anal., 1993, 7: 317-323, which is hereby incorporated by reference in its entirety for all purposes and in particular for all teachings related to assessment of VWF multimers). Further assays for VWF include VWF:Antigen (VWF:Ag), VWF:Ristocetin Cofactor (VWF:RCof), and VWF:Collagen Binding Activity assay (VWF:CBA), which are often used for diagnosis and classification of Von Willebrand Disease (see, for example, Favaloro et al., Pathology, 1997, 29(4): 341-456; Sadler, J E, Annu Rev Biochem, 1998, 67:395-424; and Turecek et al., Semin Thromb Hemost, 2010, 36:510-521, which are hereby incorporated by reference in their entirety for all purposes and in particular for all teachings related to assays for VWF). In some embodiments, the rVWF obtained using the present methods includes any multimer pattern present in the loading sample of the rVWF. In some embodiments, the rVWF obtained using the present methods includes physiological occurring multimer patters as well as ultralarge VWF-multimer patterns.

b. VWF Assays

In primary hemostasis VWF serves as a bridge between platelets and specific components of the extracellular matrix, such as collagen. The biological activity of VWF in this process can be measured by different in vitro assays (Turecek et al., Semin Thromb Hemost, 2010, 36: 510-521).

The VWF:Ristocetin Cofactor (VWF:RCo) assay is based on the agglutination of fresh or formalin-fixed platelets induced by the antibiotic ristocetin in the presence of VWF. The degree of platelet agglutination depends on the VWF concentration and can be measured by the turbidimetric method, e.g., by use of an aggregometer (Weiss et al., J. Clin. Invest., 1973, 52: 2708-2716; Macfarlane et al., Thromb. Diath. Haemorrh., 1975, 34: 306-308). As provided herein, the specific ristocetin cofactor activity of the VWF (VWF:RCo) of the present invention is generally described in terms of mU/µg of VWF, as measured using in vitro assays.

In some embodiments, the rVWF purified according to the methods of the present invention has a specific activity of at least about 20, 22.5, 25, 27.5, 30, 32.5, 35, 37.5, 40, 42.5, 45, 47.5, 50, 52.5, 55, 57.5, 60, 62.5, 65, 67.5, 70, 72.5, 75, 77.5, 80, 82.5, 85, 87.5, 90, 92.5, 95, 97.5, 100, 105, 110, 115, 120, 125, 130, 135, 140, 145, 150 or more mU/µg. In some embodiments, rVWF used in the methods described herein has a specific activity of from 20 mU/µg to 150 mU/µg. In some embodiments, the rVWF has a specific activity of from 30 mU/µg to 120 mU/µg. In some embodiments, the rVWF has a specific activity from 40 mU/µg to 90 mU/µg. In some embodiments, the rVWF has a specific activity selected from variations 1 to 133 found in Table 3, below.

TABLE 3

Exemplary embodiments for the specific activity of rVWF found in the compositions and used in the methods provided herein.

| (mU/µg) | |
|---|---|
| 20 | Var. 1 |
| 22.5 | Var. 2 |
| 25 | Var. 3 |
| 27.5 | Var. 4 |
| 30 | Var. 5 |
| 32.5 | Var. 6 |
| 35 | Var. 7 |
| 37.5 | Var. 8 |
| 40 | Var. 9 |
| 42.5 | Var. 10 |
| 45 | Var. 11 |
| 47.5 | Var. 12 |
| 50 | Var. 13 |
| 52.5 | Var. 14 |
| 55 | Var. 15 |
| 57.5 | Var. 16 |
| 60 | Var. 17 |
| 62.5 | Var. 18 |
| 65 | Var. 19 |
| 67.5 | Var. 20 |
| 70 | Var. 21 |
| 72.5 | Var. 22 |
| 75 | Var. 23 |
| 77.5 | Var. 24 |
| 80 | Var. 25 |
| 82.5 | Var. 26 |
| 85 | Var. 27 |
| 87.5 | Var. 28 |
| 90 | Var. 29 |
| 92.5 | Var. 30 |
| 95 | Var. 31 |
| 97.5 | Var. 32 |
| 100 | Var. 33 |
| 105 | Var. 34 |
| 110 | Var. 35 |
| 115 | Var. 36 |
| 120 | Var. 37 |
| 125 | Var. 38 |
| 130 | Var. 39 |
| 135 | Var. 40 |
| 140 | Var. 41 |
| 145 | Var. 42 |
| 150 | Var. 43 |
| 20-150 | Var. 44 |
| 20-140 | Var. 45 |
| 20-130 | Var. 46 |
| 20-120 | Var. 47 |
| 20-110 | Var. 48 |
| 20-100 | Var. 49 |
| 20-90 | Var. 50 |
| 20-80 | Var. 51 |
| 20-70 | Var. 52 |
| 20-60 | Var. 53 |
| 20-50 | Var. 54 |
| 20-40 | Var. 55 |
| 30-150 | Var. 56 |
| 30-140 | Var. 57 |
| 30-130 | Var. 58 |
| 30-120 | Var. 59 |
| 30-110 | Var. 60 |
| 30-100 | Var. 61 |
| 30-90 | Var. 62 |
| 30-80 | Var. 63 |
| 30-70 | Var. 64 |
| 30-60 | Var. 65 |
| 30-50 | Var. 66 |
| 30-40 | Var. 67 |
| 40-150 | Var. 68 |
| 40-140 | Var. 69 |
| 40-130 | Var. 70 |
| 40-120 | Var. 71 |
| 40-110 | Var. 72 |
| 40-100 | Var. 73 |
| 40-90 | Var. 74 |

TABLE 3-continued

Exemplary embodiments for the specific
activity of rVWF found in the compositions
and used in the methods provided herein.

(mU/µg)

| | |
|---|---|
| 40-80 | Var. 75 |
| 40-70 | Var. 76 |
| 40-60 | Var. 77 |
| 40-50 | Var. 78 |
| 50-150 | Var. 79 |
| 50-140 | Var. 80 |
| 50-130 | Var. 81 |
| 50-120 | Var. 82 |
| 50-110 | Var. 83 |
| 50-100 | Var. 84 |
| 50-90 | Var. 85 |
| 50-80 | Var. 86 |
| 50-70 | Var. 87 |
| 50-60 | Var. 88 |
| 60-150 | Var. 89 |
| 60-140 | Var. 90 |
| 60-130 | Var. 91 |
| 60-120 | Var. 92 |
| 60-110 | Var. 93 |
| 60-100 | Var. 94 |
| 60-90 | Var. 95 |
| 60-80 | Var. 96 |
| 60-70 | Var. 97 |
| 70-150 | Var. 98 |
| 70-140 | Var. 99 |
| 70-130 | Var. 100 |
| 70-120 | Var. 101 |
| 70-110 | Var. 102 |
| 70-100 | Var. 103 |
| 70-90 | Var. 104 |
| 70-80 | Var. 105 |
| 80-150 | Var. 106 |
| 80-140 | Var. 107 |
| 80-130 | Var. 108 |
| 80-120 | Var. 109 |
| 80-110 | Var. 110 |
| 80-100 | Var. 111 |
| 80-90 | Var. 112 |
| 90-150 | Var. 113 |
| 90-140 | Var. 114 |
| 90-130 | Var. 115 |
| 90-120 | Var. 116 |
| 90-110 | Var. 117 |
| 90-100 | Var. 118 |
| 100-150 | Var. 119 |
| 100-140 | Var. 120 |
| 100-130 | Var. 121 |
| 100-120 | Var. 122 |
| 100-110 | Var. 123 |
| 110-150 | Var. 124 |
| 110-140 | Var. 125 |
| 110-130 | Var. 126 |
| 110-120 | Var. 127 |
| 120-150 | Var. 128 |
| 120-140 | Var. 129 |
| 120-130 | Var. 130 |
| 130-150 | Var. 131 |
| 130-140 | Var. 132 |
| 140-150 | Var. 133 |

Var. = Variation

The rVWF of the present invention is highly multimeric comprising about 10 to about 40 subunits. In further embodiments, the multimeric rVWF produced using methods of the present invention comprise about 10-30, 12-28, 14-26, 16-24, 18-22, 20-21 subunits. In some embodiments, the rVWF is present in multimers varying in size from dimers to multimers of over 40 subunits (>10 million Daltons). The largest multimers provide multiple binding sites that can interact with both platelet receptors and subendothelial matrix sites of injury, and are the most hemostatically active form of VWF. In some embodiments, the rVWF of the present invention comprises ultralarge multimers (ULMs). Generally, high and ultralarge multimers are considered to be hemostatically most effective (see, for example, Turecek, P., Hamostaseologie, (Vol. 37): Supplement 1, pages S15-S25 (2017)). In some embodiments, the rVWF is between 500 kDa and 20,000 kDa. In some embodiments, any desired multimer pattern can be obtained using the methods described. In some embodiments, when anion exchange and/or cation exchanger methods are employed, the pH, conductivity, and/or counterion concentration of the buffers in the one or more wash step(s) or the gradient buffers can be manipulated to obtain the desired multimer pattern. In some embodiments, then size exclusion chromatography methods are employed, the collection criteria can be employed to obtain the desired multimer pattern. In some embodiments, the described multimer pattern comprises ultralarge multimers. In some embodiments, the ultralarge multimers are at least 10,000 kDa, at least 11,000 kDa, at least 12,000 kDa, at least 13,000 kDa, at least 14,000 kDa, at least 15,000 kDa, at least 16,000 kDa, at least 17,000 kDa, at least 18,000 kDa, at least 19,000 kDa, at least 20,000 kDa. In some embodiments, the ultralarge multimers are between about 10,000 kDa and 20,000 kDa. In some embodiments, the ultralarge multimers are between about 11,000 kDa and 20,000 kDa. In some embodiments, the ultralarge multimers are between about 12,000 kDa and 20,000 kDa. In some embodiments, the ultralarge multimers are between about 13,000 kDa and 20,000 kDa. In some embodiments, the ultralarge multimers are between about 14,000 kDa and 20,000 kDa. In some embodiments, the ultralarge multimers are between about 15,000 kDa and 20,000 kDa. In some embodiments, the ultralarge multimers are between about 16,000 kDa and 20,000 kDa. In some embodiments, the ultralarge multimers are between about 17,000 kDa and 20,000 kDa. In some embodiments, the ultralarge multimers are between about 18,000 kDa and 20,000 kDa. In some embodiments, the ultralarge multimers are between about 19,000 kDa and 20,000 kDa. In some embodiments, the rVWF obtained using the present methods includes any multimer pattern present in the loading sample of the rVWF. In some embodiments, the rVWF obtained using the present methods includes physiological occurring multimer patters as well as ultra large VWF-multimer patterns.

In some embodiments, the rVWF composition prepared by the purification method described herein has a distribution of rVWF oligomers characterized in that 95% of the oligomers have between 6 subunits and 20 subunits. In some embodiments, the rVWF composition has a distribution of rVWF oligomers characterized in that 95% of the oligomers have a range of subunits selected from variations 458 to 641 found in 4.

TABLE 4

Exemplary embodiments for the distribution of
rVWF oligomers found in the compositions and
used in the methods provided herein.

| Subunits | |
|---|---|
| 2-40 | Var. 458 |
| 2-38 | Var. 459 |
| 2-36 | Var. 460 |
| 2-34 | Var. 461 |
| 2-32 | Var. 462 |
| 2-30 | Var. 463 |
| 2-28 | Var. 464 |
| 2-26 | Var. 465 |
| 2-24 | Var. 466 |

TABLE 4-continued

Exemplary embodiments for the distribution of rVWF oligomers found in the compositions and used in the methods provided herein.

| Subunits | |
|---|---|
| 2-22 | Var. 467 |
| 2-20 | Var. 468 |
| 2-18 | Var. 469 |
| 2-16 | Var. 470 |
| 2-14 | Var. 471 |
| 2-12 | Var. 472 |
| 2-10 | Var. 473 |
| 2-8 | Var. 474 |
| 4-40 | Var. 475 |
| 4-38 | Var. 476 |
| 4-36 | Var. 477 |
| 4-34 | Var. 478 |
| 4-32 | Var. 479 |
| 4-30 | Var. 480 |
| 4-28 | Var. 481 |
| 4-26 | Var. 482 |
| 4-24 | Var. 483 |
| 4-22 | Var. 484 |
| 4-20 | Var. 485 |
| 4-18 | Var. 486 |
| 4-16 | Var. 487 |
| 4-14 | Var. 488 |
| 4-12 | Var. 489 |
| 4-10 | Var. 490 |
| 4-8 | Var. 491 |
| 6-40 | Var. 492 |
| 6-38 | Var. 493 |
| 6-36 | Var. 494 |
| 6-34 | Var. 495 |
| 6-32 | Var. 496 |
| 6-30 | Var. 497 |
| 6-28 | Var. 498 |
| 6-26 | Var. 499 |
| 6-24 | Var. 500 |
| 6-22 | Var. 501 |
| 6-20 | Var. 502 |
| 6-18 | Var. 503 |
| 6-16 | Var. 504 |
| 6-14 | Var. 505 |
| 6-12 | Var. 506 |
| 6-10 | Var. 507 |
| 6-8 | Var. 508 |
| 8-40 | Var. 509 |
| 8-38 | Var. 510 |
| 8-36 | Var. 511 |
| 8-34 | Var. 512 |
| 8-32 | Var. 513 |
| 8-30 | Var. 514 |
| 8-28 | Var. 515 |
| 8-26 | Var. 516 |
| 8-24 | Var. 517 |
| 8-22 | Var. 518 |
| 8-20 | Var. 519 |
| 8-18 | Var. 520 |
| 8-16 | Var. 521 |
| 8-14 | Var. 522 |
| 8-12 | Var. 523 |
| 8-10 | Var. 524 |
| 10-40 | Var. 525 |
| 10-38 | Var. 526 |
| 10-36 | Var. 527 |
| 10-34 | Var. 528 |
| 10-32 | Var. 529 |
| 10-30 | Var. 530 |
| 10-28 | Var. 531 |
| 10-26 | Var. 532 |
| 10-24 | Var. 533 |
| 10-22 | Var. 534 |
| 10-20 | Var. 535 |
| 10-18 | Var. 536 |
| 10-16 | Var. 537 |
| 10-14 | Var. 538 |
| 10-12 | Var. 539 |
| 12-40 | Var. 540 |
| 12-38 | Var. 541 |
| 12-36 | Var. 542 |
| 12-34 | Var. 543 |
| 12-32 | Var. 544 |
| 12-30 | Var. 545 |
| 12-28 | Var. 546 |
| 12-26 | Var. 547 |
| 12-24 | Var. 548 |
| 12-22 | Var. 549 |
| 12-20 | Var. 550 |
| 12-18 | Var. 551 |
| 12-16 | Var. 552 |
| 12-14 | Var. 553 |
| 14-40 | Var. 554 |
| 14-38 | Var. 555 |
| 14-36 | Var. 556 |
| 14-34 | Var. 557 |
| 14-32 | Var. 558 |
| 14-30 | Var. 559 |
| 14-28 | Var. 560 |
| 14-26 | Var. 561 |
| 14-24 | Var. 562 |
| 14-22 | Var. 563 |
| 14-20 | Var. 564 |
| 14-18 | Var. 565 |
| 14-16 | Var. 566 |
| 16-40 | Var. 567 |
| 16-38 | Var. 568 |
| 16-36 | Var. 569 |
| 16-34 | Var. 570 |
| 16-32 | Var. 571 |
| 16-30 | Var. 572 |
| 16-28 | Var. 573 |
| 16-26 | Var. 574 |
| 16-24 | Var. 575 |
| 16-22 | Var. 576 |
| 16-20 | Var. 577 |
| 16-18 | Var. 578 |
| 18-40 | Var. 579 |
| 18-38 | Var. 580 |
| 18-36 | Var. 581 |
| 18-34 | Var. 582 |
| 18-32 | Var. 583 |
| 18-30 | Var. 584 |
| 18-28 | Var. 585 |
| 18-26 | Var. 586 |
| 18-24 | Var. 587 |
| 18-22 | Var. 588 |
| 18-20 | Var. 589 |
| 20-40 | Var. 590 |
| 20-38 | Var. 591 |
| 20-36 | Var. 592 |
| 20-34 | Var. 593 |
| 20-32 | Var. 594 |
| 20-30 | Var. 595 |
| 20-28 | Var. 596 |
| 20-26 | Var. 597 |
| 20-24 | Var. 598 |
| 20-22 | Var. 599 |
| 22-40 | Var. 600 |
| 22-38 | Var. 601 |
| 22-36 | Var. 602 |
| 22-34 | Var. 603 |
| 22-32 | Var. 604 |
| 22-30 | Var. 605 |
| 22-28 | Var. 606 |
| 22-26 | Var. 607 |
| 22-24 | Var. 608 |
| 24-40 | Var. 609 |
| 24-38 | Var. 610 |
| 24-36 | Var. 611 |
| 24-34 | Var. 612 |
| 24-32 | Var. 613 |
| 24-30 | Var. 614 |

TABLE 4-continued

Exemplary embodiments for the distribution of rVWF oligomers found in the compositions and used in the methods provided herein.

| Subunits | |
|---|---|
| 24-28 | Var. 615 |
| 24-26 | Var. 616 |
| 26-40 | Var. 617 |
| 26-38 | Var. 618 |
| 26-36 | Var. 619 |
| 26-34 | Var. 620 |
| 26-32 | Var. 621 |
| 26-30 | Var. 622 |
| 26-28 | Var. 623 |
| 28-40 | Var. 624 |
| 28-38 | Var. 625 |
| 28-36 | Var. 626 |
| 28-34 | Var. 627 |
| 28-32 | Var. 628 |
| 28-30 | Var. 629 |
| 30-40 | Var. 630 |
| 30-38 | Var. 631 |
| 30-36 | Var. 632 |
| 30-34 | Var. 633 |
| 30-32 | Var. 634 |
| 32-40 | Var. 635 |
| 32-38 | Var. 636 |
| 32-36 | Var. 637 |
| 32-34 | Var. 638 |
| 34-40 | Var. 639 |
| 36-38 | Var. 640 |
| 38-40 | Var. 641 |

Var. = Variation

In some embodiments, the rVWF composition prepared by the methods provided herein can be characterized according to the percentage of rVWF molecules that are present in a particular higher order rVWF multimer or larger multimer. For example, in one embodiment, at least 20% of rVWF molecules in a rVWF composition used in the methods described herein are present in an oligomeric complex of at least 10 subunits. In another embodiment, at least 20% of rVWF molecules in a rVWF composition used in the methods described herein are present in an oligomeric complex of at least 12 subunits. In yet other embodiments, a rVWF composition used in the methods provided herein has a minimal percentage (e.g., has at least X %) of rVWF molecules present in a particular higher-order rVWF multimer or larger multimer (e.g., a multimer of at least Y subunits) according to any one of variations 134 to 457 found in Table 5 to Table 7.

TABLE 5

Exemplary embodiments for the percentage of rVWF molecules that are present in a particular higher order rVWF multimer or larger multimer found in the compositions and used in the methods provided herein.

| | | Minimal Number of Subunits in rVWF Multimer | | | | | |
|---|---|---|---|---|---|---|---|
| | | 6 | 8 | 10 | 12 | 14 | 16 |
| Minimal Percentage of rVWF Molecules | 10% | Var. 134 | Var. 152 | Var. 170 | Var. 188 | Var. 206 | Var. 224 |
| | 15% | Var. 135 | Var. 153 | Var. 171 | Var. 189 | Var. 207 | Var. 225 |
| | 20% | Var. 136 | Var. 154 | Var. 172 | Var. 190 | Var. 208 | Var. 226 |
| | 25% | Var. 137 | Var. 155 | Var. 173 | Var. 191 | Var. 209 | Var. 227 |
| | 30% | Var. 138 | Var. 156 | Var. 174 | Var. 192 | Var. 210 | Var. 228 |
| | 35% | Var. 139 | Var. 157 | Var. 175 | Var. 193 | Var. 211 | Var. 229 |
| | 40% | Var. 140 | Var. 158 | Var. 176 | Var. 194 | Var. 212 | Var. 230 |
| | 45% | Var. 141 | Var. 159 | Var. 177 | Var. 195 | Var. 213 | Var. 231 |
| | 50% | Var. 142 | Var. 160 | Var. 178 | Var. 196 | Var. 214 | Var. 232 |
| | 55% | Var. 143 | Var. 161 | Var. 179 | Var. 197 | Var. 215 | Var. 233 |
| | 60% | Var. 144 | Var. 162 | Var. 180 | Var. 198 | Var. 216 | Var. 234 |
| | 65% | Var. 145 | Var. 163 | Var. 181 | Var. 199 | Var. 217 | Var. 235 |
| | 70% | Var. 146 | Var. 164 | Var. 182 | Var. 200 | Var. 218 | Var. 236 |
| | 75% | Var. 147 | Var. 165 | Var. 183 | Var. 201 | Var. 219 | Var. 237 |
| | 80% | Var. 148 | Var. 166 | Var. 184 | Var. 202 | Var. 220 | Var. 238 |
| | 85% | Var. 149 | Var. 167 | Var. 185 | Var. 203 | Var. 221 | Var. 239 |
| | 90% | Var. 150 | Var. 168 | Var. 186 | Var. 204 | Var. 222 | Var. 240 |
| | 95% | Var. 151 | Var. 169 | Var. 187 | Var. 205 | Var. 223 | Var. 241 |

Var. = Variation

TABLE 6

Exemplary embodiments for the percentage of rVWF molecules that are present in a particular higher order rVWF multimer or larger multimer found in the compositions and used in the methods provided herein.

| | | Minimal Number of Subunits in rVWF Multimer | | | | | |
|---|---|---|---|---|---|---|---|
| | | 18 | 20 | 22 | 24 | 26 | 28 |
| Minimal Percentage of rVWF Molecules | 10% | Var. 242 | Var. 260 | Var. 278 | Var. 296 | Var. 314 | Var. 332 |
| | 15% | Var. 243 | Var. 261 | Var. 279 | Var. 297 | Var. 315 | Var. 333 |
| | 20% | Var. 244 | Var. 262 | Var. 280 | Var. 298 | Var. 316 | Var. 334 |
| | 25% | Var. 245 | Var. 263 | Var. 281 | Var. 299 | Var. 317 | Var. 335 |
| | 30% | Var. 246 | Var. 264 | Var. 282 | Var. 300 | Var. 318 | Var. 336 |
| | 35% | Var. 247 | Var. 265 | Var. 283 | Var. 301 | Var. 319 | Var. 337 |
| | 40% | Var. 248 | Var. 266 | Var. 284 | Var. 302 | Var. 320 | Var. 338 |
| | 45% | Var. 249 | Var. 267 | Var. 285 | Var. 303 | Var. 321 | Var. 339 |
| | 50% | Var. 250 | Var. 268 | Var. 286 | Var. 304 | Var. 322 | Var. 340 |
| | 55% | Var. 251 | Var. 269 | Var. 287 | Var. 305 | Var. 323 | Var. 341 |
| | 60% | Var. 252 | Var. 270 | Var. 288 | Var. 306 | Var. 324 | Var. 342 |
| | 65% | Var. 253 | Var. 271 | Var. 289 | Var. 307 | Var. 325 | Var. 343 |
| | 70% | Var. 254 | Var. 272 | Var. 290 | Var. 308 | Var. 326 | Var. 344 |
| | 75% | Var. 255 | Var. 273 | Var. 291 | Var. 309 | Var. 327 | Var. 345 |
| | 80% | Var. 256 | Var. 274 | Var. 292 | Var. 310 | Var. 328 | Var. 346 |
| | 85% | Var. 257 | Var. 275 | Var. 293 | Var. 311 | Var. 329 | Var. 347 |
| | 90% | Var. 258 | Var. 276 | Var. 294 | Var. 312 | Var. 330 | Var. 348 |
| | 95% | Var. 259 | Var. 277 | Var. 295 | Var. 313 | Var. 331 | Var. 349 |

Var. = Variation

TABLE 7

Exemplary embodiments for the percentage of rVWF molecules that are present in a particular higher order rVWF multimer or larger multimer found in the compositions and used in the methods provided herein.

| | | Minimal Number of Subunits in rVWF Multimer | | | | | |
|---|---|---|---|---|---|---|---|
| | | 30 | 32 | 34 | 36 | 38 | 40 |
| Minimal Percentage of rVWF Molecules | 10% | Var. 350 | Var. 368 | Var. 386 | Var. 404 | Var. 422 | Var. 440 |
| | 15% | Var. 351 | Var. 369 | Var. 387 | Var. 405 | Var. 423 | Var. 441 |
| | 20% | Var. 352 | Var. 370 | Var. 388 | Var. 406 | Var. 424 | Var. 442 |
| | 25% | Var. 353 | Var. 371 | Var. 389 | Var. 407 | Var. 425 | Var. 443 |
| | 30% | Var. 354 | Var. 372 | Var. 390 | Var. 408 | Var. 426 | Var. 444 |
| | 35% | Var. 355 | Var. 373 | Var. 391 | Var. 409 | Var. 427 | Var. 445 |
| | 40% | Var. 356 | Var. 374 | Var. 392 | Var. 410 | Var. 428 | Var. 446 |
| | 45% | Var. 357 | Var. 375 | Var. 393 | Var. 411 | Var. 429 | Var. 447 |
| | 50% | Var. 358 | Var. 376 | Var. 394 | Var. 412 | Var. 430 | Var. 448 |
| | 55% | Var. 359 | Var. 377 | Var. 395 | Var. 413 | Var. 431 | Var. 449 |
| | 60% | Var. 360 | Var. 378 | Var. 396 | Var. 414 | Var. 432 | Var. 450 |
| | 65% | Var. 361 | Var. 379 | Var. 397 | Var. 415 | Var. 433 | Var. 451 |
| | 70% | Var. 362 | Var. 380 | Var. 398 | Var. 416 | Var. 434 | Var. 452 |
| | 75% | Var. 363 | Var. 381 | Var. 399 | Var. 417 | Var. 435 | Var. 453 |

TABLE 7-continued

Exemplary embodiments for the percentage of rVWF molecules that are present in a particular higher order rVWF multimer or larger multimer found in the compositions and used in the methods provided herein.

| | Minimal Number of Subunits in rVWF Multimer | | | | | |
|---|---|---|---|---|---|---|
| | 30 | 32 | 34 | 36 | 38 | 40 |
| 80% | Var. 364 | Var. 382 | Var. 400 | Var. 418 | Var. 436 | Var. 454 |
| 85% | Var. 365 | Var. 383 | Var. 401 | Var. 419 | Var. 437 | Var. 455 |
| 90% | Var. 366 | Var. 384 | Var. 402 | Var. 420 | Var. 438 | Var. 456 |
| 95% | Var. 367 | Var. 385 | Var. 403 | Var. 421 | Var. 439 | Var. 457 |

Var. = Variation

In accordance with the above, the rVWF comprises a significant percentage of high molecular weight (HMW) rVWF multimers. In further embodiments, the BMW rVWF multimer composition comprises at least 10%-80% rVWF decamers or higher order multimers. In further embodiments, the composition comprises about 10-95%, 20-90%, 30-85%, 40-80%, 50-75%, 60-70% decamers or higher order multimers. In further embodiments, the HMW rVWF multimer composition comprises at least about 10%, 20%, 30%, 40%, 50%, 60%, 70%, 80%, 90% decamers or higher order multimers.

Assessment of the number and percentage of rVWF multimers can be conducted using methods known in the art, including without limitation methods using electrophoresis and size exclusion chromatography methods to separate rVWF multimers by size, for example as discussed by Cumming et al, (J Clin Pathol. 1993 May; 46(5): 470-473, which is hereby incorporated by reference in its entirety for all purposes and in particular for all teachings related to assessment of rVWF multimers). Such techniques may further include immunoblotting techniques (such as Western Blot), in which the gel is immunoblotted with a radiolabelled antibody against VWF followed by chemiluminescent detection (see for example Wen et al., (1993), J. Clin. Lab. Anal., 7: 317-323, which is hereby incorporated by reference in its entirety for all purposes and in particular for all teachings related to assessment of rVWF multimers). Further assays for VWF include VWF:Antigen (VWF:Ag), VWF:Ristocetin Cofactor (VWF:RCof), and VWF:Collagen Binding Activity assay (VWF:CBA), which are often used for diagnosis and classification of Von Willebrand Disease. (see for example Favaloro et al., Pathology, 1997, 29(4): 341-456, which is hereby incorporated by reference in its entirety for all purposes and in particular for all teachings related to assays for VWF).

In some embodiments, the ratio of rFVIII procoagulant activity (IU rFVIII:C) to rVWF Ristocetin cofactor activity (IU rVWF:RCo) for the rVWF prepared according to the methods of the present invention is between 3:1 and 1:5. In further embodiments, the ratio is between 2:1 and 1:4. In still further embodiments, the ratio is between 5:2 and 1:4. In further embodiments, the ratio is between 3:2 and 1:3. In still further embodiments, the ratio is about 1:1, 1:2, 1:3, 1:4, 1:5, 2:1, 2:3, 2:4, 2:5, 3:1, 3:2, 3:4, or 3:5. In further embodiments, the ratio is between 1:1 and 1:2. In yet further embodiments, the ratio is 1.1:1, 1.2:1, 1.3:1, 1.4:1, 1.5:1, 1.6:1, 1.7:1, 1.8:1, 1.9:1, or 2:1. In certain embodiments, the ratio of rFVIII procoagulant activity (IU rFVIII:C) to rVWF Ristocetin cofactor activity (IU rVWF:RCo) in a composition useful for a method described herein is selected from variations 1988 to 2140 found in Table 8.

TABLE 8

Exemplary embodiments for the ratio of rFVIII procoagulant activity (IU rFVIII:C) to rVWF Ristocetin cofactor activity (IU rVWF:RCo) in compositions and used in methods provided herein.

| (IU rFVIII:C) to (IU rVWF:RCo) | |
|---|---|
| 4:1 | Var. 1988 |
| 3:1 | Var. 1989 |
| 2:1 | Var. 1990 |
| 3:2 | Var. 1991 |
| 4:3 | Var. 1992 |
| 1:1 | Var. 1993 |
| 5:6 | Var. 1994 |
| 4:5 | Var. 1995 |
| 3:4 | Var. 1996 |
| 2:3 | Var. 1997 |
| 3:5 | Var. 1998 |
| 1:2 | Var. 1999 |
| 2:5 | Var. 2000 |
| 1:3 | Var. 2001 |
| 1:4 | Var. 2002 |
| 1:5 | Var. 2003 |
| 1:6 | Var. 2004 |
| 4:1-1:6 | Var. 2005 |
| 4:1-1:5 | Var. 2006 |
| 4:1-1:4 | Var. 2007 |
| 4:1-1:3 | Var. 2008 |
| 4:1-2:5 | Var. 2009 |
| 4:1-1:2 | Var. 2010 |
| 4:1-3:5 | Var. 2011 |
| 4:1-2:3 | Var. 2012 |
| 4:1-3:4 | Var. 2013 |
| 4:1-4:5 | Var. 2014 |
| 4:1-5:6 | Var. 2015 |
| 4:1-1:1 | Var. 2016 |
| 4:1-4:3 | Var. 2017 |
| 4:1-3:2 | Var. 2018 |
| 4:1-2:1 | Var. 2019 |
| 4:1-3:1 | Var. 2020 |
| 3:1-1:6 | Var. 2021 |
| 3:1-1:5 | Var. 2022 |
| 3:1-1:4 | Var. 2023 |
| 3:1-1:3 | Var. 2024 |
| 3:1-2:5 | Var. 2025 |
| 3:1-1:2 | Var. 2026 |
| 3:1-3:5 | Var. 2027 |
| 3:1-2:3 | Var. 2028 |
| 3:1-3:4 | Var. 2029 |
| 3:1-4:5 | Var. 2030 |
| 3:1-5:6 | Var. 2031 |
| 3:1-1:1 | Var. 2032 |
| 3:1-4:3 | Var. 2033 |
| 3:1-3:2 | Var. 2034 |
| 3:1-2:1 | Var. 2035 |
| 2:1-1:6 | Var. 2036 |
| 2:1-1:5 | Var. 2037 |
| 2:1-1:4 | Var. 2038 |
| 2:1-1:3 | Var. 2039 |
| 2:1-2:5 | Var. 2040 |
| 2:1-1:2 | Var. 2041 |
| 2:1-3:5 | Var. 2042 |
| 2:1-2:3 | Var. 2043 |
| 2:1-3:4 | Var. 2044 |
| 2:1-4:5 | Var. 2045 |
| 2:1-5:6 | Var. 2046 |
| 2:1-1:1 | Var. 2047 |
| 2:1-4:3 | Var. 2048 |
| 2:1-3:2 | Var. 2049 |
| 3:2-1:6 | Var. 2050 |
| 3:2-1:5 | Var. 2051 |
| 3:2-1:4 | Var. 2052 |
| 3:2-1:3 | Var. 2053 |
| 3:2-2:5 | Var. 2054 |
| 3:2-1:2 | Var. 2055 |
| 3:2-3:5 | Var. 2056 |
| 3:2-2:3 | Var. 2057 |
| 3:2-3:4 | Var. 2058 |

TABLE 8-continued

Exemplary embodiments for the ratio of rFVIII procoagulant activity (IU rFVIII:C) to rVWF Ristocetin cofactor activity (IU rVWF:RCo) in compositions and used in methods provided herein.

| (IU rFVIII:C) to (IU rVWF:RCo) | |
|---|---|
| 3:2-4:5 | Var. 2059 |
| 3:2-5:6 | Var. 2060 |
| 3:2-1:1 | Var. 2061 |
| 3:2-4:3 | Var. 2062 |
| 4:3-1:6 | Var. 2063 |
| 4:3-1:5 | Var. 2064 |
| 4:3-1:4 | Var. 2065 |
| 4:3-1:3 | Var. 2066 |
| 4:3-2:5 | Var. 2067 |
| 4:3-1:2 | Var. 2068 |
| 4:3-3:5 | Var. 2069 |
| 4:3-2:3 | Var. 2070 |
| 4:3-3:4 | Var. 2071 |
| 4:3-4:5 | Var. 2072 |
| 4:3-5:6 | Var. 2073 |
| 4:3-1:1 | Var. 2074 |
| 1:1-1:6 | Var. 2075 |
| 1:1-1:5 | Var. 2076 |
| 1:1-1:4 | Var. 2077 |
| 1:1-1:3 | Var. 2078 |
| 1:1-2:5 | Var. 2079 |
| 1:1-1:2 | Var. 2080 |
| 1:1-3:5 | Var. 2081 |
| 1:1-2:3 | Var. 2082 |
| 1:1-3:4 | Var. 2083 |
| 1:1-4:5 | Var. 2084 |
| 1:1-5:6 | Var. 2085 |
| 5:6-1:6 | Var. 2086 |
| 5:6-1:5 | Var. 2087 |
| 5:6-1:4 | Var. 2088 |
| 5:6-1:3 | Var. 2089 |
| 5:6-2:5 | Var. 2090 |
| 5:6-1:2 | Var. 2091 |
| 5:6-3:5 | Var. 2092 |
| 5:6-2:3 | Var. 2093 |
| 5:6-3:4 | Var. 2094 |
| 5:6-4:5 | Var. 2095 |
| 4:5-1:6 | Var. 2096 |
| 4:5-1:5 | Var. 2097 |
| 4:5-1:4 | Var. 2098 |
| 4:5-1:3 | Var. 2099 |
| 4:5-2:5 | Var. 2100 |
| 4:5-1:2 | Var. 2101 |
| 4:5-3:5 | Var. 2102 |
| 4:5-2:3 | Var. 2103 |
| 4:5-3:4 | Var. 2104 |
| 3:4-1:6 | Var. 2105 |
| 3:4-1:5 | Var. 2106 |
| 3:4-1:4 | Var. 2107 |
| 3:4-1:3 | Var. 2108 |
| 3:4-2:5 | Var. 2109 |
| 3:4-1:2 | Var. 2110 |
| 3:4-3:5 | Var. 2111 |
| 3:4-2:3 | Var. 2112 |
| 2:3-1:6 | Var. 2113 |
| 2:3-1:5 | Var. 2114 |
| 2:3-1:4 | Var. 2115 |
| 2:3-1:3 | Var. 2116 |
| 2:3-2:5 | Var. 2117 |
| 2:3-1:2 | Var. 2118 |
| 2:3-3:5 | Var. 2119 |
| 3:5-1:6 | Var. 2120 |
| 3:5-1:5 | Var. 2121 |
| 3:5-1:4 | Var. 2122 |
| 3:5-1:3 | Var. 2123 |
| 3:5-2:5 | Var. 2124 |
| 3:5-1:2 | Var. 2125 |
| 1:2-1:6 | Var. 2126 |
| 1:2-1:5 | Var. 2127 |
| 1:2-1:4 | Var. 2128 |
| 1:2-1:3 | Var. 2129 |
| 1:2-2:5 | Var. 2130 |
| 2:5-1:6 | Var. 2131 |
| 2:5-1:5 | Var. 2132 |
| 2:5-1:4 | Var. 2133 |
| 2:5-1:3 | Var. 2134 |
| 1:3-1:6 | Var. 2135 |
| 1:3-1:5 | Var. 2136 |
| 1:3-1:4 | Var. 2137 |
| 1:4-1:6 | Var. 2138 |
| 1:4-1:5 | Var. 2139 |
| 1:5-1:6 | Var. 2140 |

Var. = Variation

In further embodiments, higher order rVWF multimers of the invention are stable for about 1 to about 90 hours post-administration. In still further embodiments, the higher order rVWF multimers are stable for about 5-80, 10-70, 15-60, 20-50, 25-40, 30-35 hours post-administration. In yet further embodiments, the higher order rVWF multimers are stable for at least 3, 6, 12, 18, 24, 36, 48, 72 hours post-administration. In certain embodiments the stability of the rVWF multimers is assessed in vitro.

In one embodiment, higher order rVWF multimers used in the compositions and methods provided herein have a half-life of at least 12 hour post administration. In another embodiment, the higher order rVWF multimers have a half-life of at least 24 hour post administration. In yet other embodiments, the higher order rVWF multimers have a half-life selected from variations 642 to 1045 found in Table 9.

TABLE 9

Exemplary embodiments for the half-life of higher order rVWF multimers found in the compositions prepared by the methods provided herein.

| Hours | |
|---|---|
| at least 1 | Var. 642 |
| at least 2 | Var. 643 |
| at least 3 | Var. 644 |
| at least 4 | Var. 645 |
| at least 5 | Var. 646 |
| at least 6 | Var. 647 |
| at least 7 | Var. 648 |
| at least 8 | Var. 649 |
| at least 9 | Var. 650 |
| at least 10 | Var. 651 |
| at least 11 | Var. 652 |
| at least 12 | Var. 653 |
| at least 14 | Var. 654 |
| at least 16 | Var. 655 |
| at least 18 | Var. 656 |
| at least 20 | Var. 657 |
| at least 22 | Var. 658 |
| at least 24 | Var. 659 |
| at least 27 | Var. 660 |
| at least 30 | Var. 661 |
| at least 33 | Var. 662 |
| at least 36 | Var. 663 |
| at least 39 | Var. 664 |
| at least 42 | Var. 665 |
| at least 45 | Var. 666 |

TABLE 9-continued

Exemplary embodiments for the half-life of higher order rVWF multimers found in the compositions prepared by the methods provided herein.

| Hours | |
|---|---|
| at least 48 | Var. 667 |
| at least 54 | Var. 668 |
| at least 60 | Var. 669 |
| at least 66 | Var. 670 |
| at least 72 | Var. 671 |
| at least 78 | Var. 672 |
| at least 84 | Var. 673 |
| at least 90 | Var. 674 |
| 2-90 | Var. 675 |
| 2-84 | Var. 676 |
| 2-78 | Var. 677 |
| 2-72 | Var. 678 |
| 2-66 | Var. 679 |
| 2-60 | Var. 680 |
| 2-54 | Var. 681 |
| 2-48 | Var. 682 |
| 2-45 | Var. 683 |
| 2-42 | Var. 684 |
| 2-39 | Var. 685 |
| 2-36 | Var. 686 |
| 2-33 | Var. 687 |
| 2-30 | Var. 688 |
| 2-27 | Var. 689 |
| 2-24 | Var. 690 |
| 2-22 | Var. 691 |
| 2-20 | Var. 692 |
| 2-18 | Var. 693 |
| 2-16 | Var. 694 |
| 2-14 | Var. 695 |
| 2-12 | Var. 696 |
| 2-10 | Var. 697 |
| 2-8 | Var. 698 |
| 2-6 | Var. 699 |
| 2-4 | Var. 700 |
| 3-90 | Var. 701 |
| 3-84 | Var. 702 |
| 3-78 | Var. 703 |
| 3-72 | Var. 704 |
| 3-66 | Var. 705 |
| 3-60 | Var. 706 |
| 3-54 | Var. 707 |
| 3-48 | Var. 708 |
| 3-45 | Var. 709 |
| 3-42 | Var. 710 |
| 3-39 | Var. 711 |
| 3-36 | Var. 712 |
| 3-33 | Var. 713 |
| 3-30 | Var. 714 |
| 3-27 | Var. 715 |
| 3-24 | Var. 716 |
| 3-22 | Var. 717 |
| 3-20 | Var. 718 |
| 3-18 | Var. 719 |
| 3-16 | Var. 720 |
| 3-14 | Var. 721 |
| 3-12 | Var. 722 |
| 3-10 | Var. 723 |
| 3-8 | Var. 724 |
| 3-6 | Var. 725 |
| 3-4 | Var. 726 |
| 4-90 | Var. 727 |
| 4-84 | Var. 728 |
| 4-78 | Var. 729 |
| 4-72 | Var. 730 |
| 4-66 | Var. 731 |
| 4-60 | Var. 732 |
| 4-54 | Var. 733 |
| 4-48 | Var. 734 |
| 4-45 | Var. 735 |
| 4-42 | Var. 736 |
| 4-39 | Var. 737 |
| 4-36 | Var. 738 |
| 4-33 | Var. 739 |
| 4-30 | Var. 740 |
| 4-27 | Var. 741 |
| 4-24 | Var. 742 |
| 4-22 | Var. 743 |
| 4-20 | Var. 744 |
| 4-18 | Var. 745 |
| 4-16 | Var. 746 |
| 4-14 | Var. 747 |
| 4-12 | Var. 748 |
| 4-10 | Var. 749 |
| 4-8 | Var. 750 |
| 4-6 | Var. 751 |
| 6-90 | Var. 752 |
| 6-84 | Var. 753 |
| 6-78 | Var. 754 |
| 6-72 | Var. 755 |
| 6-66 | Var. 756 |
| 6-60 | Var. 757 |
| 6-54 | Var. 758 |
| 6-48 | Var. 759 |
| 6-45 | Var. 760 |
| 6-42 | Var. 761 |
| 6-39 | Var. 762 |
| 6-36 | Var. 763 |
| 6-33 | Var. 764 |
| 6-30 | Var. 765 |
| 6-27 | Var. 766 |
| 6-24 | Var. 767 |
| 6-22 | Var. 768 |
| 6-20 | Var. 769 |
| 6-18 | Var. 770 |
| 6-16 | Var. 771 |
| 6-14 | Var. 772 |
| 6-12 | Var. 773 |
| 6-10 | Var. 774 |
| 6-8 | Var. 775 |
| 8-90 | Var. 776 |
| 8-84 | Var. 777 |
| 8-78 | Var. 778 |
| 8-72 | Var. 779 |
| 8-66 | Var. 780 |
| 8-60 | Var. 781 |
| 8-54 | Var. 782 |
| 8-48 | Var. 783 |
| 8-45 | Var. 784 |
| 8-42 | Var. 785 |
| 8-39 | Var. 786 |
| 8-36 | Var. 787 |
| 8-33 | Var. 788 |
| 8-30 | Var. 789 |
| 8-27 | Var. 790 |
| 8-24 | Var. 791 |
| 8-22 | Var. 792 |
| 8-20 | Var. 793 |
| 8-18 | Var. 794 |
| 8-16 | Var. 795 |
| 8-14 | Var. 796 |
| 8-12 | Var. 797 |
| 8-10 | Var. 798 |
| 10-90 | Var. 799 |
| 10-84 | Var. 800 |
| 10-78 | Var. 801 |
| 10-72 | Var. 802 |
| 10-66 | Var. 803 |
| 10-60 | Var. 804 |
| 10-54 | Var. 805 |
| 10-48 | Var. 806 |
| 10-45 | Var. 807 |
| 10-42 | Var. 808 |
| 10-39 | Var. 809 |
| 10-36 | Var. 810 |
| 10-33 | Var. 811 |
| 10-30 | Var. 812 |

TABLE 9-continued

Exemplary embodiments for the half-life of higher order rVWF multimers found in the compositions prepared by the methods provided herein.

| Hours | |
|---|---|
| 10-27 | Var. 813 |
| 10-24 | Var. 814 |
| 10-22 | Var. 815 |
| 10-20 | Var. 816 |
| 10-18 | Var. 817 |
| 10-16 | Var. 818 |
| 10-14 | Var. 819 |
| 10-12 | Var. 820 |
| 12-90 | Var. 821 |
| 12-84 | Var. 822 |
| 12-78 | Var. 823 |
| 12-72 | Var. 824 |
| 12-66 | Var. 825 |
| 12-60 | Var. 826 |
| 12-54 | Var. 827 |
| 12-48 | Var. 828 |
| 12-45 | Var. 829 |
| 12-42 | Var. 830 |
| 12-39 | Var. 831 |
| 12-36 | Var. 832 |
| 12-33 | Var. 833 |
| 12-30 | Var. 834 |
| 12-27 | Var. 835 |
| 12-24 | Var. 836 |
| 12-22 | Var. 837 |
| 12-20 | Var. 838 |
| 12-18 | Var. 839 |
| 12-16 | Var. 840 |
| 12-14 | Var. 841 |
| 14-90 | Var. 842 |
| 14-84 | Var. 843 |
| 14-78 | Var. 844 |
| 14-72 | Var. 845 |
| 14-66 | Var. 846 |
| 14-60 | Var. 847 |
| 14-54 | Var. 848 |
| 14-48 | Var. 849 |
| 14-45 | Var. 850 |
| 14-42 | Var. 851 |
| 14-39 | Var. 852 |
| 14-36 | Var. 853 |
| 14-33 | Var. 854 |
| 14-30 | Var. 855 |
| 14-27 | Var. 856 |
| 14-24 | Var. 857 |
| 14-22 | Var. 858 |
| 14-20 | Var. 859 |
| 14-18 | Var. 860 |
| 14-16 | Var. 861 |
| 16-90 | Var. 862 |
| 16-84 | Var. 863 |
| 16-78 | Var. 864 |
| 16-72 | Var. 865 |
| 16-66 | Var. 866 |
| 16-60 | Var. 867 |
| 16-54 | Var. 868 |
| 16-48 | Var. 869 |
| 16-45 | Var. 870 |
| 16-42 | Var. 871 |
| 16-39 | Var. 872 |
| 16-36 | Var. 873 |
| 16-33 | Var. 874 |
| 16-30 | Var. 875 |
| 16-27 | Var. 876 |
| 16-24 | Var. 877 |
| 16-22 | Var. 878 |
| 16-20 | Var. 879 |
| 16-18 | Var. 880 |
| 18-90 | Var. 881 |
| 18-84 | Var. 882 |
| 18-78 | Var. 883 |
| 18-72 | Var. 884 |
| 18-66 | Var. 885 |
| 18-60 | Var. 886 |
| 18-54 | Var. 887 |
| 18-48 | Var. 888 |
| 18-45 | Var. 889 |
| 18-42 | Var. 890 |
| 18-39 | Var. 891 |
| 18-36 | Var. 892 |
| 18-33 | Var. 893 |
| 18-30 | Var. 894 |
| 18-27 | Var. 895 |
| 18-24 | Var. 896 |
| 18-22 | Var. 897 |
| 18-20 | Var. 898 |
| 20-90 | Var. 899 |
| 20-84 | Var. 900 |
| 20-78 | Var. 901 |
| 20-72 | Var. 902 |
| 20-66 | Var. 903 |
| 20-60 | Var. 904 |
| 20-54 | Var. 905 |
| 20-48 | Var. 906 |
| 20-45 | Var. 907 |
| 20-42 | Var. 908 |
| 20-39 | Var. 909 |
| 20-36 | Var. 910 |
| 20-33 | Var. 911 |
| 20-30 | Var. 912 |
| 20-27 | Var. 913 |
| 20-24 | Var. 914 |
| 20-22 | Var. 915 |
| 22-90 | Var. 916 |
| 22-84 | Var. 917 |
| 22-78 | Var. 918 |
| 22-72 | Var. 919 |
| 22-66 | Var. 920 |
| 22-60 | Var. 921 |
| 22-54 | Var. 922 |
| 22-48 | Var. 923 |
| 22-45 | Var. 924 |
| 22-42 | Var. 925 |
| 22-39 | Var. 926 |
| 22-36 | Var. 927 |
| 22-33 | Var. 928 |
| 22-30 | Var. 929 |
| 22-27 | Var. 930 |
| 22-24 | Var. 931 |
| 24-90 | Var. 932 |
| 24-84 | Var. 933 |
| 24-78 | Var. 934 |
| 24-72 | Var. 935 |
| 24-66 | Var. 936 |
| 24-60 | Var. 937 |
| 24-54 | Var. 938 |
| 24-48 | Var. 939 |
| 24-45 | Var. 940 |
| 24-42 | Var. 941 |
| 24-39 | Var. 942 |
| 24-36 | Var. 943 |
| 24-33 | Var. 944 |
| 24-30 | Var. 945 |
| 24-27 | Var. 946 |
| 27-90 | Var. 947 |
| 27-84 | Var. 948 |
| 27-78 | Var. 949 |
| 27-72 | Var. 950 |
| 27-66 | Var. 951 |
| 27-60 | Var. 952 |
| 27-54 | Var. 953 |
| 27-48 | Var. 954 |
| 30-90 | Var. 955 |
| 30-84 | Var. 956 |
| 30-78 | Var. 957 |
| 30-72 | Var. 958 |

TABLE 9-continued

Exemplary embodiments for the half-life of higher order rVWF multimers found in the compositions prepared by the methods provided herein.

Hours

| | |
|---|---|
| 30-66 | Var. 959 |
| 30-60 | Var. 960 |
| 30-54 | Var. 961 |
| 30-48 | Var. 962 |
| 30-45 | Var. 963 |
| 30-42 | Var. 964 |
| 30-39 | Var. 965 |
| 30-36 | Var. 966 |
| 30-33 | Var. 967 |
| 33-90 | Var. 968 |
| 33-84 | Var. 969 |
| 33-78 | Var. 970 |
| 33-72 | Var. 971 |
| 33-66 | Var. 972 |
| 33-60 | Var. 973 |
| 33-54 | Var. 974 |
| 33-48 | Var. 975 |
| 33-45 | Var. 976 |
| 33-42 | Var. 977 |
| 33-29 | Var. 978 |
| 33-36 | Var. 979 |
| 36-90 | Var. 980 |
| 36-84 | Var. 981 |
| 36-78 | Var. 982 |
| 36-72 | Var. 983 |
| 36-66 | Var. 984 |
| 36-60 | Var. 985 |
| 36-54 | Var. 986 |
| 36-48 | Var. 987 |
| 36-45 | Var. 988 |
| 36-42 | Var. 989 |
| 36-39 | Var. 990 |
| 39-90 | Var. 991 |
| 39-84 | Var. 992 |
| 39-78 | Var. 993 |
| 39-72 | Var. 994 |
| 39-66 | Var. 995 |
| 39-60 | Var. 996 |
| 39-54 | Var. 997 |
| 39-48 | Var. 998 |
| 39-45 | Var. 999 |
| 39-42 | Var. 1000 |
| 42-90 | Var. 1001 |
| 42-84 | Var. 1002 |
| 42-78 | Var. 1003 |
| 42-72 | Var. 1004 |
| 42-66 | Var. 1005 |
| 42-60 | Var. 1006 |
| 42-54 | Var. 1007 |
| 42-48 | Var. 1008 |
| 42-45 | Var. 1009 |
| 45-90 | Var. 1010 |
| 45-84 | Var. 1011 |
| 45-78 | Var. 1012 |
| 45-72 | Var. 1013 |
| 45-66 | Var. 1014 |
| 45-60 | Var. 1015 |
| 45-54 | Var. 1016 |
| 45-48 | Var. 1017 |
| 48-90 | Var. 1018 |
| 48-84 | Var. 1019 |
| 48-78 | Var. 1020 |
| 48-72 | Var. 1021 |
| 48-66 | Var. 1022 |
| 48-60 | Var. 1023 |
| 48-54 | Var. 1024 |
| 54-90 | Var. 1025 |
| 54-84 | Var. 1026 |
| 54-78 | Var. 1027 |
| 54-72 | Var. 1028 |
| 54-66 | Var. 1029 |
| 54-60 | Var. 1030 |
| 60-90 | Var. 1031 |
| 60-84 | Var. 1032 |
| 60-78 | Var. 1033 |
| 60-72 | Var. 1034 |
| 60-66 | Var. 1035 |
| 66-90 | Var. 1036 |
| 66-84 | Var. 1037 |
| 66-78 | Var. 1038 |
| 66-72 | Var. 1039 |
| 72-90 | Var. 1040 |
| 72-84 | Var. 1041 |
| 72-78 | Var. 1042 |
| 78-90 | Var. 1043 |
| 78-84 | Var. 1044 |
| 84-90 | Var. 1045 |

Var. = Variation

In some embodiments, the pro-VWF and/or purified rVWF purified in accordance with the present invention is not modified with any conjugation, post-translation or covalent modifications. In particular embodiments, the pro-VWF and/or purified rVWF of the present invention is not modified with a water soluble polymer, including without limitation, a polyethylene glycol (PEG), a polypropylene glycol, a polyoxyalkylene, a polysialic acid, hydroxyl ethyl starch, a poly-carbohydrate moiety, and the like.

In some embodiments, the pro-VWF and/or purified rVWF purified in accordance with the present invention is modified through conjugation, post-translation modification, or covalent modification, including modifications of the N- or C-terminal residues as well as modifications of selected side chains, for example, at free sulfhydryl-groups, primary amines, and hydroxyl-groups. In one embodiment, a water soluble polymer is linked to the protein (directly or via a linker) by a lysine group or other primary amine. In some embodiments, the pro-VWF and/or purified rVWF of the present invention may be modified by conjugation of a water soluble polymer, including without limitation, a polyethylene glycol (PEG), a polypropylene glycol, a polyoxyalkylene, a polysialic acid, hydroxyl ethyl starch, a poly-carbohydrate moiety, and the like.

Water soluble polymers that may be used to modify the pro-VWF and/or purified rVWF include linear and branched structures. The conjugated polymers may be attached directly to the coagulation proteins of the invention, or alternatively may be attached through a linking moiety. Non-limiting examples of protein conjugation with water soluble polymers can be found in U.S. Pat. Nos. 4,640,835; 4,496,689; 4,301,144; 4,670,417; 4,791,192, and 4,179,337, as well as in Abuchowski and Davis "Enzymes as Drugs," Holcenberg and Roberts, Eds., pp. 367 383, John Wiley and Sons, New York (1981), and Hermanson G., Bioconjugate Techniques 2nd Ed., Academic Press, Inc. 2008.

Protein conjugation may be performed by a number of well-known techniques in the art, for example, see Hermanson G., Bioconjugate Techniques 2nd Ed., Academic Press, Inc. 2008. Examples include linkage through the peptide bond between a carboxyl group on one of either the coagulation protein or water-soluble polymer moiety and an amine group of the other, or an ester linkage between a carboxyl group of one and a hydroxyl group of the other. Another linkage by which a coagulation protein of the invention could be conjugated to a water-soluble polymer compound is via a Schiff base, between a free amino group on the polymer moiety being reacted with an aldehyde group formed at the non-reducing end of the polymer by periodate oxidation (Jennings and Lugowski, J. Immunol. 1981; 127: 1011-8; Femandes and Gregonradis, Biochim Biophys Acta. 1997; 1341; 26-34). The generated Schiff Base can be stabilized by specific reduction with NaCNBH$_3$ to form a secondary amine. An alternative approach is the generation of terminal free amino groups on the polymer by reductive amination with NH$_4$Cl after prior oxidation. Bifunctional reagents can be used for linking two amino or two hydroxyl groups. For example, a polymer containing an amino group can be coupled to an amino group of the coagulation protein with reagents like BS$_3$ (Bis(sulfosuccinimidyl)suberate/ Pierce, Rockford, Ill.). In addition, heterobifunctional cross linking reagents like Sulfo-EMCS (N-ε-Maleimidocaproyloxy) sulfosuccinimide ester/Pierce) can be used for instance to link amine and thiol groups. In other embodiments, an aldehyde reactive group, such as PEG alkoxide plus diethyl acetal of bromoacetaldehyde; PEG plus DMSO and acetic anhydride, and PEG chloride plus the phenoxide of 4-hydroxybenzaldehyde, succinimidyl active esters, activated dithiocarbonate PEG, 2,4,5-trichlorophenylcloroformate and P-nitrophenylcloroformate activated PEG, may be used in the conjugation of a coagulation protein.

Another method for measuring the biological activity of VWF is the collagen binding assay, which is based on ELISA technology (Brown and Bosak, Thromb. Res., 1986, 43:303-311; Favaloro, Thromb. Haemost., 2000, 83 127-135). A microtiter plate is coated with type I or III collagen. Then the VWF is bound to the collagen surface and subsequently detected with an enzyme-labeled polyclonal antibody. The last step is a substrate reaction, which can be photometrically monitored with an ELISA reader.

Immunological assays of von Willebrand factors (VWF: Ag) are immunoassays that measure the concentration of the VWF protein in plasma. They give no indication as to VWF function. A number of methods exist for measuring VWF:Ag and these include both enzyme-linked immunosorbent assay (ELISA) or automated latex immunoassays (LIA.) Many laboratories now use a fully automated latex immunoassay. Historically laboratories used a variety of techniques including Laurell electroimmunoassay 'Laurell Rockets' but these are rarely used in most labs today.

III. Kits

As an additional aspect, the invention includes kits which comprise one or more lyophilized compositions packaged in a manner which facilitates their use for administration to subjects. In one embodiment, such a kit includes pharmaceutical formulation described herein (e.g., a composition comprising a therapeutic protein or peptide), packaged in a container such as a sealed bottle or vessel, with a label affixed to the container or included in the package that describes use of the compound or composition in practicing the method. In one embodiment, the pharmaceutical formulation is packaged in the container such that the amount of headspace in the container (e.g., the amount of air between the liquid formulation and the top of the container) is very small. Preferably, the amount of headspace is negligible (e.g., almost none). In one embodiment, the kit contains a first container having a therapeutic protein or peptide composition and a second container having a physiologically acceptable reconstitution solution for the composition. In one aspect, the pharmaceutical formulation is packaged in a unit dosage form. The kit may further include a device suitable for administering the pharmaceutical formulation according to a specific route of administration. Preferably, the kit contains a label that describes use of the pharmaceutical formulations.

IV. rVWF for Methods of Prophylactic Treatment of Spontaneous Bleeding in Patients with Severe VWD One of the advantages of administering rVWF to subjects with severe VWD for prophylactic treatment of spontaneous bleeding episodes is that the higher specific activity of rVWF as compared to pdVWF allows for flexibility in the amount of rVWF administered and the number of times the subject is re-dosed. As will be appreciated and as is discussed in further detail herein, the co-administered FVIII may be recombinant or plasma derived.

Single or multiple administrations of rVWF are carried out with the dose levels and pattern being selected by the treating physician. For the prevention or treatment of disease, the appropriate dosage depends on the type of disease to be treated (e.g., von Willebrand disease), the severity and course of the disease, whether drug is administered for preventive or therapeutic purposes, previous therapy, the patient's clinical history and response to the drug, and the discretion of the attending physician.

In some aspects, rVWF is administered prophylactically to a subject at a dose ranging from 40-80 IU/kg, e.g., 40, 41, 42, 43, 44, 45, 46, 47, 48, 49, 50, 51, 52, 53, 54, 55, 56, 57, 58, 59, 60, 60, 61, 62, 63, 64, 65, 66, 67, 68, 69, 70, 71, 72, 73, 74, 75, 76, 77, 78, 79, 80, 40-80, 45-80, 50-80, 45-70, 45-60, 45-55, 45-50, 50-60, 55-60, 60-65, 55-65, 60-70, 65-70, 60-75, 70-80, or 75-80 IU/kg. In some embodiments, the dose ranges from 40 IU/kg to 60 IU/kg. In some embodiments, the dose ranges from 45 IU/kg to 55 IU/kg. In some embodiments, the dose is about 40 IU/kg, about 50 IU/kg, or about 60 IU/kg. In some embodiments, the dose is about 50 IU/kg. In some embodiments, the dose is about 80 IU/kg. In some embodiments, rVWF is administered once a week, two times a week, three times a week, four times a week, five times a week, or more. In some embodiments, rVWF is administered twice a week. In some embodiments, rVWF is administered twice a week. In some embodiments, rVWF is administered twice a week as a dose ranging from 40 IU/kg to 60 IU/kg. In some embodiments, rVWF is administered twice a week as a dose ranging from 40 IU/kg to 60 IU/kg by IV infusion.

In some embodiments, blood samples to measure vWF: Ag, vWF:RCo, vWF:CB and FVIII activity levels were taken pre-dose, at 15 minutes, 30 minutes, and 60 minutes after drug infusion, and at 3 hours, 6 hours, 12 hours, 24 hours, 28 hours, 32 hours, 48 hours, 72 hours, and 96 hours. In some embodiments, samples, including for example blood samples, can be obtained for examining vWF:RCo and FVIII activity. In some embodiments, samples for FVIII, FVIII:C, VWF:RCo, VWF:Ag, and VWF collagen-binding capacity activity are obtained prior to the prophylactic treatment with rVWF. In some embodiments, samples for examining FVIII, FVIII:C, VWF:RCo, VWF:Ag, and VWF collagen-binding capacity activity are obtained 15 minutes, 30 minutes, 60 minutes, 3 hours, 6 hours, 12 hours, 24 hours, 28 hours, 32 hours, 48 hours, 72 hours, or 96 hours, after prophylactic treatment with rVWF. In some embodiments, samples for examining FVIII, FVIII:C, VWF:RCo, VWF: Ag, and VWF collagen-binding capacity activity are obtained 25 to 31 days after prophylactic treatment with rVWF. In some embodiments, samples for FVIII, FVIII:C, VWF:RCo, VWF:Ag, and VWF collagen-binding capacity activity are obtained after a bleeding episode and in such embodiments, a sample is take prior to rVWF administration, 2 hours after administrator and then every 12-24 hours until resolution of the bleeding event. In some embodiments, FVIII, FVIII:C, VWF:RCo, VWF:Ag, and VWF collagen-binding capacity activity versus time profiles are determined based on the samples. In some embodiments, FVIII:C is also measured by a 1-stage clotting assay versus time profiles.

In some embodiments, rVWF is administered to the subject at a range of 40-80 IU/kg, e.g., 40, 41, 42, 43, 44, 45, 46, 47, 48, 49, 50, 51, 52, 53, 54, 55, 56, 57, 58, 59, 60, 60, 61, 62, 63, 64, 65, 66, 67, 68, 69, 70, 71, 72, 73, 74, 75, 76, 77, 78, 79, 80, 40-80, 45-80, 50-80, 45-70, 45-60, 45-55, 45-50, 50-60, 55-60, 60-65, 55-65, 60-70, 65-70, 60-75, 70-80, or 75-80 IU/kg as an initial (first) administration. In some embodiments, rVWF is administered to the subject at a range of 40-80 IU/kg, e.g., 40, 41, 42, 43, 44, 45, 46, 47, 48, 49, 50, 51, 52, 53, 54, 55, 56, 57, 58, 59, 60, 60, 61, 62, 63, 64, 65, 66, 67, 68, 69, 70, 71, 72, 73, 74, 75, 76, 77, 78, 79, 80, 40-80, 45-80, 50-80, 45-70, 45-60, 45-55, 45-50, 50-60, 55-60, 60-65, 55-65, 60-70, 65-70, 60-75, 70-80, or 75-80 IU/kg as a second administration. In some embodiments, rVWF is administered to the subject at a range of 40-80 IU/kg, e.g., 40, 41, 42, 43, 44, 45, 46, 47, 48, 49, 50, 51, 52, 53, 54, 55, 56, 57, 58, 59, 60, 60, 61, 62, 63, 64, 65, 66, 67, 68, 69, 70, 71, 72, 73, 74, 75, 76, 77, 78, 79, 80, 40-80, 45-80, 50-80, 45-70, 45-60, 45-55, 45-50, 50-60, 55-60, 60-65, 55-65, 60-70, 65-70, 60-75, 70-80, or 75-80 IU/kg as a third administration. In some embodiments, rVWF is administered to the subject at a range of 40-80 IU/kg, e.g., 40, 41, 42, 43, 44, 45, 46, 47, 48, 49, 50, 51, 52, 53, 54, 55, 56, 57, 58, 59, 60, 60, 61, 62, 63, 64, 65, 66, 67, 68, 69, 70, 71, 72, 73, 74, 75, 76, 77, 78, 79, 80, 40-80, 45-80, 50-80, 45-70, 45-60, 45-55, 45-50, 50-60, 55-60, 60-65, 55-65, 60-70, 65-70, 60-75, 70-80, or 75-80 IU/kg as a subsequent administration.

Compositions of rVWF can be contained in pharmaceutical formulations, as described herein. Such formulations can be administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramuscular, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient.

In one aspect, formulations of the invention are administered by an initial bolus followed by a continuous infusion to maintain therapeutic circulating levels of drug product. As another example, the inventive compound is administered as a one-time dose. Those of ordinary skill in the art will readily optimize effective dosages and administration regimens as determined by good medical practice and the clinical condition of the individual patient. The route of administration can be, but is not limited to, by intravenous, intraperitoneal, subcutaneous, or intramuscular administration. The frequency of dosing depends on the pharmacokinetic parameters of the agents and the route of administration. The optimal pharmaceutical formulation is determined by one skilled in the art depending upon the route of administration and desired dosage. See for example, Remington's Pharmaceutical Sciences, 18th Ed., 1990, Mack Publishing Co., Easton, Pa. 18042 pages 1435-1712, the disclosure of which is hereby incorporated by reference in its entirety for all purposes and in particular for all teachings related to formulations, routes of administration and dosages for pharmaceutical products. Such formulations influence the physical state, stability, rate of in vivo release, and rate of in vivo clearance of the administered agents. Depending on the route of administration, a suitable dose is calculated according to body weight, body surface area or organ size. Appropriate dosages may be ascertained through use of established assays for determining blood level dosages in conjunction with appropriate dose-response data. The final dosage regimen is determined by the attending physician, considering various factors which modify the action of drugs, e.g. the drug's specific activity, the severity of the damage and the responsiveness of the patient, the age, condition, body weight, sex and diet of the patient, the severity of any infection, time of administration and other clinical factors. By way of example, a typical dose of a recombinant VWF of the present invention is approximately 50 IU/kg, equal to 500 µg/kg. As studies are conducted, further information will emerge regarding the appropriate dosage levels and duration of treatment for various diseases and conditions.

To administer compositions to human or test animals, in one aspect, the compositions comprises one or more pharmaceutically acceptable carriers. The phrases "pharmaceutically" or "pharmacologically" acceptable refer to molecular entities and compositions that are stable, inhibit protein degradation such as aggregation and cleavage products, and in addition do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like, including those agents disclosed above.

The pharmaceutical formulations are administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramusclar, intramammary, intraperitoneal, intrathecal, retrobulbar, and/or intrapulmonary injection at a particular site is contemplated as well. Generally, compositions are essentially free of pyrogens, as well as other impurities that could be harmful to the recipient.

Single or multiple administrations of rVWF are carried out with the dose levels and pattern being selected by the treating physician. For the prevention or treatment of disease, the appropriate dosage depends on the type of disease to be treated (e.g., von Willebrand disease), the severity and course of the disease, whether drug is administered for preventive or therapeutic purposes, previous therapy, the patient's clinical history and response to the drug, and the discretion of the attending physician.

a. Lyophilized VWF Formulations

The present method also provides formulations of rVWF for use in the treatment methods provided herein. In some embodiments, the rVWF composition is used for the production of a pharmaceutical composition. In some embodiments, the rVWF can be formulated into a lyophilized formulation.

In some embodiments, the formulations comprising a VWF polypeptide of the invention are lyophilized after purification and prior to administration to a subject. Lyophilization is carried out using techniques common in the art and should be optimized for the composition being developed (Tang et al., Pharm Res. 21:191-200, (2004) and Chang et al., Pharm Res. 13:243-9 (1996)).

A lyophilization cycle is, in one aspect, composed of three steps: freezing, primary drying, and secondary drying (A. P. Mackenzie, Phil Trans R Soc London, Ser B, Biol 278:167 (1977)). In the freezing step, the solution is cooled to initiate ice formation. Furthermore, this step induces the crystallization of the bulking agent. The ice sublimes in the primary drying stage, which is conducted by reducing chamber pressure below the vapor pressure of the ice, using a vacuum and introducing heat to promote sublimation. Finally, adsorbed or bound water is removed at the secondary drying stage under reduced chamber pressure and at an elevated shelf temperature. The process produces a material known as a lyophilized cake. Thereafter the cake can be reconstituted with either sterile water or suitable diluent for injection.

The lyophilization cycle not only determines the final physical state of excipients but also affects other parameters such as reconstitution time, appearance, stability and final moisture content. The composition structure in the frozen state proceeds through several transitions (e.g., glass transitions, wettings, and crystallizations) that occur at specific temperatures and the structure may be used to understand and optimize the lyophilization process. The glass transition temperature (Tg and/or Tg') can provide information about the physical state of a solute and can be determined by differential scanning calorimetry (DSC). Tg and Tg' are an important parameter that must be taken into account when designing the lyophilization cycle. For example, Tg' is important for primary drying. Furthermore, in the dried state, the glass transition temperature provides information on the storage temperature of the final product.

b. Pharmaceutical Formulations and Excipients in General

Excipients are additives that either impart or enhance the stability and delivery of a drug product (e.g., protein). Regardless of the reason for their inclusion, excipients are an integral component of a formulation and therefore need to be safe and well tolerated by patients. For protein drugs, the choice of excipients is particularly important because they can affect both efficacy and immunogenicity of the drug. Hence, protein formulations need to be developed with appropriate selection of excipients that afford suitable stability, safety, and marketability.

A lyophilized formulation is, in one aspect, at least comprised of one or more of a buffer, a bulking agent, and a stabilizer. In this aspect, the utility of a surfactant is evaluated and selected in cases where aggregation during the lyophilization step or during reconstitution becomes an issue. An appropriate buffering agent is included to maintain the formulation within stable zones of pH during lyophilization. A comparison of the excipient components contemplated for liquid and lyophilized protein formulations is provided in Table 10.

TABLE 10

Excipient components of lyophilized protein formulations

| Excipient component | Function in lyophilized formulation |
| --- | --- |
| Buffer | Maintain pH of formulation during lyophilization and upon reconstitution |
| Tonicity agent/stabilizer | Stabilizers include cryo and lycoprotectants<br>Examples include Polyols, sugars and polymers<br>Cryoprotectants protect proteins from freezing stresses<br>Lyoprotectants stabilize proteins in the freeze-dried state |
| Bulking agent | Used to enhance product elegance and to prevent blowout<br>Provides structural strength to the lyo cake<br>Examples include mannitol and glycine |
| Surfactant | Employed if aggregation during the lyophilization process is an issue<br>May serve to reduce reconstitution times<br>Examples include polysorbate 20 and 80 |
| Anti-oxidant | Usually not employed, molecular reactions in the lyo cake are generally retarded |
| Metal ions/chelating agent | May be included if a specific metal ion is included only as a co-factor of where the metal is required for protease activity<br>Chelating agents are generally not needed in lyo formulations |
| Preservative | For multi-dose formulations only<br>Provides protection against microbial growth in formulation<br>Is usually included in the reconstitution diluent (e.g., bWFI) |

The principal challenge in developing formulations for proteins is stabilizing the product against the stresses of manufacturing, shipping and storage. The role of formulation excipients is to provide stabilization against these stresses. Excipients are also employed to reduce viscosity of high concentration protein formulations in order to enable their delivery and enhance patient convenience. In general, excipients can be classified on the basis of the mechanisms by which they stabilize proteins against various chemical and physical stresses. Some excipients are used to alleviate the effects of a specific stress or to regulate a particular susceptibility of a specific protein. Other excipients have more general effects on the physical and covalent stabilities of proteins. The excipients described herein are organized either by their chemical type or their functional role in formulations. Brief descriptions of the modes of stabilization are provided when discussing each excipient type.

Given the teachings and guidance provided herein, those skilled in the art will know what amount or range of excipient can be included in any particular formulation to achieve a biopharmaceutical formulation of the invention that promotes retention in stability of the biopharmaceutical (e.g., a protein). For example, the amount and type of a salt to be included in a biopharmaceutical formulation of the invention is selected based on the desired osmolality (e.g., isotonic, hypotonic or hypertonic) of the final solution as well as the amounts and osmolality of other components to be included in the formulation.

By way of example, inclusion of about 5% sorbitol can achieve isotonicity while about 9% of a sucrose excipient is needed to achieve isotonicity. Selection of the amount or range of concentrations of one or more excipients that can be included within a biopharmaceutical formulation of the invention has been exemplified above by reference to salts, polyols and sugars. However, those skilled in the art will understand that the considerations described herein and further exemplified by reference to specific excipients are equally applicable to all types and combinations of excipients including, for example, salts, amino acids, other tonicity agents, surfactants, stabilizers, bulking agents, cryoprotectants, lyoprotectants, anti-oxidants, metal ions, chelating agents and/or preservatives.

Further, where a particular excipient is reported in molar concentration, those skilled in the art will recognize that the equivalent percent (%) w/v (e.g., (grams of substance in a solution sample/mL of solution)×100%) of solution is also contemplated.

Of course, a person having ordinary skill in the art would recognize that the concentrations of the excipients described herein share an interdependency within a particular formulation. By way of example, the concentration of a bulking agent may be lowered where, e.g., there is a high protein concentration or where, e.g., there is a high stabilizing agent concentration. In addition, a person having ordinary skill in the art would recognize that, in order to maintain the isotonicity of a particular formulation in which there is no bulking agent, the concentration of a stabilizing agent would be adjusted accordingly (e.g., a "tonicifying" amount of stabilizer would be used). Common excipients are known in the art and can be found in Powell et al., Compendium of Excipients for Parenteral Formulations (1998), PDA J. Pharm. Sci. Technology, 52:238-311.

c. Pharmaceutical Buffers and Buffering Agents

The stability of a pharmacologically active protein formulation is usually observed to be maximal in a narrow pH range. This pH range of optimal stability needs to be identified early during pre-formulation studies. Several approaches, such as accelerated stability studies and calorimetric screening studies, are useful in this endeavor (Remmele R. L. Jr., et al., Biochemistry, 38(16): 5241-7 (1999)). Once a formulation is finalized, the protein must be manufactured and maintained throughout its shelf-life. Hence, buffering agents are almost always employed to control pH in the formulation.

The buffer capacity of the buffering species is maximal at a pH equal to the pKa and decreases as pH increases or decreases away from this value. Ninety percent of the buffering capacity exists within one pH unit of its pKa. Buffer capacity also increases proportionally with increasing buffer concentration.

Several factors need to be considered when choosing a buffer. First and foremost, the buffer species and its concentration need to be defined based on its pKa and the desired formulation pH. Equally important is to ensure that the buffer is compatible with the protein and other formulation excipients, and does not catalyze any degradation reactions. A third important aspect to be considered is the sensation of stinging and irritation the buffer may induce upon administration. For example, citrate is known to cause stinging upon injection (Laursen T, et al., Basic Clin Pharmacol Toxicol., 98(2): 218-21 (2006)). The potential for stinging and irritation is greater for drugs that are administered via the subcutaneous (SC) or intramuscular (IM) routes, where the drug solution remains at the site for a relatively longer period of time than when administered by the IV route where the formulation gets diluted rapidly into the blood upon administration. For formulations that are administered by direct IV infusion, the total amount of buffer (and any other formulation component) needs to be monitored. One has to be particularly careful about potassium ions administered in the form of the potassium phosphate buffer, which can induce cardiovascular effects in a patient (Hollander-Rodriguez J C, et al., Am. Fam. Physician., 73(2): 283-90 (2006)).

Buffers for lyophilized formulations need additional consideration. Some buffers like sodium phosphate can crystallize out of the protein amorphous phase during freezing resulting in shifts in pH. Other common buffers such as acetate and imidazole may sublime or evaporate during the lyophilization process, thereby shifting the pH of formulation during lyophilization or after reconstitution.

The buffer system present in the compositions is selected to be physiologically compatible and to maintain a desired pH of the pharmaceutical formulation. In one embodiment, the pH of the solution is between pH 2.0 and pH 12.0. For example, the pH of the solution may be 2.0, 2.3, 2.5, 2.7, 3.0, 3.3, 3.5, 3.7, 4.0, 4.3, 4.5, 4.7, 5.0, 5.3, 5.5, 5.7, 6.0, 6.3, 6.5, 6.7, 7.0, 7.3, 7.5, 7.7, 8.0, 8.3, 8.5, 8.7, 9.0, 9.3, 9.5, 9.7, 10.0, 10.3, 10.5, 10.7, 11.0, 11.3, 11.5, 11.7, or 12.0.

The pH buffering compound may be present in any amount suitable to maintain the pH of the formulation at a predetermined level. In one embodiment, the pH buffering concentration is between 0.1 mM and 500 mM (1 M). For example, it is contemplated that the pH buffering agent is at least 0.1, 0.5, 0.7, 0.8 0.9, 1.0, 1.2, 1.5, 1.7, 2, 3, 4, 5, 6, 7, 8, 9, 10, 11, 12, 13, 14, 15, 16, 17, 18, 19, 20, 25, 30, 40, 50, 60, 70, 80, 90, 100, 200, or 500 mM.

Exemplary pH buffering agents used to buffer the formulation as set out herein include, but are not limited to organic acids, glycine, histidine, glutamate, succinate, phosphate, acetate, citrate, Tris, HEPES, and amino acids or mixtures of amino acids, including, but not limited to aspartate, histidine, and glycine. In one embodiment of the present invention, the buffering agent is citrate.

d. Pharmaceutical Stabilizers and Bulking Agents

In one aspect of the present pharmaceutical formulations, a stabilizer (or a combination of stabilizers) is added to prevent or reduce storage-induced aggregation and chemical degradation. A hazy or turbid solution upon reconstitution indicates that the protein has precipitated or at least aggregated. The term "stabilizer" means an excipient capable of preventing aggregation or physical degradation, including chemical degradation (for example, autolysis, deamidation, oxidation, etc.) in an aqueous state. Stabilizers contemplated include, but are not limited to, sucrose, trehalose, mannose, maltose, lactose, glucose, raffinose, cellobiose, gentiobiose, isomaltose, arabinose, glucosamine, fructose, mannitol, sorbitol, glycine, arginine HCL, poly-hydroxy compounds, including polysaccharides such as dextran, starch, hydroxyethyl starch, cyclodextrins, N-methyl pyrollidene, cellulose and hyaluronic acid, sodium chloride, (Carpenter et al., Develop. Biol. Standard 74:225, (1991)). In the present formulations, the stabilizer is incorporated in a concentration of about 0.1, 0.5, 0.7, 0.8 0.9, 1.0, 1.2, 1.5, 1.7, 2, 3, 4, 5, 6, 7, 8, 9, 10, 11, 12, 13, 14, 15, 16, 17, 18, 19, 20, 30, 40, 50, 60, 70, 80, 90, 100, 200, 500, 700, 900, or 1000 mM. In one embodiment of the present invention, mannitol and trehalose are used as stabilizing agents.

If desired, the formulations also include appropriate amounts of bulking and osmolality regulating agents. Bulking agents include, for example and without limitation, mannitol, glycine, sucrose, polymers such as dextran, polyvinylpyrolidone, carboxymethylcellulose, lactose, sorbitol, trehalose, or xylitol. In one embodiment, the bulking agent is mannitol. The bulking agent is incorporated in a concentration of about 0.1, 0.5, 0.7, 0.8 0.9, 1.0, 1.2, 1.5, 1.7, 2, 3, 4, 5, 6, 7, 8, 9, 10, 11, 12, 13, 14, 15, 16, 17, 18, 19, 20, 30, 40, 50, 60, 70, 80, 90, 100, 200, 500, 700, 900, or 1000 mM.

e. Pharmaceutical Surfactants

Proteins have a high propensity to interact with surfaces making them susceptible to adsorption and denaturation at air-liquid, vial-liquid, and liquid-liquid (silicone oil) interfaces. This degradation pathway has been observed to be inversely dependent on protein concentration and results in either the formation of soluble and insoluble protein aggregates or the loss of protein from solution via adsorption to surfaces. In addition to container surface adsorption, surface-induced degradation is exacerbated with physical agitation, as would be experienced during shipping and handling of the product.

Surfactants are commonly used in protein formulations to prevent surface-induced degradation. Surfactants are amphipathic molecules with the capability of out-competing proteins for interfacial positions. Hydrophobic portions of the surfactant molecules occupy interfacial positions (e.g., air/liquid), while hydrophilic portions of the molecules remain oriented towards the bulk solvent. At sufficient concentrations (typically around the detergent's critical micellar concentration), a surface layer of surfactant molecules serves to prevent protein molecules from adsorbing at the interface. Thereby, surface-induced degradation is minimized. Surfactants contemplated herein include, without limitation, fatty acid esters of sorbitan polyethoxylates, e.g., polysorbate 20 and polysorbate 80. The two differ only in the length of the aliphatic chain that imparts hydrophobic character to the molecules, C-12 and C-18, respectively. Accordingly, polysorbate-80 is more surface-active and has a lower critical micellar concentration than polysorbate-20.

Detergents can also affect the thermodynamic conformational stability of proteins. Here again, the effects of a given detergent excipient will be protein specific. For example, polysorbates have been shown to reduce the stability of some proteins and increase the stability of others. Detergent destabilization of proteins can be rationalized in terms of the hydrophobic tails of the detergent molecules that can engage in specific binding with partially or wholly unfolded protein states. These types of interactions could cause a shift in the conformational equilibrium towards the more expanded protein states (e.g. increasing the exposure of hydrophobic portions of the protein molecule in complement to binding polysorbate). Alternatively, if the protein native state exhibits some hydrophobic surfaces, detergent binding to the native state may stabilize that conformation.

Another aspect of polysorbates is that they are inherently susceptible to oxidative degradation. Often, as raw materials, they contain sufficient quantities of peroxides to cause oxidation of protein residue side-chains, especially methionine. The potential for oxidative damage arising from the addition of stabilizer emphasizes the point that the lowest effective concentrations of excipients should be used in formulations. For surfactants, the effective concentration for a given protein will depend on the mechanism of stabilization.

Surfactants are also added in appropriate amounts to prevent surface related aggregation phenomenon during freezing and drying (Chang, B, J. Pharm. Sci. 85:1325, (1996)). Thus, exemplary surfactants include, without limitation, anionic, cationic, nonionic, zwitterionic, and amphoteric surfactants including surfactants derived from naturally-occurring amino acids. Anionic surfactants include, but are not limited to, sodium lauryl sulfate, dioctyl sodium sulfo succinate and dioctyl sodium sulfonate, chenodeoxycholic acid, N-lauroylsarcosine sodium salt, lithium dodecyl sulfate, 1-octanesulfonic acid sodium salt, sodium cholate hydrate, sodium deoxycholate, and glycodeoxycholic acid sodium salt. Cationic surfactants include, but are not limited to, benzalkonium chloride or benzethonium chloride, cetylpyridinium chloride monohydrate, and hexadecyltrimethylammonium bromide. Zwitterionic surfactants include, but are not limited to, CHAPS, CHAPSO, SB3-10, and SB3-12. Non-ionic surfactants include, but are not limited to, digitonin, Triton X-100, Triton X-114, TWEEN-20, and TWEEN-80. Surfactants also include, but are not limited to lauromacrogol 400, polyoxyl 40 stearate, polyoxyethylene hydrogenated castor oil 10, 40, 50 and 60, glycerol monostearate, polysorbate 40, 60, 65 and 80, soy lecithin and other phospholipids such as dioleyl phosphatidyl choline (DOPC), dimyristoylphosphatidyl glycerol (DMPG), dimyristoylphosphatidyl choline (DMPC), and (dioleyl phosphatidyl glycerol) DOPG; sucrose fatty acid ester, methyl cellulose and carboxymethyl cellulose. Compositions comprising these surfactants, either individually or as a mixture in different ratios, are therefore further provided. In one embodiment of the present invention, the surfactant is TWEEN-80. In the present formulations, the surfactant is incorporated in a concentration of about 0.01 to about 0.5 g/L. In formulations provided, the surfactant concentration is 0.005, 0.01, 0.02, 0.03, 0.05, 0.06, 0.07, 0.08, 0.09, 0.1, 0.2, 0.3, 0.4, 0.5, 0.6, 0.7, 0.8, 0.9 or 1.0 g/L.

f. Pharmaceutical Salts

Salts are often added to increase the ionic strength of the formulation, which can be important for protein solubility, physical stability, and isotonicity. Salts can affect the physical stability of proteins in a variety of ways. Ions can stabilize the native state of proteins by binding to charged residues on the protein's surface. Alternatively, salts can stabilize the denatured state by binding to peptide groups along the protein backbone (—CONH—). Salts can also stabilize the protein native conformation by shielding repulsive electrostatic interactions between residues within a protein molecule. Salts in protein formulations can also shield attractive electrostatic interactions between protein molecules that can lead to protein aggregation and insolubility. In formulations provided, the salt concentration is between 0.1, 1, 10, 20, 30, 40, 50, 80, 100, 120, 150, 200, 300, and 500 mM.

g. Other Common Excipient Components: Pharmaceutical Amino Acids

Amino acids have found versatile use in protein formulations as buffers, bulking agents, stabilizers and antioxidants. Thus, in one aspect histidine and glutamic acid are employed to buffer protein formulations in the pH range of 5.5-6.5 and 4.0-5.5 respectively. The imidazole group of histidine has a pKa=6.0 and the carboxyl group of glutamic acid side chain has a pKa of 4.3 which makes these amino acids suitable for buffering in their respective pH ranges. Glutamic acid is particularly useful in such cases. Histidine is commonly found in marketed protein formulations, and this amino acid provides an alternative to citrate, a buffer known to sting upon injection. Interestingly, histidine has also been reported to have a stabilizing effect, with respect to aggregation when used at high concentrations in both liquid and lyophilized presentations (Chen B, et al., Pharm Res., 20(12): 1952-60 (2003)). Histidine was also observed by others to reduce the viscosity of a high protein concentration formulation. However, in the same study, the authors observed increased aggregation and discoloration in histidine containing formulations during freeze-thaw studies of the antibody in stainless steel containers. Another note of caution with histidine is that it undergoes photo-oxidation in the presence of metal ions (Tomita M, et al., Biochemistry, 8(12): 5149-60 (1969)). The use of methionine as an antioxidant in formulations appears promising; it has been observed to be effective against a number of oxidative stresses (Lam X M, et al., J Pharm ScL, 86(11): 1250-5 (1997)).

In various aspects, formulations are provided which include one or more of the amino acids glycine, proline, serine, arginine and alanine have been shown to stabilize proteins by the mechanism of preferential exclusion. Glycine is also a commonly used bulking agent in lyophilized formulations. Arginine has been shown to be an effective agent in inhibiting aggregation and has been used in both liquid and lyophilized formulations.

In formulations provided, the amino acid concentration is between 0.1, 1, 10, 20, 30, 40, 50, 80, 100, 120, 150, 200, 300, and 500 mM. In one embodiment of the present invention, the amino acid is glycine.

h. Other Common Excipient Components: Pharmaceutical Antioxidants

Oxidation of protein residues arises from a number of different sources. Beyond the addition of specific antioxidants, the prevention of oxidative protein damage involves the careful control of a number of factors throughout the manufacturing process and storage of the product such as atmospheric oxygen, temperature, light exposure, and chemical contamination. The invention therefore contemplates the use of the pharmaceutical antioxidants including, without limitation, reducing agents, oxygen/free-radical scavengers, or chelating agents. Antioxidants in therapeutic protein formulations are, in one aspect, water-soluble and remain active throughout the product shelf-life. Reducing agents and oxygen/free-radical scavengers work by ablating active oxygen species in solution. Chelating agents such as EDTA are effective by binding trace metal contaminants that promote free-radical formation. For example, EDTA was utilized in the liquid formulation of acidic fibroblast growth factor to inhibit the metal ion catalyzed oxidation of cysteine residues.

In addition to the effectiveness of various excipients to prevent protein oxidation, the potential for the antioxidants themselves to induce other covalent or physical changes to the protein is of concern. For example, reducing agents can cause disruption of intramolecular disulfide linkages, which can lead to disulfide shuffling. In the presence of transition metal ions, ascorbic acid and EDTA have been shown to promote methionine oxidation in a number of proteins and peptides (Akers M J, and Defelippis M R. Peptides and Proteins as Parenteral Solutions. In: Pharmaceutical Formulation Development of Peptides and Proteins. Sven Frokjaer, Lars Hovgaard, editors. Pharmaceutical Science. Taylor and Francis, UK (1999)); Fransson J. R., /. Pharm. Sci. 86(9): 4046-1050 (1997); Yin J, et al., Pharm Res., 21(12): 2377-83 (2004)). Sodium thiosulfate has been reported to reduce the levels of light and temperature induced methionine-oxidation in rhuMab HER2; however, the formation of a thiosulfate-protein adduct was also reported in this study (Lam X M, Yang J Y, et al., J Pharm Sci. 86(11): 1250-5 (1997)). Selection of an appropriate antioxidant is made according to the specific stresses and sensitivities of the protein. Antioxidants contemplated in certain aspects include, without limitation, reducing agents and oxygen/free-radical scavengers, EDTA, and sodium thiosulfate.

i. Other Common Excipient Components: Pharmaceutical Metal Ions

In general, transition metal ions are undesired in protein formulations because they can catalyze physical and chemical degradation reactions in proteins. However, specific metal ions are included in formulations when they are co-factors to proteins and in suspension formulations of proteins where they form coordination complexes (e.g., zinc suspension of insulin). Recently, the use of magnesium ions (10-120 mM) has been proposed to inhibit the isomerization of aspartic acid to isoaspartic acid (WO 2004039337).

Two examples where metal ions confer stability or increased activity in proteins are human deoxyribonuclease (rhDNase, Pulmozyme®), and Factor VIII. In the case of rhDNase, Ca' ions (up to 100 mM) increased the stability of the enzyme through a specific binding site (Chen B, et al., Pharm Sci., 88(4): 477-82 (1999)). In fact, removal of calcium ions from the solution with EGTA caused an increase in deamidation and aggregation. However, this effect was observed only with $Ca^{+2}$ ions; other divalent cations $Mg^{+2}$, $Mn^{+2}$ and $Zn^{+2}$ were observed to destabilize rhDNase. Similar effects were observed in Factor VIII. $Ca^{+2}$ and $Sr^{+2}$ ions stabilized the protein while others like $Mg^{+2}$, $Mn^{+2}$ and $Zn^{+2}$, $Cu^{+2}$ and $Fe^{+2}$ destabilized the enzyme (Fatouros, A., et al., Int. J. Pharm., 155, 121-131 (1997). In a separate study with Factor VIII, a significant increase in aggregation rate was observed in the presence of $Al^{+3}$ ions (Derrick T S, et al., /. Pharm. Sci., 93(10): 2549-57 (2004)). The authors note that other excipients like buffer salts are often contaminated with $Al^{+3}$ ions and illustrate the need to use excipients of appropriate quality in formulated products.

j. Other Common Excipient Components: Pharmaceutical Preservatives

Preservatives are necessary when developing multi-use parenteral formulations that involve more than one extraction from the same container. Their primary function is to inhibit microbial growth and ensure product sterility throughout the shelf-life or term of use of the drug product. Commonly used preservatives include, without limitation, benzyl alcohol, phenol and m-cresol. Although preservatives have a long history of use, the development of protein formulations that includes preservatives can be challenging. Preservatives almost always have a destabilizing effect (aggregation) on proteins, and this has become a major factor in limiting their use in multi-dose protein formulations (Roy S, et al., J Pharm ScL, 94(2): 382-96 (2005)).

To date, most protein drugs have been formulated for single-use only. However, when multi-dose formulations are possible, they have the added advantage of enabling patient convenience, and increased marketability. A good example is that of human growth hormone (hGH) where the development of preserved formulations has led to commercialization of more convenient, multi-use injection pen presentations. At least four such pen devices containing preserved formulations of hGH are currently available on the market. Norditropin® (liquid, Novo Nordisk), Nutropin AQ® (liquid, Genentech) & Genotropin (lyophilized—dual chamber cartridge, Pharmacia & Upjohn) contain phenol while Somatrope® (Eli Lilly) is formulated with m-cresol.

Several aspects need to be considered during the formulation development of preserved dosage forms. The effective preservative concentration in the drug product must be optimized. This requires testing a given preservative in the dosage form with concentration ranges that confer antimicrobial effectiveness without compromising protein stability. For example, three preservatives were successfully screened in the development of a liquid formulation for interleukin-1 receptor (Type I), using differential scanning calorimetry (DSC). The preservatives were rank ordered based on their impact on stability at concentrations commonly used in marketed products (Remmele R L Jr., et al., Pharm Res., 15(2): 200-8 (1998)).

Development of liquid formulations containing preservatives are more challenging than lyophilized formulations. Freeze-dried products can be lyophilized without the preservative and reconstituted with a preservative containing diluent at the time of use. This shortens the time for which a preservative is in contact with the protein significantly minimizing the associated stability risks. With liquid formulations, preservative effectiveness and stability have to be maintained over the entire product shelf-life (~18-24 months). An important point to note is that preservative effectiveness has to be demonstrated in the final formulation containing the active drug and all excipient components.

Some preservatives can cause injection site reactions, which is another factor that needs consideration when choosing a preservative. In clinical trials that focused on the evaluation of preservatives and buffers in Norditropin, pain perception was observed to be lower in formulations containing phenol and benzyl alcohol as compared to a formulation containing m-cresol (Kappelgaard A. M., Horm Res. 62 Suppl 3:98-103 (2004)). Interestingly, among the commonly used preservative, benzyl alcohol possesses anesthetic properties (Minogue S C, and Sun D A., AnesthAnalg., 100(3): 683-6 (2005)). In various aspects the use of preservatives provides a benefit that outweighs any side effects.

k. Methods of Preparation of Pharmaceutical Formulations

The present invention further contemplates methods for the preparation of pharmaceutical formulations.

The present methods further comprise one or more of the following steps: adding a stabilizing agent as described herein to said mixture prior to lyophilizing, adding at least one agent selected from a bulking agent, an osmolality regulating agent, and a surfactant, each of which as described herein, to said mixture prior to lyophilization.

The standard reconstitution practice for lyophilized material is to add back a volume of pure water or sterile water for injection (WFI) (typically equivalent to the volume removed during lyophilization), although dilute solutions of antibacterial agents are sometimes used in the production of pharmaceuticals for parenteral administration (Chen, Drug Development and Industrial Pharmacy, 18:1311-1354 (1992)). Accordingly, methods are provided for preparation of reconstituted rVWF compositions comprising the step of adding a diluent to a lyophilized rVWF composition of the invention.

The lyophilized material may be reconstituted as an aqueous solution. A variety of aqueous carriers, e.g., sterile water for injection, water with preservatives for multi dose use, or water with appropriate amounts of surfactants (for example, an aqueous suspension that contains the active compound in admixture with excipients suitable for the manufacture of aqueous suspensions). In various aspects, such excipients are suspending agents, for example and without limitation, sodium carboxymethylcellulose, methylcellulose, hydroxypropylmethylcellulose, sodium alginate, polyvinylpyrrolidone, gum tragacanth and gum acacia; dispersing or wetting agents are a naturally-occurring phosphatide, for example and without limitation, lecithin, or condensation products of an alkylene oxide with fatty acids, for example and without limitation, polyoxyethylene stearate, or condensation products of ethylene oxide with long chain aliphatic alcohols, for example and without limitation, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example and without limitation, polyethylene sorbitan monooleate. In various aspects, the aqueous suspensions also contain one or more preservatives, for example and without limitation, ethyl, or n-propyl, p-hydroxybenzoate.

l. Exemplary rVWF Formulation for Administration

In some embodiments, the present methods provide for an enhanced formulation that allows a final product with high potency (high rVWF concentration and enhanced long term stability) in order to reduce the volume for the treatment (100 IU/ml to 10000 IU/ml). In some embodiments, the rVWF concentration in the formulation for administration is about 100 IU/ml to 10000 IU/ml. In some embodiments, the rVWF concentration in the formulation for administration is about 500 IU/ml to 10000 IU/ml. In some embodiments, the rVWF concentration in the formulation for administration is about 1000 IU/ml to 10000 IU/ml. In some embodiments, the rVWF concentration in the formulation for administration is about 2000 IU/ml to 10000 IU/ml. In some embodiments, the rVWF concentration in the formulation for administration is about 3000 IU/ml to 10000 IU/ml. In some embodiments, the rVWF concentration in the formulation for administration is about 4000 IU/ml to 10000 IU/ml. In some embodiments, the rVWF concentration in the formulation for administration is about 5000 IU/ml to 10000 IU/ml. In some embodiments, the rVWF concentration in the formulation for administration is about 6000 IU/ml to 10000 IU/ml. In some embodiments, the rVWF concentration in the formulation for administration is about 7000 IU/ml to 10000 IU/ml. In some embodiments, the rVWF concentration in the formulation for administration is about 8000 IU/ml to 10000 IU/ml. In some embodiments, the rVWF concentration in the formulation for administration is about 9000 IU/ml to 10000 IU/ml.

In some embodiments, the formulation for administration comprises one or more zwitterionic compounds, including for example, amino acids like Histidine, Glycine, Arginine. In some embodiments, the formulation for administration comprises a component with amphipathic characteristic having a minimum of one hydrophobic and one hydrophilic group, including for example polysorbate 80, octylpyranosid, dipeptides, and/or amphipathic peptides. In some embodiments, the formulation for administration comprises a non reducing sugar or sugar alcohol or disaccharides, including for example, sorbitol, mannitol, sucrose, or trehalose. In some embodiments, the formulation for administration comprises a nontoxic water soluble salt, including for example, sodium chloride, that results in a physiological osmolality. In some embodiments, the formulation for administration comprises a pH in a range from 6.0 to 8.0. In some embodiments, the formulation for administration comprises a pH of about 6.0, about 6.5, about 7, about 7.5 or about 8.0. In some embodiments, the formulation for administration comprises one or more bivalent cations that stabilize rVWF, including for example, $Ca^{2+}$, $Mg^{2+}$, $Zn^{2+}$, $Mn^{2+}$ and/or combinations thereof. In some embodiments, the formulation for administration comprises about 1 mM to about 50 mM Glycine, about 1 mM to about 50 mM Histidine, about zero to about 300 mM sodium chloride (e.g., less than 300 mM sodium), about 0.01% to about 0.05% polysorbate 20 (or polysorbate 80), and about 0.5% to about 20% (w/w) sucrose with a pH of about 7.0 and having a physiological osmolarity at the time point of administration.

In some embodiments, the formulation for administration can be freeze dried. In some embodiments, the formulation for administration is stable and can be stored in liquid state at about 2° C. to about 8° C., as well as at about 18° C. to about 25° C. In some embodiments, the formulation for administration is stable and can be stored in liquid state at about 2° C. to about 8° C. In some embodiments, the formulation for administration is stable and can be stored in liquid state at about 18° C. to about 25° C.

V. Administration of rVWF for Methods of Prophylactic Treatment in Patients with Severe VWD In some embodiments, the present invention provides for prophylactically treating spontaneous bleeding episodes in a subject with severe von Willebrand Disease (VWD). In some embodiments, the prophylactic treatment comprises administering to the subject a recombinant von Willebrand Factor (rVWF) in order to reduce the frequency and/or duration of spontaneous bleeding episodes.

In some embodiments, spontaneous bleeding episodes include any episode not related to trauma. In some embodiments, the efficacy of the treatment is indicated by a reduction in the number of spontaneous bleeding episodes. In some embodiments, a reduction is the number of spontaneous bleeding episodes is indicated by a reduction in the annual bleeding rate (ABR). In some embodiments, the pretreatment ABR is determined based on the following formula: number of bleeds/days not on treatment regimen. In some embodiments, the pretreatment ABR is determined based on the following formula: number of bleeds/12 months prior to the prophylactic treatment with rVWF. In some embodiments, the prophylactic ABR (ABR after prophylactic treatment) is determined based on the following formula: number of bleeds/days on treatment regimen.

In some embodiments, a reduction of ≥25% in annual bleeding rate (ABR) for spontaneous bleeding episodes during rVWF prophylaxis relative to the pretreatment ABR is indicative of prophylactic treatment efficacy. In some embodiments, a reduction of ≥30% in annual bleeding rate (ABR) for spontaneous bleeding episodes during rVWF prophylactic treatment relative to the pretreatment ABR is indicative of prophylactic treatment efficacy. In some embodiments, a reduction of ≥35% in annual bleeding rate (ABR) for spontaneous bleeding episodes during rVWF prophylactic treatment relative to the pretreatment ABR is indicative of prophylactic treatment efficacy. In some embodiments, a reduction of ≥40% in annual bleeding rate (ABR) for spontaneous bleeding episodes during rVWF prophylactic treatment relative to the pretreatment ABR is indicative of prophylactic treatment efficacy. In some embodiments, a reduction of ≥45% in annual bleeding rate (ABR) for spontaneous bleeding episodes during rVWF prophylactic treatment relative to the pretreatment ABR is indicative of prophylactic treatment efficacy. In some embodiments, a reduction of ≥50% in annual bleeding rate (ABR) for spontaneous bleeding episodes during rVWF prophylactic treatment relative to the pretreatment ABR is indicative of prophylactic treatment efficacy. In some embodiments, a reduction of ≥55% in annual bleeding rate (ABR) for spontaneous bleeding episodes during rVWF prophylactic treatment relative to the pretreatment ABR is indicative of prophylactic treatment efficacy. In some embodiments, a reduction of ≥60% in annual bleeding rate (ABR) for spontaneous bleeding episodes during rVWF prophylactic treatment relative to the pretreatment ABR is indicative of prophylactic treatment efficacy. In some embodiments, a reduction of ≥65% in annual bleeding rate (ABR) for spontaneous bleeding episodes during rVWF prophylactic treatment relative to the pretreatment ABR is indicative of prophylactic treatment efficacy. In some embodiments, a reduction of ≥70% in annual bleeding rate (ABR) for spontaneous bleeding episodes during rVWF prophylactic treatment relative to the pretreatment ABR is indicative of prophylactic treatment efficacy. In some embodiments, a reduction of ≥75% in annual bleeding rate (ABR) for spontaneous bleeding episodes during rVWF prophylactic treatment relative to the pretreatment ABR is indicative of prophylactic treatment efficacy. In some embodiments, a reduction of ≥80% in annual bleeding rate (ABR) for spontaneous bleeding episodes during rVWF prophylactic treatment relative to the pretreatment ABR is indicative of prophylactic treatment efficacy. In some embodiments, a reduction of ≥85% in annual bleeding rate (ABR) for spontaneous bleeding episodes during rVWF prophylactic treatment relative to the pretreatment ABR is indicative of prophylactic treatment efficacy. In some embodiments, a reduction of ≥90% in annual bleeding rate (ABR) for spontaneous bleeding episodes during rVWF prophylactic treatment relative to the pretreatment ABR is indicative of prophylactic treatment efficacy.

In some embodiments, prophylactic treatment efficacy can be measured by obtaining samples and examining vWF:RCo and/or FVIII activities before and after prophylactic treatment with rVWF. In some embodiments, samples for examining FVIII, FVIII:C, VWF:RCo, VWF:Ag, and/or VWF collagen-binding capacity activities are obtained prior to the prophylactic treatment with rVWF and after the prophylactic treatment with rVWF. In some embodiments, samples for examining FVIII, FVIII:C, VWF:RCo, VWF:Ag, and VWF collagen-binding capacity activity are obtained 15 minutes, 30 minutes, 60 minutes, 3 hours, 6 hours, 12 hours, 24 hours, 28 hours, 32 hours, 48 hours, 72 hours, or 96 hours, after prophylactic treatment with rVWF. In some embodiments, samples for examining FVIII, FVIII:C, VWF:RCo, VWF:Ag, and VWF collagen-binding capacity activity are obtained 25 to 31 days after prophylactic treatment with rVWF. In some embodiments, samples for FVIII, FVIII:C, VWF:RCo, VWF:Ag, and VWF collagen-binding capacity activity are obtained after or during a bleeding episode and in such embodiments, a sample is take prior to rVWF administration, 2 hours after administration and then every 12-24 hours until resolution of the bleeding event. In some embodiments, treatment efficacy can be determined after or during a bleeding episode, and in such embodiments, samples for examining FVIII, FVIII:C, VWF:RCo, VWF:Ag, and/or VWF collagen-binding capacity activities are obtained after the bleeding episode, and further wherein the samples are obtained prior to rVWF administration, 2 hours after administration and then every 12-24 hours until resolution of the bleeding event. In some embodiments, FVIII, FVIII:C, VWF:RCo, VWF:Ag, and VWF collagen-binding capacity activity versus time profiles are determined based on the samples in order to monitor treatment efficacy for the prophylactic treatment with rVWF. In some embodiments, FVIII:C is also measured by a 1-stage clotting assay versus time profiles in order to monitor treatment efficacy for the prophylactic treatment with rVWF. In some embodiments, FVIII, FVIII:C, VWF:RCo, VWF:Ag, and/or VWF collagen-binding capacity activity levels are improved after the prophylactic treatment with rVWF as compared to the levels prior to the prophylactic treatment with rVWF. In some embodiments, FVIII, FVIII:C, VWF:RCo, VWF:Ag, and/or VWF collagen-binding capacity activity levels are improved after the prophylactic treatment with rVWF as compared to the levels prior to the prophylactic treatment with rVWF and this improvement is indicative of treatment efficacy. In some embodiments, prophylactic treatment efficacy is indicated by an improvement in FVIII, FVIII:C, VWF:RCo, VWF:Ag, and/or VWF collagen-binding capacity activity levels after the prophylactic treatment with rVWF as compared to the levels prior to the prophylactic treatment with rVWF. In some embodiments, an improvement in FVIII, FVIII:C, VWF:RCo, VWF:Ag, and/or VWF collagen-binding capacity activity levels includes a change in the activity levels such that the activity levels are closer to normal levels, e.g., levels in a subject that does not have VWD.

In some aspects, prophylactic treatment efficacy of rVWF administration is determined after or during a bleeding episode. In some embodiments, samples for examining FVIII, FVIII:C, VWF:RCo, VWF:Ag, and/or VWF collagen-binding capacity activities are obtained after the bleeding episode. In some embodiments, samples for examining FVIII, FVIII:C, VWF:RCo, VWF:Ag, and/or VWF collagen-binding capacity activities are obtained during the bleeding episode. In some instances, samples are obtained from a patient during a bleeding episode such that the FVIII, FVIII:C, VWF/RCo, VWF:Ag, and/or VWF collagen-binding capacity activities can be determined using the samples. In other instances, samples are obtained from a patient after a bleeding episode. In some embodiments the samples are obtained prior to rVWF administration. In some embodiments the samples are Obtained after rVWF administration. In some embodiments the samples are obtained 2 hours after rVWF administration. In some embodiments the samples are obtained every 12-24 hours until resolution of the bleeding episode. In certain embodiments, samples are obtained prior to rVWF administration and 2 hours after rVWF administration. In some embodiments, samples are obtained prior to rVWF administration and every 12-24 hours until resolution of the bleeding episode. In other embodiments, samples are obtained prior to rVWF administration, 2 hours after rVWF administration and every 12-24 hours until resolution of the bleeding episode. As such, the samples can be obtained prior to rVWF administration and prior to a bleeding episode. In some embodiments, samples are obtained after rVWF administration and prior to a bleeding episode. In some embodiments, samples are obtained after rVWF administration and during a bleeding episode. In certain embodiments, samples are obtained after rVWF administration and after resolution of a bleeding episode.

In some aspects, rVWF is administered to a subject at a range from 40-80 IU/kg, e.g., 40, 45, 50, 55, 60, 65, 70, 75, 80, 90, 100, 40-100, 40-80, 50-80, 60-80, 70-80, 40-50, 40-60, 40-70, 40-50, 50-60, 60-70, or 70-80 IU/kg. In some embodiments, rVWF is administered at least once a week to prevent a spontaneous bleeding episode. In some instances, the subject is given a single administration of rVWF. In some instances, the subject is administered a single infusion of rVWF.

In some aspects, rVWF is administered to a subject at a range from 40-80 IU/kg, e.g., 40, 45, 50, 55, 60, 65, 70, 75, 80, 90, 100, 40-100, 40-80, 50-80, 60-80, 70-80, 40-50, 40-60, 40-70, 40-50, 50-60, 60-70, or 70-80 IU/kg. In some embodiments, the dose ranges from 40 IU/kg to 60 IU/kg. In some embodiments, the dose ranges from 45 IU/kg to 55 IU/kg. In some embodiments, the dose is about 40 IU/kg, about 50 IU/kg, or about 60 IU/kg. In some embodiments, rVWF is administered at least two times each week to prevent a spontaneous bleeding episode. In other embodiments, rVWF is administered two or more times, e.g., 2, 3, 4, 5, or more times, a week to prevent a spontaneous bleeding episode. In some instances, the subject is given two administrations of rVWF. In some instances, the subject is administered two infusions of rVWF. In some embodiments, rVWF is administered twice a week. In some embodiments, rVWF is administered twice a week as an infusion dose ranging from 40 IU/kg to 60 IU/kg. In some embodiments, rVWF is administered twice a week as an infusion dose ranging from 40 IU/kg to 60 IU/kg by IV infusion. Each infusion can include a range from about 40-80 IU/kg rVWF, e.g., 40, 45, 50, 55, 60, 65, 70, 75, 80, 40-80, 50-80, 60-80, 70-80, 40-50, 40-60, 40-70, 40-50, 50-60, 60-70, or 70-80 IU/kg rVWF. In some embodiments, each infusion ranges from 40 IU/kg to 60 IU/kg. In some embodiments, each infusion ranges from 45 IU/kg to 55 IU/kg. In some embodiments, each infusion is about 40 IU/kg, about 50 IU/kg, or about 60 IU/kg. In some embodiments, the infusions can be substantially equal in amount. For instance, a first infusion and a second infusion can be substantially equal in amount. In some embodiments, the total dose of rVWF administered to the subject is about 40-160 IU/kg, e.g., 40-150, 40-125, 40-100, 40-90, 40-75, 50-150, 50-100, 75-150, 100-125, or 100-160 IU/kg.

In some aspects, rVWF is administered to a subject at a range from 40-80 IU/kg, e.g., 40, 45, 50, 55, 60, 65, 70, 75, 80, 90, 100, 40-100, 40-80, 50-80, 60-80, 70-80, 40-50, 40-60, 40-70, 40-50, 50-60, 60-70, or 70-80 IU/kg. In some embodiments, rVWF is administered at least two times each week to prevent a spontaneous bleeding episode. In some embodiments, rVWF is administered at least three times each week to prevent a spontaneous bleeding episode. In other embodiments, rVWF is administered three or more times, e.g., 3, 4, 5, or more times, a week to prevent a spontaneous bleeding episode. In some instances, the subject is given three administrations of rVWF. In some instances, the subject is administered three infusions of rVWF. Each infusion can include a range from about 40-80 IU/kg rVWF, e.g., 40, 45, 50, 55, 60, 65, 70, 75, 80, 40-80, 50-80, 60-80, 70-80, 40-50, 40-60, 40-70, 40-50, 50-60, 60-70, or 70-80 IU/kg rVWF. In some embodiments, the infusions can be substantially equal in amount. For instance, a first infusion, second infusion, and third infusion can be substantially equal in amount. In some embodiments, the total dose of rVWF administered to the subject is about 80-240 IU/kg, e.g., 120-240, 140-240, 140-200, 160-240, 180-240, 200-240, 80-120, 80-160, 80-200, 120-220, or 220-240 IU/kg. In some embodiments, the total dose of rVWF administered to the subject is less than about 160 IU/kg per week. In some embodiments, the total dose of rVWF administered to the subject is less than about 240 IU/kg per week.

In some embodiments, rVWF is administered at least once a week, at least twice (two times) a week, at least thrice (three times) a week, every day, every other day, every 2-3 days, every 2-4 days, every 2-5 days, and the like. In some instances, rVWF is administered for a total of 1 day, 2 days, 3 days, 4 days, 5 days, 6 days, or 7 days over the course of a 7-day period. In some embodiments, rVWF is administered on non-consecutive days. In some embodiments, rVWF is administered on consecutive days.

In some embodiments, rVWF is administered at least every 12 hours, 24 hours, 36 hour, 48 hours, 60 hours, 72 hours, 84 hours, or 96 hours. In some instances, rVWF is administered at least every 60 hours, 72 hours, or 84 hours. In some instances, rVWF is administered at least every 72 hours.

In some embodiments, recombinant Factor VIII (rFVIII) is also administered to the subject with severe VWD to prevent or reduce the frequency and/or duration of a spontaneous bleeding episode. In some cases, the treatment administered comprises rVWF and rFVIII. In other cases, the treatment administered does not include rFVIII. In some embodiments, rFVIII is administered to the subject at a range of about 10-70 IU/kg, e.g., 10-70, 10-60, 10-50, 10-40, 10-30, 10-20, 20-30, 30-40, 40-50, 50-60, or 60-70 IU/kg. In some instances, rFVIII is administered in the initial (first) dose or initial (first) infusion. In some instances, rFVIII is not administered in the initial (first) dose or initial (first) infusion. In some cases, rFVIII is administered as part of a second dose or second infusion. In some cases, rFVIII is not administered as part of a second dose or second infusion. In some cases, rFVIII is administered as part of a third dose or third infusion. In some cases, rFVIII is not administered as part of a third dose or third infusion.

In some embodiments, a subject with VWD who is at risk of having a spontaneous bleeding episode is administered a single infusion of rVWF and rFVIII. In some embodiments, the second administration of rVWF is not administered with FVIII. In some embodiments, the third administration of rVWF is not administered with FVIII.

In some embodiments, a subject with VWD who is at risk of having a spontaneous bleeding episode is administered a single infusion of rVWF and rFVIII. In some embodiments, the second administration of rVWF is administered with FVIII. In some embodiments, the third administration of rVWF is not administered with FVIII.

In some embodiments, a subject with VWD who is at risk of having a spontaneous bleeding episode is administered a single infusion of rVWF and rFVIII. In some embodiments, the second administration of rVWF is administered with FVIII. In some embodiments, the third administration of rVWF is administered with FVIII.

In some embodiments, a subject with VWD who is at risk of having a spontaneous bleeding episode is administered a single infusion of rVWF, and not rFVIII. In some embodiments, the second administration of rVWF is administered with FVIII. In some embodiments, the third administration of rVWF is administered with FVIII.

In some embodiments, a subject with VWD who is at risk of having a spontaneous bleeding episode is administered a single infusion of rVWF, and not rFVIII. In some embodiments, the second administration of rVWF is not administered with FVIII. In some embodiments, the third administration of rVWF is administered with FVIII.

In some embodiments, a subject with VWD who is at risk of having a spontaneous bleeding episode is administered a single infusion of rVWF, and not rFVIII. In some embodiments, the second administration of rVWF is administered with FVIII. In some embodiments, the third administration of rVWF is not administered with FVIII.

In some embodiments, a subject with VWD who is at risk of having a spontaneous bleeding episode is administered a first infusion and second infusion of rVWF. In some embodiments, the first and/or second infusion of rVWF is administered with FVIII.

In some embodiments, a subject with VWD who is at risk of having a spontaneous bleeding episode is administered a first infusion, second infusion, and third infusion of rVWF. In some embodiments, the first, second and/or third infusion of rVWF is administered with FVIII.

In some embodiments, of the method, when rVWF and FVIII are administered together, the rVWF to FVIII ratio is about 1.5:0.8. In some embodiments, of the method, when rVWF and FVIII are administered together, the rVWF to FVIII ratio is about 1.3:1. In some embodiments, of the method, when rVWF and FVIII are administered together, the rVWF to FVIII ratio is about 1.1:0.8. In some embodiments, of the method, when rVWF and FVIII are administered together, the rVWF to FVIII ratio is about 1.5:1. In some embodiments, of the method, when rVWF and FVIII are administered together, the rVWF to FVIII ratio is about 1.1:1.2.

In some embodiments, about 40 IU/kg rVWF of the rVWF is administered for prophylaxis of spontaneous bleeding. In some embodiments, about 45 IU/kg of the rVWF is administered for prophylaxis of spontaneous bleeding. In some embodiments, about 50 IU/kg of the rVWF is administered for prophylaxis of spontaneous bleeding. In some embodiments, about 55 IU/kg of the rVWF is administered for prophylaxis of spontaneous bleeding. In some embodiments, about 60 IU/kg of the rVWF is administered for prophylaxis of spontaneous bleeding. In some embodiments, about 65 IU/kg of the rVWF is administered for prophylaxis of spontaneous bleeding. In some embodiments, about 70 IU/kg of the rVWF is administered for prophylaxis of spontaneous bleeding. In some embodiments, about 75 IU/kg of the rVWF is administered for prophylaxis of spontaneous bleeding. In some embodiments, about 80 IU/kg of the rVWF is administered for prophylaxis of spontaneous bleeding. In some embodiments, about 40 IU/kg-80 IU/kg of the rVWF is administered for prophylaxis of spontaneous bleeding. In some embodiments, about 50 IU/kg-80 IU/kg of the rVWF is administered for prophylaxis of spontaneous bleeding. In some embodiments, about 40 IU/kg-70 IU/kg of the rVWF is administered for prophylaxis of spontaneous bleeding. In some embodiments, about 50 IU/kg-80 IU/kg of the rVWF is administered for prophylaxis of spontaneous bleeding. In some embodiments, about 40 IU/kg-60 IU/kg of the rVWF is administered for prophylaxis of spontaneous bleeding. In some embodiments, about 50 IU/kg-80 IU/kg of the rVWF is administered for prophylaxis of spontaneous bleeding.

In some embodiments, 40-80 IU/kg rVWF of the rVWF is administered twice per week for prophylactic treatment of spontaneous bleeding. In some embodiments, 50-80 IU/kg of the rVWF is administered twice per week for prophylactic treatment of spontaneous bleeding. In some embodiments, 40 IU/kg rVWF of the rVWF is administered twice per week for prophylactic treatment of spontaneous bleeding. In some embodiments, 45 IU/kg of the rVWF is administered twice per week for prophylactic treatment of spontaneous bleeding. In some embodiments, 50 IU/kg of the rVWF is administered twice per week for prophylactic treatment of spontaneous bleeding. In some embodiments, 55 IU/kg of the rVWF is administered twice per week for prophylactic treatment of spontaneous bleeding. In some embodiments, 60 IU/kg of the rVWF is administered twice per week for prophylactic treatment of spontaneous bleeding. In some embodiments, 65 IU/kg of the rVWF is administered twice per week for prophylactic treatment of spontaneous bleeding. In some embodiments, 70 IU/kg of the rVWF is administered twice per week for prophylactic treatment of spontaneous bleeding. In some embodiments, 75 IU/kg of the rVWF is administered twice per week for prophylactic treatment of spontaneous bleeding. In some embodiments, 80 IU/kg of the rVWF is administered twice per week for prophylactic treatment of spontaneous bleeding.

In some embodiments, 40-80 IU/kg rVWF of the rVWF is administered three times per week for prophylactic treatment of spontaneous bleeding. In some embodiments, 50-80 IU/kg of the rVWF is administered three times per week for prophylactic treatment of spontaneous bleeding. In some embodiments, 40 IU/kg rVWF of the rVWF is administered three times per week for prophylactic treatment of spontaneous bleeding. In some embodiments, 45 IU/kg of the rVWF is administered three times per week for prophylactic treatment of spontaneous bleeding. In some embodiments, 50 IU/kg of the rVWF is administered three times per week for prophylactic treatment of spontaneous bleeding. In some embodiments, 55 IU/kg of the rVWF is administered three times per week for prophylactic treatment of spontaneous bleeding. In some embodiments, 60 IU/kg of the rVWF is administered three times per week for prophylactic treatment of spontaneous bleeding. In some embodiments, 65 IU/kg of the rVWF is administered three times per week for prophylactic treatment of spontaneous bleeding. In some embodiments, 70 IU/kg of the rVWF is administered three times per week for prophylactic treatment of spontaneous bleeding. In some embodiments, 75 IU/kg of the rVWF is administered three times per week for prophylactic treatment of spontaneous bleeding. In some embodiments, 80 IU/kg of the rVWF is administered three times per week for prophylactic treatment of spontaneous bleeding. In some embodiments, 50 IU/kg of the rVWF is administered at least every 72 hours for prophylactic treatment of spontaneous bleeding.

In some embodiments, 40-80 IU/kg rVWF of the rVWF is administered once every 2 or 3 days for prophylactic treatment of spontaneous bleeding. In some embodiments, 50-80 IU/kg of the rVWF is administered once every 2 or 3 days for prophylactic treatment of spontaneous bleeding. In some embodiments, 40 IU/kg rVWF of the rVWF is administered once every 2 or 3 days for prophylactic treatment of spontaneous bleeding. In some embodiments, 45 IU/kg of the rVWF is administered once every 2 or 3 days for prophylactic treatment of spontaneous bleeding. In some embodiments, 50 IU/kg of the rVWF is administered once every 2 or 3 days for prophylactic treatment of spontaneous bleeding. In some embodiments, 55 IU/kg of the rVWF is administered once every 2 or 3 days for prophylactic treatment of spontaneous bleeding. In some embodiments, 60 IU/kg of the rVWF is administered once every 2 or 3 days for prophylactic treatment of spontaneous bleeding. In some embodiments, 65 IU/kg of the rVWF is administered once every 2 or 3 days for prophylactic treatment of spontaneous bleeding. In some embodiments, 70 IU/kg of the rVWF is administered once every 2 or 3 days for prophylactic treatment of spontaneous bleeding. In some embodiments, 75 IU/kg of the rVWF is administered once every 2 or 3 days for prophylactic treatment of spontaneous bleeding. In some embodiments, 80 IU/kg of the rVWF is administered once every 2 or 3 days for prophylactic treatment of spontaneous bleeding.

In some embodiments, 40-80 IU/kg of the rVWF is administered once every 3 or 4 days for prophylactic treatment of spontaneous bleeding. In some embodiments, 50-80 IU/kg of the rVWF is administered once every 3 or 4 days for prophylactic treatment of spontaneous bleeding. In some embodiments, 40 IU/kg of the rVWF is administered once every 3 or 4 days for prophylactic treatment of spontaneous bleeding. In some embodiments, 45 IU/kg of the rVWF is administered once every 3 or 4 days for prophylactic treatment of spontaneous bleeding. In some embodiments, 50 IU/kg of the rVWF is administered once every 3 or 4 days for prophylactic treatment of spontaneous bleeding. In some embodiments, 55 IU/kg of the rVWF is administered once every 3 or 4 days for prophylactic treatment of spontaneous bleeding. In some embodiments, 60 IU/kg of the rVWF is administered once every 3 or 4 days for prophylactic treatment of spontaneous bleeding. In some embodiments, 65 IU/kg of the rVWF is administered once every 3 or 4 days for prophylactic treatment of spontaneous bleeding. In some embodiments, 70 IU/kg of the rVWF is administered once every 3 or 4 days for prophylactic treatment of spontaneous bleeding. In some embodiments, 75 IU/kg of the rVWF is administered once every 3 or 4 days for prophylactic treatment of spontaneous bleeding. In some embodiments, 80 IU/kg of the rVWF is administered once every 3 or 4 days for prophylactic treatment of spontaneous bleeding.

In some embodiments, 40-80 IU/kg of the rVWF is administered once either on day 1 and day 5, on day 2 and day 6, or on day 3 and day 7 of a 7 day (week) period for prophylactic treatment of spontaneous bleeding. In some embodiments, 50-80 IU/kg of the rVWF is administered once either on day 1 and day 5, on day 2 and day 6, or on day 3 and day 7 of a 7 day (week) period for prophylactic treatment of spontaneous bleeding. In some embodiments, 40 IU/kg of the rVWF is administered once either on day 1 and day 5, on day 2 and day 6, or on day 3 and day 7 of a 7 day (week) period for prophylactic treatment of spontaneous bleeding. In some embodiments, 45 IU/kg of the rVWF is administered once either on day 1 and day 5, on day 2 and day 6, or on day 3 and day 7 of a 7 day (week) period for prophylactic treatment of spontaneous bleeding. In some embodiments, 50 IU/kg of the rVWF is administered once either on day 1 and day 5, on day 2 and day 6, or on day 3 and day 7 of a 7 day (week) period for prophylactic treatment of spontaneous bleeding. In some embodiments, 55 IU/kg rVWF of the rVWF is administered once either on day 1 and day 5, on day 2 and day 6, or on day 3 and day 7 of a 7 day (week) period for prophylactic treatment of spontaneous bleeding. In some embodiments, 60 IU/kg of the rVWF is administered once either on day 1 and day 5, on day 2 and day 6, or on day 3 and day 7 of a 7 day (week) period for prophylactic treatment of spontaneous bleeding. In some embodiments, 65 IU/kg of the rVWF is administered once either on day 1 and day 5, on day 2 and day 6, or on day 3 and day 7 of a 7 day (week) period for prophylactic treatment of spontaneous bleeding. In some embodiments, 70 IU/kg of the rVWF is administered once either on day 1 and day 5, on day 2 and day 6, or on day 3 and day 7 of a 7 day (week) period for prophylactic treatment of spontaneous bleeding. In some embodiments, 75 IU/kg of the rVWF is administered once either on day 1 and day 5, on day 2 and day 6, or on day 3 and day 7 of a 7 day (week) period for prophylactic treatment of spontaneous bleeding. In some embodiments, 80 IU/kg of the rVWF is administered once either on day 1 and day 5, on day 2 and day 6, or on day 3 and day 7 of a 7 day (week) period for prophylactic treatment of spontaneous bleeding.

In some embodiment, the subject receives prophylactic treatment of spontaneous bleeding for at least a month. In some embodiment, the subject receives prophylactic treatment of spontaneous bleeding for at least 6 months. In some embodiment, the subject receives prophylactic treatment of spontaneous bleeding for at least 1 year. In some embodiment, the subject receives prophylactic treatment of spontaneous bleeding for at least 2 years. In some embodiment, the subject receives prophylactic treatment of spontaneous bleeding for at least 5 years. In some embodiment, the subject receives prophylactic treatment of spontaneous bleeding for at least 10 years.

In some embodiments, a subject with severe VWD is administered a weekly dose of rVWF for prophylactic treatment of spontaneous bleeding episodes. In some embodiments, a weekly dose of rVWF that is substantially equivalent to a weekly dose of plasma-derived VWF (pdVWF) is administered to the subject for prophylaxis of spontaneous bleeding. In some embodiments, a weekly dose of rVWF that is functionally equivalent to a weekly dose of plasma-derived VWF (pdVWF) is administered to the subject for prophylaxis of spontaneous bleeding. In some embodiments, a weekly dose of rVWF that is about 10% less than a weekly dose of plasma-derived VWF (pdVWF) is administered to the subject for prophylaxis of spontaneous bleeding. In some embodiments, a weekly dose of rVWF that is about 10% more than a weekly dose of plasma-derived VWF (pdVWF) is administered to the subject for prophylaxis of spontaneous bleeding.

In some embodiments, a weekly dose of rVWF is administered as at least two separate doses or at least 2 infusions. In some embodiments, a subject is provided at least two doses per week. In some embodiments, a weekly dose of rVWF is administered as 2 infusions. In some embodiments, a weekly dose of rVWF is administered as 2 intravenous infusions. In some cases, the subject is administered a twice-weekly dose of rVWF or in other words, the subject is administered rVWF twice a week. In some embodiments, a weekly dose of rVWF is administered as 2 intravenous infusions. In some embodiments, rVWF is administered to the subject twice a week. In some embodiments, rVWF is administered to the subject every 3 or 4 days. In some embodiments, a first infusion of rVWF is administered and a second infusion of rVWF is administered 4 days later over a 7-day period. In some embodiments, rVWF is administered once on day 1 and day 5 of a 7-day period (a week) for prophylactic treatment of spontaneous bleeding. In some embodiments, a subject is administered a weekly dose that is divided into two infusions such that the subject receives a first infusion on day 1 and second infusion on day 5 of the week period. In some embodiments, rVWF is administered once on day 2 and day 6 of a week period for prophylactic treatment of spontaneous bleeding. In some embodiments, a subject is administered a weekly dose that is divided into two infusions such that the subject receives a first infusion on day 2 and second infusion on day 6 of the week period. In some embodiments, rVWF is administered once on day 3 and day 7 of a week period for prophylactic treatment of spontaneous bleeding. In some embodiments, a subject is administered a weekly dose that is divided into two infusions such that the subject receives a first infusion on day 3 and second infusion on day 7 of the week period. In some embodiments, a weekly dose of rVWF is up to 80 IU/kg of rVWF per each infusion. In some embodiments, a weekly dose of rVWF is divided into 2 intravenous infusions of up to 80 IU/kg of rVWF per each infusion.

In some embodiments, a weekly dose of rVWF is administered as at least 3 separate doses or at least 3 infusions. In some embodiments, a subject is provided at least 3 doses per week. In some embodiments, a weekly dose of rVWF is administered as 3 intravenous infusions. In some cases, the subject is administered a thrice-weekly dose of rVWF or in other words, the subject is administered rVWF three times a week. In some embodiments, rVWF is administered to the subject three times a week. In some embodiments, a weekly dose of rVWF is administered as 3 intravenous infusions such that each infusion is administered on a different day. In some embodiments, rVWF is administered to the subject every 2 or 3 days. In some embodiments, a first infusion of rVWF is administered, a second infusion of rVWF is administered 2 days later, and a third infusion of rVWF is administered 3 days later over a 7-day period. In some embodiments, rVWF is administered once on day 1, day 3, and day 6 of a 7-day period for prophylactic treatment of spontaneous bleeding. In some embodiments, a subject is administered a weekly dose that is divided into 3 infusions such that the subject receives a first infusion on day 1, second infusion on day 3, a third infusion on day 6 of the week period. In some embodiments, rVWF is administered once on day 1, day 3, and day 6 of a week period for prophylactic treatment of spontaneous bleeding. In some embodiments, a subject is administered a weekly dose that is divided into 3 infusions such that the subject receives a first infusion on day 2, second infusion on day 4, a third infusion on day 7 of the week period. In some embodiments, rVWF is administered once on day 2, day 4, and day 7 of a week period for prophylactic treatment of spontaneous bleeding. In some embodiments, a weekly dose of rVWF is up to 80 IU/kg of rVWF per each infusion. In some embodiments, a weekly dose of rVWF is divided into 3 intravenous infusions of up to 80 IU/kg of rVWF per each infusion.

In some embodiments, a weekly dose of rVWF is administered as a single dose or a single infusion. In some embodiments, a weekly dose of rVWF is administered as a single infusion. In some embodiments, a weekly dose of rVWF is administered as a single intravenous infusion. In some embodiments, a subject is administered a once-weekly dose of rVWF if the subject has previously received a once-weekly dose of pdVWF. In some embodiments, a weekly dose of rVWF is up to 80 IU/kg of rVWF for such an infusion.

In some embodiments, the subject experiences at least a 5% reduction (e.g., 5%, 7%, 10%, 12%, 14%, 15%, 17%, 20%, 22%, 24%, 25%, 27%, 30%, 32%, 34%, 35%, 37%, 40%, 42%, 44%, 45%, 47%, 50% or more reduction) in annual bleeding rate (ABR) for spontaneous bleeding events upon receiving the prophylactic treatment described herein. In some embodiments, the subject experiences at least a 25% reduction (e.g., 25%, 27%, 30%, 35%, 40%, 45%, 50%, 55%, 60%, 65%, 70%, 75%, 80%, 85%, 90% or more reduction) in ABR for spontaneous bleeding events upon receiving the prophylactic treatment. In some embodiments, a reduction is the number of spontaneous bleeding episodes is indicated by a reduction in the annual bleeding rate (ABR). In some embodiments, the pretreatment ABR is determined based on the following formula: number of bleeds/days not on treatment regimen. In some embodiments, the pretreatment ABR is determined based on the following formula: number of bleeds/12 months prior to the prophylactic treatment with rVWF. In some embodiments, the prophylactic ABR (ABR after prophylactic treatment) is determined based on the following formula: number of bleeds/days on treatment regimen.

In some embodiments, the subject experiences no spontaneous bleeding events during the course of prophylactic treatment with rVWF. In some embodiments, the subject experiences 1-2 spontaneous bleeding events during the course of prophylactic treatment with rVWF. In some embodiments, the subject experiences 1-3 spontaneous bleeding events during the course of prophylactic treatment with rVWF. In some embodiments, the subject experiences 3-5 spontaneous bleeding events during the course of prophylactic treatment with rVWF. In some embodiments, the subject experiences 1-5 spontaneous bleeding events during the course of prophylactic treatment with rVWF. In some embodiments, the subject experiences more than 5 spontaneous bleeding events during the course of prophylactic treatment with rVWF.

In some embodiments, administration of rVWF reduces the number of spontaneous bleeding events to 0 per year. In some embodiments, administration of rVWF reduces the number of spontaneous bleeding events to 1 per year. In some embodiments, administration of rVWF reduces the number of spontaneous bleeding events to 2 per year. In some embodiments, administration of rVWF reduces the number of spontaneous bleeding events to 3 per year. In some embodiments, administration of rVWF reduces the number of spontaneous bleeding events to 4 per year. In some embodiments, administration of rVWF reduces the number of spontaneous bleeding events to 5 per year. In some embodiments, administration of rVWF reduces the number of spontaneous bleeding events to more than 5 per year. In some embodiments, administration of rVWF reduces the number of spontaneous bleeding events to 1-5 per year. In some embodiments, administration of rVWF reduces the number of spontaneous bleeding events to 3-5 per year. In some embodiments, administration of rVWF reduces the number of spontaneous bleeding events to 1-3 per year. In some embodiments, administration of rVWF reduces the number of spontaneous bleeding events to less than 5 per year. In some embodiments, administration of rVWF reduces the number of spontaneous bleeding events to less than 4 per year. In some embodiments, administration of rVWF reduces the number of spontaneous bleeding events to less than 3 per year. In some embodiments, administration of rVWF reduces the number of spontaneous bleeding events to less than 2 per year. In some embodiments, administration of rVWF reduces the number of spontaneous bleeding events to less than 1 per year.

In some embodiments, prophylactic treatment reduces or diminishes the severity (e.g., mild, moderate, and severe bleeding episodes), incidence, frequency, or duration of a spontaneous bleeding episode. In some embodiments, the subject administered rVWF has fewer spontaneous bleeding episodes than a control subject that has not received prophylactic treatment. In some embodiments, the subject administered rVWF has fewer spontaneous bleeding episodes over the course of treatment compared to prior to initiating treatment.

Generally, Type 1 VWD is indicated by <30 IU/dL VWF:RCo, <30 IU/dL VWF:Ag, low or normal FVIII, and >0.5-0.7 IU/dL VWF:RCo/VWF:Ag Ratio. In some embodiments, a subject diagnosed with Type 1 VWD has <20 IU/dL VWF:RCo. Type 2A VWD is indicated by <30 IU/dL VWF:RCo, <30-200 IU/dL VWF:Ag, low or normal FVIII, and <0.5-0.7 IU/dL VWF:RCo/VWF:Ag Ratio. Type 2B VWD is indicated by <30-200 IU/dL VWF:RCo, <30 IU/dL VWF:Ag, low or normal FVIII, and usually <0.5-0.7 IU/dL VWF:RCo/VWF:Ag Ratio. Type 2M VWD is indicated by <30 IU/dL VWF:RCo, <30-200 IU/dL VWF:Ag, low or normal FVIII, and <0.5-0.7 IU/dL VWF:RCo/VWF:Ag Ratio. Type 2N VWD is indicated by 30-2000 IU/dL VWF:RCo, 30-200 IU/dL VWF:Ag, very low FVIII, and >0.5-0.7 IU/dL VWF:RCo/VWF:Ag Ratio. Type 3 VWD is indicated by <3 IU/dL VWF:RCo, <3 IU/dL VWF:Ag, extremely low (<10 IU/dL) FVIII, and the VWF:RCo/VWF:Ag Ratio is not applicable. In some embodiments, a subject diagnosed with Type 3 VWD has <3 IU/dL VWF:Ag. Normal is indicated by 50-200 IU/dL VWF:RCo, 50-200 IU/dL VWF:Ag, normal FVIII, and >0.5-0.7 IU/dL VWF:RCo/VWF:Ag Ratio. In some embodiments, the subject has Type 3 VWD. In some embodiments, the subject has severe type 1 VWD. In some embodiments, the subject has severe type 2 VWD. In some embodiments, the subject has severe type 2A VWD. In some embodiments, the subject has severe type 2B VWD. In some embodiments, the subject has severe type 2M VWD. In some embodiments, the subject has severe type 3 VWD.

In some embodiments, prophylactic treatment efficacy is indicated by an improvement in FVIII, VWF:RCo, and/or VWF:Ag activity levels after the prophylactic treatment with rVWF as compared to the levels prior to the prophylactic treatment with rVWF in patients with Type 1 VWD. In some embodiments, an improvement in FVIII, VWF:RCo, and/or VWF:Ag activity levels includes a change in the activity levels such that the activity levels are closer to normal levels, e.g., levels in a subject that does not have Type 1 VWD. In some embodiments, prophylactic treatment efficacy is indicated by an improvement in FVIII, VWF:RCo, and/or VWF:Ag activity levels after the prophylactic treatment with rVWF as compared to the levels prior to the prophylactic treatment with rVWF in patients with severe Type 1 VWD. In some embodiments, an improvement in FVIII, VWF:RCo, and/or VWF:Ag activity levels includes a change in the activity levels such that the activity levels are closer to normal levels; e.g., levels in a subject that does not have severe Type 1 VWD. In some embodiments, prophylactic treatment efficacy is indicated by an improvement in FVIII, VWF:RCo, and/or VWF:Ag activity levels after the prophylactic treatment with rVWF as compared to the levels prior to the prophylactic treatment with rVWF in patients with Type 2A VWD. In some embodiments, an improvement in FVIII, VWF:RCo, and/or VWF:Ag activity levels includes a change in the activity levels such that, the activity levels are closer to normal levels, e.g., levels in a subject, that does not have Type 2A VWD. In some embodiments, prophylactic treatment efficacy is indicated by an improvement in FVIII, VWF:RCo, and/or VWF:Ag activity levels after the prophylactic treatment with rVWF as compared to the levels prior to the prophylactic treatment with rVWF in patients with severe Type 2A VWD. In some embodiments, an improvement in FVIII, VWF:RCo, and/or VWF:Ag activity levels includes a change in the activity levels such that the activity levels are closer to normal levels, e.g., levels in a subject that does not have severe Type 2A VWD. In some embodiments, prophylactic treatment efficacy is indicated by an improvement in FVIII, VWF:RCo, and/or VWF:Ag activity levels after the prophylactic treatment with rVWF as compared to the levels prior to the prophylactic treatment with rVWF in patients with Type 2M VWD. In some embodiments, an improvement in FVIII, VWF:RCo, and/or VWF:Ag activity levels includes a change in the activity levels such that the activity levels are closer to normal levels, e.g., levels in a subject that does not have Type 2M VWD. In some embodiments, prophylactic treatment efficacy is indicated by an improvement in FVIII, VWF:RCo, and/or VWF:Ag activity levels after the prophylactic treatment with rVWF as compared to the levels prior to the prophylactic treatment with rVWF in patients with severe Type 2M VWD. In some embodiments, an improvement in FVIII, VWF:RCo, and/or VWF:Ag activity levels includes a Change in the activity levels such that the activity levels are closer to normal levels, e.g., levels in a subject that does not have severe Type 2M VWD. In some embodiments, prophylactic treatment efficacy is indicated by an improvement in FVIII, VWF:RCo, and/or VWF:Ag activity levels after the prophylactic treatment with rVWF as compared to the levels prior to the prophylactic treatment with rVWF in patients with Type 2N VWD. In some embodiments, an improvement in FVIII, VWF:RCo, and/or VWF:Ag activity levels includes a change in the activity levels such that the activity levels are closer to normal levels, e.g., levels in a subject that does not have Type 2N VWD. In some embodiments, prophylactic treatment efficacy is indicated by an improvement in FVIII, VWF:RCo, and/or VWF:Ag activity levels after the prophylactic treatment with rVWF as compared to the levels prior to the prophylactic treatment with rVWF in patients with severe Type 2N VWD. In some embodiments, an improvement in FVIII, VWF:RCo, and/or VWF:Ag activity levels includes a change in the activity levels such that the activity levels are closer to normal levels, e.g., levels in a subject that does not have severe Type 2N VWD. In some embodiments, prophylactic treatment efficacy is indicated by an improvement in FVIII, VWF:RCo, and/or VWF:Ag activity levels after the prophylactic treatment with rVWF as compared to the levels prior to the prophylactic treatment with rVWF in patients with Type 3 VWD. In some embodiments, an improvement in FVIII, VWF:RCo, and/or VWF:Ag activity levels includes a change in the activity levels such that the activity levels are closer to normal levels, e.g., levels in a subject that does not have Type 3 VWD. In some embodiments, prophylactic treatment efficacy is indicated by an improvement in FVIII, VWF:RCo, and/or VWF:Ag activity levels after the prophylactic treatment with rVWF as compared to the levels prior to the prophylactic treatment with rVWF in patients with severe Type 3 VWD. In some embodiments, an improvement in FVIII, VWF:RCo, and/or VWF:Ag activity levels includes a change in the activity levels such that the activity levels are closer to normal levels, e.g., levels in a subject that does not have severe Type 3 VWD. In some embodiments, an improvement in FVIII, VWF:RCo, and/or VWF:Ag activity levels includes a change in the activity levels such that the activity levels are closer to normal levels, e.g., levels in a subject that does not have any form of VWD, In some embodiments, the subject has received a diagnosis of VWD. In some instance, the VWD diagnosis is confirmed by genetic testing, multimer analysis, patient history, or a combination thereof.

In some embodiments, the subject had been treated for at least 1 spontaneous bleeding event within the previous 12 months. In some embodiments, the subject had been treated for more than 1 spontaneous bleeding event within the previous 12 months. In some embodiments, the subject had been treated for at least 3 spontaneous bleeding event within the previous 12 months. In some embodiments, the subject had been treated for 3 or more spontaneous bleeding events within the previous 12 months.

In some embodiments, the subject is currently receiving on-demand treatment for a spontaneous bleeding event (e.g., episode). In some embodiments, the subject is currently receiving VWF therapy (e.g., rVWF or pdVWF therapy) to treat a spontaneous bleeding event. In some embodiments, the subject is not currently receiving on-demand treatment for a spontaneous bleeding event (e.g., episode). In some embodiments, the subject is not currently receiving VWF therapy (e.g., rVWF or pdVWF therapy) to treat a spontaneous bleeding event.

In some embodiments, the subject has been prophylactically treated for spontaneous bleeding by administration of pdVWF within the previous 12 months. In some embodiments, the subject has been prophylactically treated for spontaneous bleeding by administration of pdVWF for the previous 12 months. In some embodiments, the subject has been prophylactically treated for spontaneous bleeding by administration of pdVWF for at least the previous 12 months. In some embodiments, the subject has not been prophylactically treated for spontaneous bleeding by administration of pdVWF within the previous 12 months. In some embodiments, the subject has not been prophylactically treated for spontaneous bleeding by administration of pdVWF for the previous 12 months. In some embodiments, the subject has not been prophylactically treated for spontaneous bleeding by administration of pdVWF for at least the previous 12 months.

Generally, minor bleeding is characterized by acute or subacute clinically overt bleeding that did not satisfy the criteria for major bleeding and led to hospital admission for bleeding, physician-guided medical or surgical treatment for bleeding, or a change in antithrombotic therapy (including study drugs) for bleeding (Aristotle clinical definition); All other bleeding (except major and ICH) (RE-LY clinical definition); Overt bleeding not meeting the criteria for major bleeding but requiring medical intervention, unscheduled contact (visit or telephone) with a physician, temporary interruption of study drug (i.e., delayed dosing), pain, or impairment of daily activities) Rocket-AF clinical definition); Clinically relevant bleeding was defined as skin hematoma>25 cm$^2$, spontaneous nosebleed of >5 minutes duration, macroscopic hematuria, spontaneous rectal bleeding, gingival bleeding for >5 minutes, any bleeding leading to hospitalization, any bleeding leading to transfusion<2 U, or any other bleeding considered relevant by the investigator (Petro clinical definition); and/or CRNM (clinically relevant non-major bleeding) defined as acute or subacute, clinically overt, not major, and leading to hospital admission for bleeding, physician-guided medical or surgical treatment for bleeding, or a change in antithrombotic therapy as well as minor bleeding events defined as acute clinically overt events not meeting the criteria for either major or CRNM bleeding (Aristotle-J clinical definition). See, for example, Wells G, Coyle D, Cameron C, et al. Safety, Effectiveness, and Cost-Effectiveness of New Oral Anticoagulants Compared with Warfarin in Preventing Stroke and Other Cardiovascular Events in Patients with Atrial Fibrillation [Internet]. Ottawa (ON): Canadian Agency for Drugs and Technologies in Health; 2012 Apr. 9. 3, CLINICAL REVIEW. Available on the World Wide Web at www.ncbi.nlm.nih.gov/books/NBK169813/. Minor bleeding can include events were defined as those not fulfilling the criteria of major or clinically significant bleeding; minor bleeding from a wound (bleeding at the injection site, epistaxis, or wound hematoma not requiring operative decompression); overt bleeding that did not meet the criteria for major hemorrhage and associated with ≥1 of the following: epistaxis lasting more than 5 minutes or requiring intervention, ecchymosis or hematoma>5 cm at its greatest dimension, hematuria not associated with urinary catheter related trauma, GI hemorrhage not related to intubation or placement of a NG tube, wound hematoma or complications, subconjunctival hemorrhage necessitating cessation of medication; minor bleeding in the GI or urinary tract and hematoma at the site of an injection; and/or overt bleeding not meeting the criteria for major hemorrhage. See, for example, Sobieraj D M, Coleman C I, Tongbram V, et al. Venous Thromboembolism Prophylaxis in Orthopedic Surgery [Internet]. Rockville (Md.): Agency for Healthcare Research and Quality (US); 2012 March (Comparative Effectiveness Reviews, No. 49.) Appendix F, Additional Evidence Tables. Available from the World Wide Web at www.ncbi.nlm.nih.gov/books/NBK92309/.

Generally major bleeding is characterized by International Society on Thrombosis and Haemostasis (ISTH) standards, and includes, any life threatening and/or fatal bleeding; symptomatic bleeding into a critical area or organ and major bleeding was separated into intracranial (intracerebral, subdural) and extracranial (GI, non-GI) bleeding (RE-LY clinical definition); symptomatic bleeding into a critical anatomic site (Rocket-AF clinical definition); Life-threatening retroperitoneal, intracranial, intraocular, or intraspinal bleeding; or bleeding requiring surgery (Artistotle-J clinical definition). Major bleeding events can include those where there is fall in hemoglobin at least 20 g/L or transfusion of >2 units of whole blood (packed cells mentioned in life-threatening bleed definition; RE-LY definition of life-threatening bleeding: >1 of the following criteria: (1) fatal, symptomatic intracranial bleed; (2) reduction in hemoglobin level of at least 5.0 g/L; (3) transfusion of at least 4 U of blood or packed cells; (4) associated with hypotension requiring the use of intravenous inotropic agents; or (5)

necessitated surgical intervention); fall in hemoglobin>2 g/dL or transfusion of >2 units of whole blood/red cells (ISTH or Rocket-AF clinical definition); and/or bleeding requiring surgery or transfusion of ≥2 U or associated with a decrease in hemoglobin of ≥2.0 g/L episodes. See, for example, Wells G, Coyle D, Cameron C, et al. Safety, Effectiveness, and Cost-Effectiveness of New Oral Anticoagulants Compared with Warfarin in Preventing Stroke and Other Cardiovascular Events in Patients with Atrial Fibrillation [Internet]. Ottawa (ON): Canadian Agency for Drugs and Technologies in Health; 2012 Apr. 9. 3, CLINICAL REVIEW. Available on the World Wide Web at www.ncbi.nlm.nih.gov/books/NBK169813/. Major bleeding can include clinically overt bleeding associated with >20 g/L fall in Hb; clinically overt leading to transfusion of >2 U packed cells or whole blood; fatal, retroperitoneal, intracranial, intraocular or intraspinal bleeding; bleeding warranting treatment cessation or leading to reoperation; fatal, retroperitoneal, intracranial, or intraspinal bleeding; bleeding that involved any other critical organ; bleeding leading to reoperation; overt bleeding with a bleeding index≥2; major bleeding from a wound (wound hematoma requiring operative decompression), or major bleeding not related to a wound (gastrointestinal or intracerebral hemorrhage); clinically overt bleeding associated with either a decrease in Hb≥2 g/dL or a need for a transfusion of ≥2 U RBC; intracranial or retroperitoneal (resulted in the permanent discontinuation of anticoagulation). See, for example, Sobieraj D M, Coleman C I, Tongbram V, et al. Venous Thromboembolism Prophylaxis in Orthopedic Surgery [Internet]. Rockville (Md.): Agency for Healthcare Research and Quality (US); 2012 March (Comparative Effectiveness Reviews, No. 49.) Appendix F, Additional Evidence Tables. Available from: the World Wide Web at www.ncbi.nlm.nih.gov/books/NBK92309/.

Compositions of rVWF can be contained in pharmaceutical formulations, as described herein. Such formulations can be administered orally, topically, transdermally, parenterally, by inhalation spray, vaginally, rectally, or by intracranial injection. The term parenteral as used herein includes subcutaneous injections, intravenous, intramuscular, intraisternal injection, or infusion techniques. In some embodiments, the rVWF is administered intravenously. Administration by intravenous, intradermal, intramuscular, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient.

In one aspect, formulations of the invention are administered by an initial bolus followed by a continuous infusion to maintain therapeutic circulating levels of drug product. As another example, the inventive compound is administered as a one-time dose. Those of ordinary skill in the art will readily optimize effective dosages and administration regimens as determined by good medical practice and the clinical condition of the individual patient. The route of administration can be, but is not limited to, by intravenous, intraperitoneal, subcutaneous, or intramuscular administration. The frequency of dosing depends on the pharmacokinetic parameters of the agents and the route of administration. The optimal pharmaceutical formulation is determined by one skilled in the art depending upon the route of administration and desired dosage. See for example, Remington's Pharmaceutical Sciences, 18th Ed., 1990, Mack Publishing Co., Easton, Pa. 18042 pages 1435-1712, the disclosure of which is hereby incorporated by reference in its entirety for all purposes and in particular for all teachings related to formulations, routes of administration and dosages for pharmaceutical products. Such formulations influence the physical state, stability, rate of in vivo release, and rate of in vivo clearance of the administered agents. Depending on the route of administration, a suitable dose is calculated according to body weight, body surface area or organ size. Appropriate dosages may be ascertained through use of established assays for determining blood level dosages in conjunction with appropriate dose-response data. The final dosage regimen is determined by the attending physician, considering various factors which modify the action of drugs, e.g. the drug's specific activity, the severity of the damage and the responsiveness of the patient, the age, condition, body weight, sex and diet of the patient, the severity of any infection, time of administration and other clinical factors. By way of example, a typical dose of a recombinant VWF of the present invention is approximately 50 IU/kg, equal to 500 µg/kg. As studies are conducted, further information will emerge regarding the appropriate dosage levels and duration of treatment for various diseases and conditions.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, Highly stabilized York, Gait, "Oligonucleotide Synthesis: A Practical Approach" 1984, IRL Press, London, Nelson and Cox (2000), Lehninger, Principles of Biochemistry 3rd Ed., W. H. Freeman Pub., Highly stabilized York, N.Y. and Berg et al. (2002) Biochemistry, 5th Ed., W. H. Freeman Pub., Highly stabilized York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "an antibody" includes a plurality of such antibodies and reference to "a host cell" includes reference to one or more host cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the above description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Although the present invention is described primarily with reference to specific embodiments, it is also envisioned that other embodiments will become apparent to those skilled in the art upon reading the present disclosure, and it is intended that such embodiments be contained within the present inventive method.

EXAMPLES

Example 1: Efficacy and Safety of Prophylaxis with Recombinant Von Willebrand Factor (VWF) in Severe Von Willebrand Disease (VWD): Design of a Prospective, Phase 3, Open-Label, International Multicenter Study Introduction Patients with von Willebrand disease (VWD) have impaired hemostasis owing to a quantitative or qualitative deficit in von Willebrand Factor (VWF), a large multimeric plasma glycoprotein with key hemostatic functions mediating platelet aggregation and stabilizing blood clotting factor VIII (FVIII) in circulation (1-3). Most patients with VWD present with mild to moderate mucosal bleeding and bleeding after trauma or surgery, although life-threatening bleeding may also occur, particularly in patients with severe disease (1,2).

Recombinant VWF (rVWF, vonicog alfa, VEYVONDI™; Baxalta Innovations GmbH, a Takeda company, Vienna, Austria) is manufactured by recombinant DNA technology in the Chinese hamster ovary cell line without the addition of exogenous human or animal-derived protein (4). VWF contains the full VWF multimer profile, including ultra-large multimers that are usually deficient in plasma-derived VWF (pdVWF) concentrates exposed to ADAMTS13, the VWF-cleaving protease (5-7)

Patients with severe VWD may benefit from prophylactic rVWF treatment to maintain VWF and FVIII levels so that the risk of spontaneous bleeding episodes (BEs), including hemarthrosis, epistaxis, and gastrointestinal bleeding, is reduced (8-13).

Reducing the frequency and duration of BEs likely decreased the need for red blood cell transfusions and lower the risk of debilitating comorbidities, including arthropathy (8,9)

Study Objectives

The objective of the study was to investigate the efficacy and safety of long-term prophylactic treatment with rVWF in patients with severe VWD.

Study Design

Described herein is a global, multicenter, open-label, phase 3 study (NCT02973087, EudraCT no.: 2016-001478-14) to prospectively evaluate the efficacy, safety, and pharmacokinetics of continuous prophylactic treatment with rVWF in adult patients with severe VWD (baseline VWF ristocetin cofactor activity [VWF:RCo]<20 IU/dL) who have required therapy with pdVWF to control BEs in the year prior to enrollment (FIG. 1).

Patients belong to 1 or 2 cohorts, depending on the type of VWF regimen received prior to enrollment in the study: on-demand treatment (on-demand cohort) and prophylactic treatment with a pdVWF product (switch cohort). Patients in both cohorts to receive prophylactic rVWF treatment for 1 year.

Patients

Patients≥18 years of age diagnosed with severe VWD (baseline VWF:RCo<20 IU/dL) requiring VWF treatment to control bleeding (key study eligibility criteria are detailed in FIG. 2) The study protocol was approved by the relevant local ethics committee and all patients will have provided written informed consent before enrollment.

Study Treatment

Patients received rVWF prophylaxis as described below.

For the on-demand cohort, a standard prophylactic dose of 50±10 IU/kg rVWF:RCo was administered by intravenous infusion. The dose could be increased up to 80 IU/kg. All patients were initiated on twice-weekly dosing (FIG. 3, Schedule A).

For the switch cohort, a weekly rVWF dose equivalent to ±10% of the weekly pdVWF dose received previously, was divided into 2 intravenous infusions (FIG. 3, Schedule A), to a maximum of 80 IU/kg per infusion. The weekly dose was given as 3 infusions (FIG. 3, Schedule B), according to clinical judgment; once-weekly dosing was only permitted if the patient had received prior once-weekly dosing with pdVWF.

The rVWF dose could be further individualized with the specified range on the basis of pharmacokinetic data, history of BEs, and the results from clinical and laboratory assessments. Patients experiencing BEs requiring VWF treatment would have received rVWF to treat the bleed. Weight-adjusted dosing should be based on the type and severity of the BE and appropriate clinical and laboratory measures. Recombinant FVIII (antihemophilic factor [recombinant] [ADVATE; Baxalta US Inc., a Takeda company, Lexington, MA]) would have been administered if an immediate increase of the FVIII level is clinically indicated.

Patients requiring elective surgery or dental procedures during the study were treated with rVWF to manage surgical bleeding and then resumed their prophylactic rVWF treatment schedule. Before surgery, rVWF was administered without recombinant FVIII if FVIII activity (FVIII:C) levels are at the recommended target level of: ≥0.4 IU/mL for minor or oral surgery, and ≥0.8 IU/mL for major surgery.

Study Outcome Measures and Statistical Analysis

The main study outcome measures are listed in FIG. 4 (Table 3).

Statistical analysis included approximately 22 patients, including at least 5 patients with type 3 VWD and at least 8 patients in each study cohort; no formal sample size calculations were done.

The primary efficacy analysis was conducted on all patients who have received prophylactic rVWF treatment. Spontaneous ABRs will be estimated using a negative binominal regression for each study cohort (on-demand cohort or switch cohort). The comparison of prestudy and on-study spontaneous ABRs was based on the patients in the switch cohort. Assessment will use a generalized linear mixed-effects model. ABR ratio was reported with a 2-sided 95% confidence interval for each study cohort.

Study Status and Conclusion

Study enrollment is now completed.

Results from this prospective phase 3 study have provided data on the efficacy and safety of rVWF for prophylaxis against spontaneous bleeds in patients with severe VWD.

The study period of prophylactic rVWF treatment was 1 year, and the primary efficacy outcome measure is the ABR for spontaneous (nontraumatic) bleeds.

Primary Outcome Measures

Prospectively recorded annualized bleeding rate (ABR) for spontaneous (not related to trauma) bleeding episodes during prophylactic treatment with (rVWF) and the participants' historical ABR for spontaneous bleeding episodes during on-demand treatment (Time Frame: Approximately 1 year).

Revised Secondary Outcome Measures

Number of participants with reduction of annualized bleeding rate (ABR) for spontaneous (not related to trauma) bleeding episodes during prophylaxis relative to the participants' own historical ABR during on-demand treatment (Time Frame: Approximately 1 year).

Number of participants with zero bleeds during prophylactic treatment with recombinant von Willebrand factor (rVWF) (Time Frame: Approximately 1 year).

Number of infusions of recombinant von Willebrand factor (rVWF) and ADVATE per month during prophylactic treatment as well as during on-demand treatment (Time Frame: Approximately 1 year).

Number of infusions of recombinant von Willebrand factor (rVWF) and ADVATE per year during prophylactic treatment as well as during on-demand treatment (Time Frame: Approximately 1 year).

Total weight adjusted consumption of recombinant von Willebrand factor (rVWF) and ADVATE per month during prophylactic treatment as well as during on-demand treatment (Time Frame: Approximately 1 year).

Total weight adjusted consumption of recombinant von Willebrand factor (rVWF) and ADVATE per year during prophylactic treatment as well as during on-demand treatment (Time Frame: Approximately 1 year).

Incidence of thromboembolic events (Time Frame: Throughout the study period of approximately 22 months).

Incidence of severe hypersensitivity reactions (Time Frame: Throughout the study period of approximately 22 months).

Number of participants who develop neutralizing antibodies to recombinant von Willebrand factor (rVWF) and Factor VIII (FVIII) (Time Frame: Throughout the study period of approximately 22 months).

Number of participants who develop total binding antibodies to recombinant von Willebrand factor (rVWF) and Factor VIII (FVIII) (Time Frame: Throughout the study period of approximately 22 months).

Number of participants who develop antibodies to Chinese hamster ovary (CHO) proteins, mouse immunoglobulin G (IgG) and rFurin (Time Frame: Throughout the study period of approximately 22 months).

Pharmacokinetics—Incremental recovery (IR) (Time Frame: 30 minutes pre-infusion; and post-infusion at 30 minutes and 1, 6, 12, 24, 48, and 72 hours).

Pharmacokinetics—Terminal half-life (T½) (Time Frame: 30 minutes pre-infusion; and post-infusion at 30 minutes and 1, 6, 12, 24, 48, and 72 hours).

Pharmacokinetics—Mean residence time (MRT) (Time Frame: 30 minutes pre-infusion; and post-infusion at 30 minutes and 1, 6, 12, 24, 48, and 72 hours).

Pharmacokinetics—Area under the curve/dose (AUC/dose) (Time Frame: 30 minutes pre-infusion; and post-infusion at 30 minutes and 1, 6, 12, 24, 48, and 72 hours).

Pharmacokinetics—Area under moment curve/dose (AUMC/dose) (Time Frame: 30 minutes pre-infusion; and post-infusion at 30 minutes and 1, 6, 12, 24, 48, and 72 hours).

Pharmacokinetics—Volume of distribution at steady state (Vss) (Time Frame: 30 minutes pre-infusion; and post-infusion at 30 minutes and 1, 6, 12, 24, 48, and 72 hours).

Pharmacokinetics—Clearance (CL) (Time Frame: 30 minutes pre-infusion; and post-infusion at 30 minutes and 1, 6, 12, 24, 48, and 72 hours).

Number of infusions of recombinant von Willebrand factor (rVWF) and ADVATE (rFVIII) per spontaneous bleeding episode (BE) (Time Frame: Throughout the study period, up to approximately 22 months).

Number of infusions of recombinant von Willebrand factor (rVWF) and ADVATE (rFVIII) per traumatic bleeding episode (BE) (Time Frame: Throughout the study period, up to approximately 22 months).

Weight-adjusted consumption of recombinant von Willebrand factor (rVWF) and ADVATE (rFVIII) per spontaneous bleeding episode (BE) (Time Frame: Throughout the study period, up to approximately 22 months).

Weight-adjusted consumption of recombinant von Willebrand factor (rVWF) and ADVATE (rFVIII) per traumatic bleeding episode (BE) (Time Frame: Throughout the study period, up to approximately 22 months).

Overall hemostatic efficacy rating at resolution of bleed (Time Frame: Throughout the study period, up to approximately 22 months). Used a 4-point scale: Excellent, Good, Moderate, None.

Intraoperative actual versus predicted blood loss—if surgery is required (Time Frame: Day 0 (at completion of surgery)). Assessed by the operating surgeon) at completion of surgery.

Intraoperative hemostatic efficacy—if surgery is required (Time Frame: Day 0 (at completion of surgery)). Score on a scale of excellent, good, moderate or none—assessed by the operating surgeon at completion of surgery.

For elective surgery: an overall assessment of hemostatic efficacy 24 hours and on Day 7 and Day 14 after the last perioperative infusion of rVWF (Time Frame: 24 hours and on Day 7 and Day 14 after the last perioperative infusion of rVWF). Score on a scale of excellent, good, moderate or none.

Daily intra- and postoperative weight-adjusted dose (Time Frame: Day 0 (surgery day) through postoperative day 14). Daily intra- and postoperative weight-adjusted dose of rVWF with or without ADVATE.

Original Secondary Outcome Measures

Number of participants with reduction of annualized bleeding rate (ABR) for spontaneous (not related to trauma) bleeding episodes during prophylaxis relative to the participants' own historical ABR during on-demand treatment (Time Frame: Approximately 1 year).

Number of participants with zero bleeds during prophylactic treatment with recombinant von Willebrand factor (rVWF) (Time Frame: Approximately 1 year).

Number of infusions of recombinant von Willebrand factor (rVWF) and ADVATE per month during on-demand treatment (Time Frame: Approximately 1 year).

Number of infusions of recombinant von Willebrand factor (rVWF) and ADVATE per year during on-demand treatment (Time Frame: Approximately 1 year).

Total weight adjusted consumption of recombinant von Willebrand factor (rVWF) and ADVATE per month on-demand treatment (Time Frame: Approximately 1 year).

Total weight adjusted consumption of recombinant von Willebrand factor (rVWF) and ADVATE per year on-demand treatment (Time Frame: Approximately 1 year).

Incidence of thromboembolic events (Time Frame: Throughout the study period of approximately 22 months).

Incidence of severe hypersensitivity reactions (Time Frame: Throughout the study period of approximately 22 months).

Number of participants who develop neutralizing antibodies to recombinant von Willebrand factor (rVWF) and Factor VIII (FVIII) (Time Frame: Throughout the study period of approximately 22 months).

Number of participants who develop total binding antibodies to recombinant von Willebrand factor (rVWF) and Factor VIII (FVIII) (Time Frame: Throughout the study period of approximately 22 months).

Number of participants who develop antibodies to Chinese hamster ovary (CHO) proteins, mouse immunoglobulin G (IgG) and rFurin (Time Frame: Throughout the study period of approximately 22 months).

Pharmacokinetics—Incremental recovery (IR) (Time Frame: 30 minutes pre-infusion; and post-infusion at 30 minutes and 1, 6, 12, 24, 48, and 72 hours).

Pharmacokinetics—Terminal half-life (T½) (Time Frame: 30 minutes pre-infusion; and post-infusion at 30 minutes and 1, 6, 12, 24, 48, and 72 hours).

Pharmacokinetics—Mean residence time (MRT) (Time Frame: 30 minutes pre-infusion; and post-infusion at 30 minutes and 1, 6, 12, 24, 48, and 72 hours).

Pharmacokinetics—Area under the curve/dose (AUC/dose) (Time Frame: 30 minutes pre-infusion; and post-infusion at 30 minutes and 1, 6, 12, 24, 48, and 72 hours).

Pharmacokinetics—Area under moment curve/dose (AUMC/dose) (Time Frame: 30 minutes pre-infusion; and post-infusion at 30 minutes and 1, 6, 12, 24, 48, and 72 hours).

Pharmacokinetics—Volume of distribution at steady state (Vss) (Time Frame: 30 minutes pre-infusion; and post-infusion at 30 minutes and 1, 6, 12, 24, 48, and 72 hours).

Pharmacokinetics—Clearance (CL) (Time Frame: 30 minutes pre-infusion; and post-infusion at 30 minutes and 1, 6, 12, 24, 48, and 72 hours).

Number of infusions of recombinant von Willebrand factor (rVWF) and ADVATE (rFVIII) per spontaneous bleeding episode (BE) (Time Frame: Throughout the study period, up to approximately 22 months).

Number of infusions of recombinant von Willebrand factor (rVWF) and ADVATE (rFVIII) per traumatic bleeding episode (BE) (Time Frame: Throughout the study period, up to approximately 22 months).

Weight-adjusted consumption of recombinant von Willebrand factor (rVWF) and ADVATE (rFVIII) per spontaneous bleeding episode (BE) (Time Frame: Throughout the study period, up to approximately 22 months).

Weight-adjusted consumption of recombinant von Willebrand factor (rVWF) and ADVATE (rFVIII) per traumatic bleeding episode (BE) (Time Frame: Throughout the study period, up to approximately 22 months).

Overall hemostatic efficacy rating at resolution of bleed (Time Frame: Throughout the study period, up to approximately 22 months). Used a 4-point scale: Excellent, Good, Moderate, None.

REFERENCES

1. Nichols W L, et al., Haemophilia 2008; 14:171-232.
2. Leebeek F W, Eikenboom J C. N Engl J Med 2016; 375:2067-80.
3. Reininger A J. Hamostaseologie 2015; 35:225-33.
4. European Medicines Agency. VEYVONDI Summary of Product Characteristics. https://www.ema,europa,ed/documents/product-information/veyvondi-epar-product-information_en.pdf.
5. Mannucci P M et al., Blood 1994; 83:3018-27.
6. Turecek P L et al., Hamostaseologie 2009; 20(suppl 1):532-8.
7. Favaloro E J., Blood Transfus. 2016; 14:262-76.
8. Abshire T., Thromb Res 2009; 124(suppl 1):S15-9.
9. Berntorp E., Haemophilia 2008; 14(suppl 5):47-53.
10. Berntorp E., Petrini P., Blood Coagul Fibrinolysis 2005; 16(suppl 1):523-6.
11. Berntorp E., Semin Thromb Hemost 2006; 32:621-5.
12. Abshire T C, et al., Haemophilia 2013; 19:76-81.
13. Abshire T et al., J Thromb Haemost 2015; 13:1585-9.

While exemplary embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed is:

1. A method for prophylactically treating spontaneous bleeding episodes in a human subject with severe von Willebrand Disease (VWD) comprising administering to the subject twice-weekly only a dose of recombinant von Willebrand Factor (rVWF) ranging from at least about 40 IU/kg to about 80 IU/kg for at least 12 months, wherein about is plus or minus 10% form the specified value, thereby reducing the frequency and/or duration of spontaneous bleeding episodes, wherein the spontaneous bleeding episodes are not related to trauma.

2. The method of claim 1, wherein the dose of rVWF ranges from at least about 50 IU/kg to about 80 IU/kg wherein about is plus or minus 10% form the specified value.

3. The method of claim 1, wherein the subject has a baseline VWF ristocetin cofactor activity (VWF:RCo) of 20 IU/dL or less, or is diagnosed with Type 1 VWD.

4. The method of claim 1, wherein the subject is diagnosed with Type 2A, 2B, or 2M VWD.

5. The method of claim 1, wherein the subject has a VWF:antigen activity (VWF:Ag) of 3 IU/dL or less, or is diagnosed with Type 3 VWD.

6. The method of claim 1, wherein the subject has been administered prophylactic treatment of plasma-derived VWF (pdVWF) within the past 12 months before initial administration of rVWF.

7. The method of claim 1, wherein the subject has experienced at least 3 spontaneous bleeding episodes within the past 12 months.

8. The method of claim 1, wherein the administration occurs on the twice-weekly only schedule selected from the group consisting of every 3 to 4 days.

9. The method of claim 1, wherein the administration occurs on the twice-weekly only schedule selected from the group consisting of on day 1 and day 5, day 2 and day 6, and day 3 and day 7 of a 7 day period.

10. The method of claim 1, wherein the administration occurs on the twice-weekly only schedule selected from the group consisting of once every 72 hours and 84 hours.

11. The method of claim 1, further comprising administering to the subject at least one dose of recombinant Factor VIII (rFVIII).

12. The method of claim 11, wherein the administration of the at least one dose of rFVIII is concomitantly or sequentially administered with the dose of rVWF.

13. The method of claim 1, wherein the subject resumes the prophylactic treatment after receiving elective surgery or oral surgery.

14. The method of claim 13, wherein the subject is administered rVWF without rFVIII before surgery if the elective surgery is minor surgery or oral surgery and the subject has FVIII activity (FVIII:C) of at least 0.4 IU/mL or if the elective surgery is major surgery and the subject has FVIII activity (FVIII:C) of at least 0.8 IU/mL.

15. The method of claim 1, wherein prophylactic treatment efficacy is indicated by a reduction of ≥25%, ≥30%, ≥35%, ≥40%, ≥45%, ≥50%, ≥55%, ≥60%, ≥65%, ≥70%, ≥75%, ≥80%, ≥85%, ≥90%, or ≥95% in annual bleeding rate (ABR) for spontaneous bleeding episodes during rVWF prophylaxis relative to the pretreatment ABR.

16. The method of claim 1, wherein prophylactic treatment efficacy is measured by examining FVIII, FVIII:C, VWF:RCo, VWF:Ag, and/or VWF collagen-binding capacity activities in samples obtained from the subject before and after prophylactic treatment with rVWF.

17. The method of claim 1, wherein prophylactic treatment efficacy is determined after or during a bleeding episode, wherein samples for examining FVIII, FVIII:C, VWF:RCo, VWF:Ag, and/or VWF collagen-binding capacity activities are obtained after the bleeding episode, and further wherein the samples are obtained prior to rVWF administration, 2 hours after rVWF administration and then every 12-24 hours until resolution of the bleeding episode.

18. The method of claim 1, wherein prophylactic treatment efficacy is indicated by an improvement in FVIII, FVIII:C, VWF:RCo, VWF:Ag, and/or VWF collagen-binding capacity activity levels after the prophylactic treatment with rVWF as compared to the levels prior to the prophylactic treatment with rVWF.

19. The method of claim 1, wherein the severe von Willebrand Disease (VWD) is type 3 VWD.

20. The method of claim 1, wherein the spontaneous bleeding episode comprises any one selected from the group consisting of hemarthrosis, epistaxis, muscle bleeding, oral bleeding, and gastrointestinal bleeding.

21. The method of claim 1, wherein the subject administered rVWF has fewer spontaneous bleeding episodes than a control subject that has not received prophylactic treatment, or wherein the subject administered rVWF has fewer spontaneous bleeding episodes over the course of treatment compared to prior to initiating treatment during 12 months of prophylactic treatment with VWF.

22. The method of claim 1, wherein the reduction in frequency is indicated by a reduction of annual bleeding rate (ABRs) for spontaneous bleeding episodes during 12 months of prophylactic treatment with rVWF, wherein the reduction of ABRs for spontaneous bleeding episodes is determined by evaluating ABRs for spontaneous bleeding episodes during prophylactic treatment with rVWF and historical ABRs for spontaneous bleeding episodes.

23. The method of claim 1, wherein the subject receives prophylactic treatment of spontaneous bleeding episodes for a period of years selected from the group consisting of at least 2 years, at least 5 years, and at least 10 years.

* * * * *

UNITED STATES PATENT AND TRADEMARK OFFICE
CERTIFICATE OF CORRECTION

PATENT NO. : 12,128,090 B2
APPLICATION NO. : 16/778771
DATED : October 29, 2024
INVENTOR(S) : Björn Mellgård and Bruce Ewenstein Page 1 of 1

It is certified that error appears in the above-identified patent and that said Letters Patent is hereby corrected as shown below:

In the Claims

Column 109, Line 25, Claim 1:
Replace --form-- with --from--

Column 109, Line 31, Claim 2:
Replace --form-- with --from--

Column 110, Line 63, Claim 22:
Replace --rate-- with --rates--

Signed and Sealed this
Fourth Day of February, 2025

Coke Morgan Stewart
*Acting Director of the United States Patent and Trademark Office*